US012239700B2

(12) United States Patent
Ricke

(10) Patent No.: US 12,239,700 B2
(45) Date of Patent: Mar. 4, 2025

(54) IDENTIFICATION OF VARIABLE INFLUENZA RESIDUES AND USES THEREOF

(71) Applicant: MASSACHUSETTS INSTITUTE OF TECHNOLOGY, Cambridge, MA (US)

(72) Inventor: Darrell O. Ricke, Winchester, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 18/187,133

(22) Filed: Mar. 21, 2023

(65) Prior Publication Data

US 2024/0207386 A1 Jun. 27, 2024

Related U.S. Application Data

(62) Division of application No. 17/186,851, filed on Feb. 26, 2021, now Pat. No. 11,642,407.

(60) Provisional application No. 62/983,519, filed on Feb. 28, 2020.

(51) Int. Cl.
*A61K 39/145* (2006.01)
*A61K 39/12* (2006.01)
*A61K 31/16* (2006.01)

(52) U.S. Cl.
CPC ............ *A61K 39/145* (2013.01); *A61K 39/12* (2013.01); *A61K 31/16* (2013.01)

(58) Field of Classification Search
CPC ........ A61K 39/145; A61K 39/12; A61P 31/16
See application file for complete search history.

(56) References Cited

U.S. PATENT DOCUMENTS

| 7,566,458 | B2 * | 7/2009 | Yang | A61P 37/04 |
| | | | | 435/71.1 |
| 8,512,711 | B2 * | 8/2013 | Lua | C12N 7/00 |
| | | | | 435/5 |
| 9,017,694 | B2 | 4/2015 | Jin et al. | |
| 9,393,297 | B2 * | 7/2016 | Marshall | A61K 45/06 |
| 10,905,756 | B2 | 2/2021 | Eichmeyer et al. | |
| 11,939,356 | B2 * | 3/2024 | Kwong | A61K 39/295 |
| 2012/0014972 | A1 | 1/2012 | Hodges et al. | |
| 2021/0162037 | A1 * | 6/2021 | Jasny | A61K 39/145 |

FOREIGN PATENT DOCUMENTS

| EP | 3730620 | 10/2020 |
| WO | 2008/157419 | 12/2008 |
| WO | 2010/125461 | 11/2010 |
| WO | 2018/078053 | 5/2018 |
| WO | 2014/141125 | 9/2018 |
| WO | 2019/124557 | 6/2019 |
| WO | 2019/145475 | 8/2019 |
| WO | 2019/246363 | 12/2019 |
| WO | 2020/061443 | 3/2020 |

OTHER PUBLICATIONS

International Search Report for PCT/US2021/019864, mailed Jun. 30, 2021.
Zolotarova et al., (2019) "Antigenic Site Variation in the Hemagglutinin of Pandemic Influenza A(H1N1)pdm09 Viruses between 2009-2017 in Ukraine," Pathogens 2019, 8 (194): 1-13.
Opanda et al., (2020) "Assessing antigenic drift and phylogeny of influenza A (H1 N 1) pdm09 virus in Kenya using HA1 sub-unit of the hemagglutinin gene," PLoS ONE 15(2): e0228029.
Korsun et al. (2020) "Genetic diversity of influenza A viruses circulating in Bulgaria during the 2018-2019 winter peason," Journal of Medical Microbiology 2020;69:986-998.
Liu et al. (2021) "Molecular evolution and characterization of hemagglutinin and neuraminidase of influenza A (HiNl) pdm09 viruses isolated in Beijing, China, during the 2017-2018 and 2018-2019 influenza seasons," Archives of Virology (2021) vol. 166, pp. 179-189.

* cited by examiner

*Primary Examiner* — Bao Q Li
(74) *Attorney, Agent, or Firm* — MCDONNELL BOEHNEN HULBERT & BERGHOFF LLP

(57) ABSTRACT

Provided herein are universal prophylactic compositions for preventing infection with influenza viruses by directing the immune response to highly conserved regions of the virus. Also provided are universal therapeutic compositions for treating influenza infection by targeting the highly conserved regions. Methods for using the prophylactic and therapeutic compositions are also provided.

9 Claims, 5 Drawing Sheets

Specification includes a Sequence Listing.

FIG. 1

```
      M  K  A  I  L  V  V  L  L  Y  T  F  F  T  A  N  A  D  T  L
  1   atgaaggcaatactagtagttctgctatatacattcactacgcaaatgcagacacatta   60

C  I  G  Y  H  A  N  N  S  T  D  T  V  D  T  V  L  E  K  N
  61  tgtataggttatcatgcaaacaattcaacagacactgtagacacagtactagaaaagaat  120

V  T  V  T  H  S  V  N  L  L  E  D  K  H  N  G  K  L  C  K
 121  gtaacagtaacacactctgttaaccttctggaagacaagcataacggaaaactatgcaaa  180

L  R  G  V  A  P  L  H  L  G  K  C  N  I  A  G  W  I  L  G
 181  ctaagagggtagccccattgcatttgggtaaatgtaacattgctggctggatcctggga   240

N  P  E  C  E  S  L  S  T  A  S  S  W  S  Y  I  V  E  T  S
 241  aatccagagtgtgaatctctctcaacagcaagttcatggtcctacattgtggaaacatct  300

N  S  D  N  G  T  C  Y  P  G  D  F  I  N  Y  E  E  L  R  E
 301  aattcagacaatggaacgtgttacccaggagatttcatcaattatgaggagctaagagag  360

Q  L  S  S  V  S  S  F  E  R  F  E  I  F  P  K  T  S  S  W
 361  caattgagctcagtgtcatcatttgaaaggtttgagatattccccaagactagttcatgg  420

P  N  H  D  S  N  K  G  V  T  A  A  C  P  H  A  G  A  K  S
 421  cccaatcatgactcgaacaaaggtgtaacggcagcatgtcctcacgctggagccaaaagc  480

F  Y  K  N  L  I  W  L  V  K  K  G  N  S  Y  P  K  L  N  Q
 481  ttctacaaaaacttgatatggctagttaaaaaaggaaattcataccccaaactgaaccaa  540

S  Y  I  N  D  K  G  K  E  V  L  V  L  W  G  I  H  H  P  S
 541  tcctacattaatgataaagggaaagaagtcctcgtgctgtggggaattcaccatccatct  600

T  I  A  D  Q  Q  S  L  Y  Q  N  A  D  A  Y  V  F  V  G  T
 601  actatcgctgaccaacaaagtctctatcagaatgcagatgcatatgttttttgtggaaca  660
```

FIG. 2

```
          S  K  T  S  K  F  K  P  S  I  A  P  R  K  V  R  D  Q
 661  tcaagaacagtaagagttcaagtggaaatagcaccagacccaaagtgaggattcaa  720

E  R  M  N  Y  Y  W  L  F  P  G  D  K  I  P  E
 721  gaagggagaatgaactattactggctacttttcctggagacaaaataccattgaa  780

A  T  G  N  L  V  V  P  R  Y  A  F  F  K  R  F  K  S
 781  gcaactggaaatctagtggtaccgaggtatgcatttttcaagagatttaaatcgtct  840

G  I  I  S  D  F  F  V  D  C  F  T  C  Q  T  P  E
 841  ggtattatcatttcagatttctttgtcgactgcttcacttgtcagacaccggag  900

G  A  I  N  T  S  L  P  F  Q  N  I  H  P  F  I  G  K  C
 901  ggtgctataaacaccagcctcccatttcagaatatacatccatttattggaaaatgt  960

P  K  Y  V  K  S  T  K  L  E  L  A  T  G  L  E  N  V  F  S
 961  ccaaagtatgtaaaaagcacaaaattggagctggccacaggattggagaatgttttcgtct 1020

I  Q  S  R  G  L  F  G  A  I  A  G  F  I  E  G  G  W  T  G
1021  atccaatccagaggcctattcggggcaattgcaggcttcattgaagggggatggacagga 1080

M  V  D  G  W  Y  G  Y  H  H  Q  N  E  Q  G  S  G  Y  A  A
1081  atggtagatggatggtacggttatcaccatcaaaatgagcagggttcaggatatgcagc 1140

D  L  K  S  T  Q  N  A  I  D  K  I  T  N  K  V  N  S  V  I
1141  agactcgaagagcacacaaaatgccattgacaagattactaacaagtaaattctgtatt 1200

E  K  M  N  T  Q  F  T  A  V  G  K  E  F  N  K  L  E  K  R
1201  gaaaagatgaatacacagttcacagcagtgggtaaagagttcaacaaccctggagaaaga 1260

I  E  N  L  N  K  K  V  D  D  G  F  L  D  I  W  T  Y  N  A
1261  atagagaatctaaataaaaaagttgatgatggtttcctggacatttggacttacaatgcc 1320

E  L  L  V  L  L  E  N  E  R  T  L  D  Y  H  D  S  N  V  K
1321  gaactgttgttctattggaaaatgaaagaactttggactatcacgattcaaatgtgaag 1380

N  L  Y  E  K  V  R  S  Q  L  K  N  N  A  K  E  I  G  N  G
1381  aacttgtatgaaaaagtaaggagccagttaaaaaacaatgccaaggaaattggaaacggc 1440

C  F  E  F  Y  H  K  C  D  N  T  C  M  E  S  V  K  N  G  T
1441  tgctttgaattttaccacaaatgcgataacacgtgcatggaaagtgtcaaaaatggaact 1500

Y  D  Y  P  K  Y  S  E  E  A  K  L  N  R  E  K  I  D  G  V
1501  tatgactaccccaaatactcagaggaagcaaaattaaacagagaaaaaatagatgggta 1560

K  L  E  S  T  R  I  Y  Q  I  L  A  I  Y  S  T  V  A  S  S
1561  aagctggaatcaacaaggatttaccagattttggcgatctattcaactgtcgcaagttca 1620

L  V  L  V  V  S  L  G  A  I  S  F  W  M  C  S  N  G  S  L
1621  ttggtactagtggtctccctggggcaatcagcttctggatgtgctctaatgggtctcta 1680

Q  C  R  I  C  I  *
1681  cagtgtagaatatgtatttaa
```

FIG. 2 cont.

```
      M  K  A  I  L  V  V  L  L  Y  F  A  R  N  A  D  T  L
   1  atgaaggcaatactagtagtcctgctatatacattttgcgcgcaaatgcagacacatta   60
                  C  I  G  Y  H  A  N  N  S  T  D  T  V  D  T  V  L  E  N  N
  61  tgtataggttatcatgcgaacaattcaacagacactgtagacacagtactagaaaagaat  120

V  T  V  T  N  S  V  N  L  L  E  A  N  G  K  L  C  K
 121  gtaacagtaacaaatctgttaaccttctggaagctaacggaaaactatgcaaa  180

L  R  G  V  A  P  L  H  L  G  K  C  N  I  A  G  W  L  G
 181  ctaagaggggtagccccattgcatttgggtaaatgtaacattgctggctggctggga  240

N  P  E  C  E  L  L  T  A  S  S  W  S  Y  I  V  E  T  S
 241  aatccagagtgtgaactactacccagcaagttcatggtcctacattgtggaacatct  300

A  S  D  N  G  T  C  Y  P  G  D  F  I  D  Y  E  E  L  R  E
 301  gcttcagacaatggaacgtgttacccaggagattcatagattatgaggagctaagagag  360

Q  L  S  S  V  S  S  F  E  R  F  E  I  F  P  K  T  S  S  W
 361  caattgagctcagtgtcatcatttgaaaggtttgagatattcccaaagacaagttcatgg  420

P  N  H  D  T  N  K  G  V  T  A  A  C  P  H  A  G  A  K  S
 421  cccaatcatgacacgaacaaaggtgtaacagcagcatgtcctcatgctggagcgaaatcc  480

F  Y  K  N  L  I  W  L  V  K  K  G  N  S  Y  P  K  L  S  K
 481  ttctacaagaacttgatatggctagttaaaaaggaaattcatacccaaagcttagcaaa  540

S  Y  I  N  N  K  E  K  E  V  L  V  L  W  G  I  H  H  P  P
 541  tcctacattaataacaaggaaaaggaagtcctcgtgctgtggggaattcaccatccacct  600

T  T  A  D  Q  Q  S  L  Y  Q  N  A  D  A  Y  V  F  V  G  S
 601  actactgctgaccaacaaagtctctatcagaatgcagatgcatatgtttttgtgggatca  660

S  R  Y  S  K  F  A  P  E  I  A  A  R  P  K  V  R  D  Q
 661  tcaagatacagcaaattcgcaccggaaatagccgcaagacccaaagtgagggatcaa  720

A  G  R  M  N  Y  Y  W  T  L  L  E  P  G  D  T  I  I  F  E
 721  gcaggaagaatgaactattactggactctgctggaacccggggagacaatcattttcgaa  780

A  T  G  N  L  V  V  P  R  Y  A  F  A  L  N  R  G  S  G  S
 781  gcaactggaaatctagtggtaccgagatatgcatttgccatgaacagaggatctggatct  840

G  I  I  I  S  D  T  P  V  H  D  C  N  T  T  C  Q  T  P  K
 841  ggtattatcatttcagatacaccagtccacgattgcaacacaacttgtcagacacccaag  900

G  A  I  N  T  S  L  P  F  Q  N  I  H  P  I  T  I  G  K  C
 901  ggtgctataaacaccagcctcccatttcagaatatacatccgatcacaattggaaaatgt  960

P  K  Y  V  K  S  T  K  L  R  L  A  T  G  L  R  N  I  P  S
 961  ccaaagtatgtaaaaagcacaaaattgagactggccacaggattgaggaatataccgtct  1020

I  Q  S  R  G  L  F  G  A  I  A  G  F  I  E  G  G  W  T  G
1021  attcaatctagaggcctatttggggccattgccggcttcattgaaggggggtggacaggg  1080
```

FIG. 3

```
          N  A  D  G  W  Y  G  Y  R  H  Q  S  E  Q  G  A  G  Y  A  A
1081 atgctgatggatggtacggttatcgccatcaaatgagcagggtcaggatatgcagcc 1140

D  A  K  S  T  Q  N  A  I  D  A  I  T  N  K  Y  N  S  V  I
1141 gacgctaagagcacaaaatgccattgacgcaattactaacaaagtaaattctgttatt 1200

E  K  M  N  T  Q  F  T  A  V  G  K  E  F  A  L  E  A
1201 gaaaagatgaatacacagttcacagcagtgggtaagagttcagcacctggaagcaga 1260

I  E  N  L  N  K  K  V  D  D  G  F  L  D  I  W  T  Y  N  A
1261 atagagaatctaaataaaaagtcgatgatggtttcctggacatttggacttacaatgcc 1320

E  L  V  I  L  E  N  E  R  T  L  D  Y  N  D  S  N  Y  K
1321 gaactgttggttctattggaaaatgaaagaactttggactatcacgattcaaatgtgaag 1380

E  L  Y  E  K  V  R  A  Q  L  N  N  A  K  I  G  N  G
1381 aactgtatgaaaaagtaagagcccagttaaaaacaatgccaaggaattggaaacggc 1440

C  F  E  F  Y  H  K  C  D  A  A  C  M  E  S  V  K  N  G  T
1441 tgctttgaattttaccacaaatgcgatgccgcctgcatggaaagtgtcaaaaatgggact 1500

Y  D  Y  P  K  Y  S  E  E  A  K  L  N  R  E  A  I  D  G  V
1501 tatgactacccaaaatactcagaggaagcaaaattaaacagagaagcaatagatgggta 1560

K  L  E  S  T  R  I  Y  Q  I  L  A  I  Y  S  T  V  A  S  S
1561 aagctggaatcaacaaggatttaccagatttggcgatctattcaactgtcgccagttca 1620

L  V  L  A  V  S  L  G  A  I  S  F  W  M  C  S  N  G  S  L
1621 ttggtactcgcagtctctcctggggcaatcagcttctggatgtgctctaatgggtctcta 1680

Q  C  R  I  C  I  *
1681 cagtgtagaatatgtatttca
```

A can be replaced with any non-hypervariable amino acid

FIG. 3 cont.

US 12,239,700 B2

IDENTIFICATION OF VARIABLE INFLUENZA RESIDUES AND USES THEREOF

CROSS-REFERENCE TO RELATED APPLICATIONS

This application is a divisional of U.S. application Ser. No. 17/186,851 filed Feb. 26, 2021, which claims the benefit of U.S. Provisional Patent Application Ser. No. 62/983,519, filed Feb. 28, 2020, each of which is incorporated herein by reference.

GOVERNMENT SUPPORT

This invention was made with Government support under Grant No. FA8702-15-D-0001 awarded by the U.S. Air Force. The Government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Mar. 16, 2023 having the file name "21-0895-US-DIV.xml" and is 269,060 bytes in size.

BACKGROUND

Influenza viruses are members of the family Orthomyxoviridae and are divided into three genera: A, B, and C. Influenza A and B viruses cause respiratory infections in humans. Current vaccines are designed to induce immunity to hemagglutinin, one of two glycoproteins present on the surface of influenza viruses. Despite the availability of highly effective vaccines, influenza infection still results in up to 5,000,000 hospitalizations and 500,000 deaths annually worldwide. Currently available vaccines against influenza include up to four influenza hemagglutinin components intended to provide protection against H1N1, H3N2, and influenza B strains. Vaccine compositions are reassessed annually by the World Health Organization (WHO) to accommodate antigenic shift and drift in circulating virus strains. Such a strategy requires diligent surveillance of circulating influenza strains from year to year, and vaccine mismatches resulting from inaccurate predictions or unpredictable HA mutations arising during vaccine manufacture, which can result in increased morbidity and mortality even in vaccinated populations.

Given the shortcomings of the currently available vaccines, there remains a need for prophylactic and therapeutic compositions and methods that can be used to broadly target influenza in view of the high virus mutation rate amongst strains.

SUMMARY OF THE INVENTION

The present disclosure provides immunogenic compositions, methods for immunizing a subject against infection with an influenza virus, methods for inducing an immune response against influenza virus, and methods of reducing an influenza virus infection in a subject in need thereof by administering one or more immunogenic compositions of the disclosure.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with an amino acid residue that is a hypervariable-substitute. In one embodiment, the hypervariable-substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising two or more polypeptides each individually comprising an amino acid sequence of a viral protein comprising one or more hypervariable amino acid residues, wherein each polypeptide individually comprises an amino acid sequence having a substitution of at least one hypervariable amino acid residue with a different, non-hypervariable amino acid residue, and wherein the polypeptides are of the same or different influenza virus strains. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising two or more polypeptides each individually comprising an amino acid sequence of a viral protein comprising one or more hypervariable amino acid residues, wherein each polypeptide individually comprises an amino acid sequence having a substitution of at least one hypervariable amino acid residue with an amino acid residue that is a hypervariable-substitute, and wherein the polypeptides are of the same or different influenza virus strains. In one embodiment, the hypervariable-substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the influenza virus is an influenza A virus strain or an influenza B virus strain, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the influenza virus is an influenza A virus strain or an influenza B virus strain, wherein the amino acid sequence of the polypeptide comprises a substitution of at least one hypervariable amino acid residue with an amino acid residue that is a hypervariable-substitute. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the virus influenza virus is H1N1, H3N2, B/Victoria/2/1987-like, B/Yamagata/16/1988-like, H5N1, or any combination thereof, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the virus influenza virus is H1N1, H3N2, B/Victoria/2/1987-like, B/Yamagata/16/1988-like, H5N1, or any combination thereof, wherein the amino acid sequence of the polypeptide comprises a substitution of at least one hypervariable amino acid residue with an amino acid residue that is a hypervariable-substitute. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the at least one viral protein is a hemagglutinin protein, a neuraminidase protein, a M2 matrix protein, or combinations thereof, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the at least one viral protein is a hemagglutinin protein, a neuraminidase protein, a M2 matrix protein, or combinations thereof, wherein the amino acid sequence of the polypeptide comprises a substitution of at least one hypervariable amino acid residue with an amino acid that is a hypervariable-substitute. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with a different, non-hypervariable amino acid residue, and wherein the polypeptide comprises at least one B cell epitope. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against the at least one B cell epitope. In one embodiment, the immune response comprises production of antibodies that bind the at least one B cell epitope.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with an amino acid that is a hypervariable-substitute, and wherein the polypeptide comprises at least one B cell epitope. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine. In one embodiment, the immunogenic composition elicits an immune response against the at least one B cell epitope. In one embodiment, the immune response comprises production of antibodies that bind the at least one B cell epitope.

In one aspect, the disclosure provides an immunogenic composition comprising at least one polypeptide comprising an amino acid sequence of an influenza viral protein having one or more hypervariable amino acid residues and one or more conserved amino acid residues, wherein the viral protein comprises an amino acid sequence selected from SEQ ID NOs: 1-6, and wherein the amino acid sequence of the polypeptide comprises a substitution of at least one hypervariable amino acid residue with a different, non-hypervariable amino acid residue. In one embodiment, the polypeptide comprises at least one B cell epitope. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against the at least one B cell epitope. In one embodiment, the immune response comprises production of antibodies that bind the at least one B cell epitope. In one embodiment, the hypervariable amino acid which is substituted is selected from one or more underlined amino acid residues set forth in SEQ ID NOs: 1-6.

In one aspect, the disclosure provides an immunogenic composition comprising at least one polypeptide comprising an amino acid sequence of an influenza viral protein having one or more hypervariable amino acid residues and one or more conserved amino acid residues, wherein the viral protein comprises an amino acid sequence selected from SEQ ID NOs: 1-6, and wherein the amino acid sequence of the polypeptide comprises a substitution of at least one hypervariable amino acid residue with an amino acid that is a hypervariable-substitute. In one embodiment, the polypeptide comprises at least one B cell epitope. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against the at least one B cell epitope. In one embodiment, the immune response comprises production of antibodies that bind the at least one B cell epitope. In one embodiment, the hypervariable amino acid which is substituted is selected from one or more underlined amino acid residues set forth in SEQ ID NOs: 1-6.

In any of the foregoing or related embodiments, the immunogenic composition further comprises an adjuvant.

In any of the foregoing and related aspects, the immunogenic composition comprises a nucleic acid encoding the at least one polypeptide.

In one aspect, the disclosure provides a method for immunizing a subject against infection with an influenza virus, comprising administering one or more immunogenic compositions of the disclosure.

In one aspect, the disclosure provides a method for inducing an immune response against influenza virus, comprising administering to a subject one or more immunogenic compositions of the disclosure.

In one aspect, the disclosure provides a method of reducing an influenza virus infection in a subject in need thereof, comprising administering to a subject one or more immunogenic compositions of the disclosure.

In any of the foregoing and related aspects, the administration of one or more immunogenic compositions to the subject results in the production of antibodies against the at least one B cell epitope in the polypeptide.

Other aspects of the disclosure relate to methods for generating an immunogenic composition comprising:
(i) obtaining two or more amino acid sequences of viral proteins from one or more strains of a particular type and/or subtype of influenza virus;
(ii) aligning the amino acid sequences to generate an alignment;
(iii) identifying one or more hypervariable amino acid residues between strains and one or more conserved amino acid residues; and
(iv) substituting at least one hypervariable amino acid residue identified in (iii) with a different, non-hypervariable amino acid residue. In some aspects, the alignment is generated with Dawn, or Clustal-Omega. In some aspects, the method further comprises performing site-specific mutagenesis at each hypervariable amino residue, or combinations thereof, and determining if the mutated viral protein elicits neutralizing antibodies against the multiple strains of influenza virus.

Other aspects of the disclosure relate to immunogenic compositions comprising at least one polypeptide comprising an amino acid sequence of an influenza viral protein having one or more amino acid residues which are conserved between one or more strains of a type and/or subtype of influenza virus, wherein the amino acid sequence of the polypeptide comprises an amino acid sequence comprising the one or more conserved amino acid residues.

In one aspect, the disclosure provides an immunogenic composition comprising two or more polypeptides, each individually comprising an amino acid sequence of a viral protein having one or more amino acid residues which are conserved between one or more strains of a type and/or subtype of influenza virus, wherein each polypeptide individually comprises an amino acid sequence comprising one or more conserved amino acid sequences, and wherein the polypeptides are of the same or different influenza virus strains. In some aspects, the two or more polypeptides are of the same viral protein. In some aspects the two or more polypeptides are of different viral proteins.

In one aspect the disclosure relates to immunogenic compositions comprising at least one polypeptide comprising an amino acid sequence of an influenza viral protein having one or more amino acid residues which are conserved between one or more strains of a type and/or subtype of influenza virus, wherein the amino acid sequence of the polypeptide comprises an amino acid sequence comprising the one or more conserved amino acid residues, and wherein the polypeptide comprises two or more T cell epitopes, wherein each T cell epitope is operably linked to one other, optionally via a linker.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the influenza virus is an influenza A virus strain or an influenza B virus strain, and wherein the amino acid sequence of the polypeptide comprises an amino acid sequence comprising the one or more conserved amino acid residues.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the influenza virus is H1N1, H3N2, B/Victoria/2/1987-like, B/Yamagata/16/1988-like, H5N1, or any combination thereof, and wherein the amino acid sequence of the polypeptide comprises an amino acid sequence comprising the one or more conserved amino acid residues.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the viral protein is a hemagglutinin protein, a neuraminidase protein, a M2 matrix protein, or combinations thereof, and wherein the amino acid sequence of the polypeptide comprises an amino acid sequence comprising the one or more conserved amino acid residues.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the at least one viral polypeptide comprises at least one conserved amino acid sequence selected from SEQ ID NOs: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 151, 153 and 155, and any combination thereof, and wherein the amino acid sequence of the polypeptide comprises an amino acid sequence comprising the one or more conserved amino acid residues.

In any of the foregoing and related aspects, the immunogenic composition comprises a nucleic acid encoding the at least one polypeptide.

In any of the foregoing and related aspects, the immunogenic composition elicits an immune response against the virus. In some aspects, the immune response is a T cell response directed to the one of more T cell epitopes comprising the conserved amino acid residues of the viral protein.

In any of the foregoing and related aspects, the immunogenic composition further comprises an adjuvant.

In some aspects the disclosure provides methods of immunizing a subject against infection with an influenza virus, optionally a T cell or B cell response or both, comprising administering one or more immunogenic compositions of the disclosure.

In some aspects the disclosure provides methods for inducing an immune response against influenza virus, optionally a T cell or B cell response or both, comprising administering one or more immunogenic compositions of the disclosure.

In some aspects the disclosure provides methods of reducing an influenza virus infection in a subject in need thereof, optionally a T cell or B cell response or both, comprising administering one or more immunogenic compositions of the disclosure.

In some aspects, the composition elicits a T cell response against one or more T cell epitopes comprising the conserved amino acid residues of the viral protein.

In other aspects, the disclosure provides methods for generating an immunogenic composition comprising:
(i) obtaining two or more amino acid sequences of viral proteins from multiple strains of a particular type and/or subtype of influenza virus;
(ii) aligning the amino acid sequences to generate an alignment;
(iii) identifying a region of amino acid residues having conserved amino acid residues between strains; and
(iv) generating a polypeptide comprising the region of amino acids identified in (iii). In one embodiment, the alignment is generated with Dawn or Clustal-Omega.

In one embodiment, the methods of the disclosure further comprise determining if the immunogenic composition elicits a T cell response against the multiple strains of influenza virus.

In some aspects, the disclosure provides an immunogenic composition comprising:
(a) one or more immunogenic compositions comprising at least one polypeptide comprising an amino acid sequence of an influenza viral protein having one or more hypervariable amino acid residues and one or more conserved amino acid residues, optionally wherein the influenza virus is an influenza A virus strain or an influenza B virus strain, and wherein the amino acid sequence of the polypeptide comprises a substitution of at least one hypervariable amino acid residue with a different, non-hypervariable amino acid residue; and
(b) one or more immunogenic compositions comprising at least one polypeptide comprising an amino acid sequence of an influenza viral protein having one or more amino acid residues which are conserved between one or more strains of a type and/or subtype of influenza virus, optionally wherein the influenza virus is an influenza A virus strain or an influenza B virus strain, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine.

In one embodiment, the at least one polypeptide of (a) and the at least one polypeptide of (b) are from the same or different viral proteins from the same influenza virus type. In one embodiment, the at least one polypeptide of (a) and the at least on polypeptide of (b) are from the same or different proteins from different influenza virus types. In one embodiment, the at least one polypeptide of (b) comprises two or more polypeptides each individually comprising a T cell epitope. In one embodiment, the two or more polypeptides comprise same amino acid sequence. In one embodiment, the two or more polypeptides comprise different amino acid sequences. In one embodiment, the two or more polypeptides are derived from the same viral protein. In one embodiment the two or more polypeptides are derived from different viral proteins. In one embodiment, the influenza virus is H1N1, H3N2, B/Victoria/2/1987-like, B/Yamagata/16/1988-like, H5N1, or any combination thereof. In one embodiment, the two or more polypeptides are operably linked to each other, optionally comprising a linker and/or spacer between each polypeptide. In one embodiment, the one or more compositions of (a) and the one ore more compositions of (b) further comprise an adjuvant.

In some aspects, the disclosure provides an immunogenic composition comprising:
(a) one or more immunogenic compositions comprising at least one polypeptide comprising an amino acid sequence of an influenza viral protein having one or more hypervariable amino acid residues and one or more conserved amino acid residues, the viral protein is a hemagglutinin protein, a neuraminidase protein, a M2 matrix protein, or combinations thereof, and wherein the amino acid sequence of the polypeptide comprises a substitution of at least one hypervariable amino acid residue with a different, non-hypervariable amino acid residue; and
(b) one or more immunogenic compositions comprising at least one polypeptide comprising an amino acid sequence of an influenza viral protein having one or more amino acid residues which are conserved between one or more strains of a type and/or subtype of influenza virus, the viral protein is a hemagglutinin protein, a neuraminidase protein, a M2 matrix protein, or combinations thereof, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against at least one T cell epitope, at least one B cell epitope, or combinations thereof. In one embodiment, the immune response comprises production of antibodies that bind B cell epitopes, eliciting a T cell response against T cell epitopes, or both.

In some aspects, the disclosure provides an immunogenic composition comprising:

(a) one or more immunogenic compositions comprising at least one polypeptide comprising an amino acid sequence of an influenza viral protein having one or more hypervariable amino acid residues and one or more conserved amino acid residues, wherein the at least one polypeptide comprises an amino acid sequence selected from SEQ ID NOs: 1-6, or combinations thereof, and wherein the amino acid sequence of the polypeptide comprises a substitution of at least one hypervariable amino acid residue with a different, non-hypervariable amino acid residue; and (b) one or more immunogenic compositions comprising at least one polypeptide comprising an amino acid sequence of an influenza viral protein having one or more amino acid residues which are conserved between one or more strains of a type and/or subtype of influenza virus, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against at least one T cell epitope, at least one B cell epitope, or combinations thereof. In one embodiment, the immune response comprises production of antibodies that bind B cell epitopes, eliciting a T cell response against T cell epitopes, or both.

In some aspects, the disclosure provides an immunogenic composition comprising:

(a) one or more immunogenic compositions comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with a different, non-hypervariable amino acid residue, and wherein the hypervariable amino acid which is substituted is selected from one or more underlined amino acid residues set forth in SEQ ID NOs: 1-6; and (b) one or more immunogenic compositions comprising at least one polypeptide comprising an amino acid sequence of an influenza viral protein having one or more amino acid residues which are conserved between one or more strains of a type and/or subtype of influenza virus, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against at least one T cell epitope, at least one B cell epitope, or combinations thereof. In one embodiment, the immune response comprises production of antibodies that bind B cell epitopes, eliciting a T cell response against T cell epitopes, or both.

In one embodiment, the at least one polypeptide of (b) comprises at least one conserved amino acid sequence selected from SEQ ID NOs: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 151, 153, and 155, or any combination thereof.

In any of the foregoing or related aspects, the immunogenic composition comprises a nucleic acid encoding the at least one polypeptide of (b).

Other aspects of the disclosure relate to methods for immunizing a subject against infection with an influenza virus, comprising administering one or more immunogenic composition of (a) and one or more immunogenic compositions of (b).

Other aspects of the disclosure relate to methods for inducing an immune response in a subject to protect against infection with an influenza virus, or reducing an influenza virus infection comprising administering one or more immunogenic composition of (a) and one or more immunogenic compositions of (b).

In one embodiment, the immunogenic composition of (a) is administered prior to, simultaneously with, or subsequently to administration of the immunogenic composition (b).

Other aspects of the disclosure relate to methods for inducing an immune response or reducing an influenza virus infection in a subject in need thereof who has received or is receiving one or more compositions of (a), the method comprising: administering to the subject an effective amount of one or more compositions of (b).

Other aspects of the disclosure relate to methods for inducing an immune response in a subject in need thereof who has received or is receiving one or more compositions of (b), the method comprising: administering to the subject an effective amount of one or more compositions of (a).

Other aspects of the disclosure relate to methods for reducing an influenza virus infection in a subject, comprising administering to the subject an immunogenic composition comprising: one or more compositions of any of (a); and one or more compositions of (b). In one embodiment, the immunogenic composition of (a) is administered prior to, simultaneously with, or subsequently to administration of the immunogenic composition (b).

In other aspects, the disclosure provides nucleic acid molecules comprising a nucleotide sequence having substantial complementarity to a nucleotide sequence encoding a polypeptide derived from a viral protein of influenza, wherein the at least one polypeptide comprises conserved amino acid sequence between multiple strains of a particular type and/or subtype of influenza virus. In some embodiments, the nucleic acid molecule is an RNA interference (RNAi) molecule. In some embodiments, the RNAi molecule is an siRNA or miRNA molecule. In some embodiments, the nucleic acid molecule is an antisense oligonucleotide. In some embodiments, the nucleic acid encodes for one or more polypeptides. In some embodiment, the one or more polypeptides comprise the same amino acid sequence. In some embodiments, the one or more polypeptides comprise different amino acid sequences. In some embodiments, wherein the one or more polypeptides are derived from the same viral protein. In some embodiments, wherein the one or more polypeptides are derived from different viral proteins. In some embodiments, the one or more polypeptides are operably linked to each other, optionally comprising a linker and/or spacer between each polypeptide. In some embodiments, the nucleic acid is formulated in a composition comprising an adjuvant. In some embodiments, the influenza virus is an influenza A virus strain or an influenza B virus strain. In some embodiments, the influenza virus is H1N1, H3N2, B/Victoria/2/1987-like, B/Yamagata/16/1988-like, H5N1, or any combination thereof. In some embodiments, the viral protein is a hemagglutinin protein, a neuraminidase protein, a M2 matrix protein, or combinations thereof. In some embodiments, the composition elicits an immune response against the virus. In some embodiments, the immune response is a T cell response directed to one of more T cell epitopes. In some embodiments, the nucleic acid encodes a conserved amino acid sequence selected from SEQ ID NOs: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 151, 153 and 155, or any combination thereof.

In some embodiments, the disclosure provides method for immunizing a subject against infection with an influenza virus, methods for inducing an immune response against influenza virus, and methods of reducing an influenza virus infection in a subject in need thereof, comprising administering the nucleic acid molecule of the disclosure. In some embodiments, the nucleic acid molecule elicits a T cell response directed to one of more T cell epitopes. In some embodiments, the method further comprises determining if the nucleic acid molecule elicits a T cell response against the multiple strains of influenza virus.

In other aspects, the disclosure provides methods of treating an influenza infection, comprising administering the nucleic acid molecule of the disclosure, optionally in a delivery vehicle.

BRIEF DESCRIPTION OF FIGURES

FIG. 1 is a schematic showing yearly variations in hemagglutinin amino acid sequence from influenza A H1N1.

FIG. 2 provides the amino acid sequence (SEQ ID NO: 1) and nucleic acid sequence (SEQ ID NO: 169) of influenza A hemagglutinin. Hypervariable residues are indicated by a box whereas highly conserved regions are underlined.

FIG. 3 provides the amino acid sequence (SEQ ID NO: 157) and nucleic acid sequence (SEQ ID NO: 170) of influenza A hemagglutinin where hypervariable residues have been replaced with alanine (shown using a box).

DETAILED DESCRIPTION

The present disclosure provides compositions and methods for inducing an immune response across strains of influenza virus. Specifically, hypervariable residues and highly conserved regions of amino acid sequences have been identified in various influenza viral proteins that can be exploited to induce a universal immune response amongst strains.

Identification of Influenza Residues

Influenza is caused by a virus that attacks mainly the upper respiratory tract—the nose, throat and bronchi and rarely also the lungs. The infection usually lasts for about a week. It is characterized by sudden onset of high fever, myalgia, headache and severe malaise, non-productive cough, sore throat, and rhinitis. Most people recover within one to two weeks without requiring any medical treatment. However, in the very young, the elderly and people suffering from medical conditions such as lung diseases, diabetes, cancer, kidney or heart problems, influenza poses a serious risk. In these people, the infection may lead to severe complications of underlying diseases, pneumonia and death. Annual influenza epidemics are thought to result in between three and five million cases of severe illness and between 250,000 and 500,000 deaths every year around the world.

Influenza virus is a member of Orthomyxoviridae family. There are three subtypes of influenza viruses, designated influenza A, influenza B, and influenza C. The influenza virion contains a segmented negative-sense RNA genome, which encodes the following proteins: hemagglutinin (HA), neuraminidase (NA), matrix (MI), proton ion-channel protein (M2), nucleoprotein (NP), polymerase basic protein 1 (PBI), polymerase basic protein 2 (PB2), polymerase acidic protein (PA), and nonstructural protein 2 (NS2). The HA, NA, MI, and M2 are membrane associated, whereas NP, PBI, PB2, PA, and NS2 are nucleocapsid associated proteins. The MI protein is the most abundant protein in influenza particles. The HA and NA proteins are envelope glycoproteins, responsible for virus attachment and penetration of the viral particles into the cell. Specifically, HA binds the influenza virus to cells with sialic acid-containing on surface structures on their membranes.

Both HA and NA proteins are the sources of the major immunodominant epitopes for virus neutralization and protective immunity, making them important components for prophylactic influenza vaccines. The genetic makeup of influenza viruses allows frequent minor genetic changes, known as antigenic drift. Thus, the amino acid sequence of the major antigens of influenza, particularly HA, is highly variable across groups, subtypes and strains. For this reason, current seasonal influenza vaccines need to be revised every 1-3 years to account for mutations in HA and NA proteins (antigenic drift). A further limitation of the current vaccine approach is that the influenza strains used in the vaccine are selected by the WHO/CDC based on the agencies' best guess as to the prevalent influenza strains for the upcoming flu season. Often times, the guess is not accurate, and the vaccine strains do not match the seasonal influenza strains, limiting the effectiveness of the seasonal vaccines. Seasonal vaccines are also not designed to provide protection against pandemic strains that can result from antigen shift. Further, as the name suggests, seasonal vaccines must be administered every year.

Pandemic outbreaks of influenza are caused by the emergence of a pathogenic and transmissible virus to which the human population is immunologically naive. Because the virus is new, the human population has little to no immunity against it. The virus spreads quickly from person-to-person worldwide. Three times in the last century, the influenza A viruses have undergone major genetic changes mainly in their H-component, resulting in global pandemics and large tolls in terms of both disease and deaths. The most infamous pandemic was "Spanish Flu" which affected large parts of the world population and is thought to have killed at least 40 million people in 1918-1919. More recently, two other influenza A pandemics occurred in 1957 ("Asian influenza") and 1968 ("Hong Kong influenza") and caused significant morbidity and mortality globally. In contrast to current influenza epidemics, these pandemics were associated with severe outcomes also among healthy younger persons, albeit not on such a dramatic scale as the "Spanish flu" where the death rate was highest among healthy young adults. More recently, limited outbreaks of a new influenza subtype A (H1N1) directly transmitted from swine to humans have occurred in Mexico in 2009 and are being detected in an increasing number of countries. Currently, the mortality rate associated with swine-origin H1N1 influenza viruses appears to be similar to that of seasonal influenza strains. However, increased surveillance and detection of swine-origin H1N1 influenza could push the mortality rates higher. Due to antigenic drift, and even more dramatic alterations known as antigenic shift, pandemic influenza antigens (e.g., the HA amino acid sequence of the pandemic strain) are highly unpredictable. Thus, vaccines have traditionally been unavailable until the later stages of a pandemic.

There is an unmet need for influenza vaccines that can better address the current problems of antigenic drift, antigenic shift, and virus mismatch by providing broader protection against multiple influenza strains, including both seasonal and pandemic strains. There is also an unmet need for influenza vaccines that provide longer lasting immunity, particularly vaccines that would not have to be administered every year.

In some embodiments, the present disclosure provides immunogenic compositions that direct the immune response to highly conserved areas, surface exposed areas of the viral proteins, e.g., the HA and/or NA proteins. In some embodiments, the immunogenic compositions additionally comprise the M2 ectodomain of the virus. In yet another embodiment, the immunogenic compositions additionally comprise additional influenza proteins including internal virus proteins, e.g., the M1, NEP, NS1, NS2, PA, PB1, and PB2 proteins. Specifically, by mutating (e.g., substituting) hypervariable amino acid residues and/or generating polypeptides comprising highly conserved amino acid sequences, the compositions and methods described herein can be used to induce an immune response against different strains of influenza, including future strains that may develop due to antigenic shift.

In one embodiment, the present disclosure provides immunogenic compositions comprising one or more polypeptides derived from influenza proteins, wherein at least one hypervariable amino acid residue is replaced by a conserved, non-hypervariable amino acid residue. In one embodiment, the non-hypervariable amino acid residue is selected from amino acid residues with non-polar or neutral side charge. In one embodiment, the non-hypervariable amino acid residue is selected from alanine, glycine, valine, leucine, isoleucine and methionine.

In one embodiment, the present disclosure provides immunogenic compositions comprising one or more polypeptides derived from influenza proteins, wherein at least one hypervariable amino acid residue is replaced by an amino acid residue that is a conserved, hypervariable-substitute. In one embodiment, the hypervariable-substitute is selected from amino acid residues with non-polar or neutral side charge. In one embodiment, the hypervariable-substitute is selected from alanine, glycine, valine, leucine, isoleucine and methionine.

In some embodiments, the immunogenic composition comprises an influenza protein or polypeptide having a highly conserved regions as described herein. In some embodiments, the immunogenic composition comprises an influenza protein or polypeptide having a highly conserved regions annotated in any one of SEQ ID NOs: 171-193. In some embodiments, the protein or polypeptide comprises a non-hypervariable amino acid residue at an amino acid residue that is a hypervariable amino acid residue as annotated in any one of SEQ ID NOs: 171-193. In some embodiments, the protein or polypeptide comprises a hypervariable-substitute at an amino acid residue that is a hypervariable amino acid residue as annotated in any one of SEQ ID NOs: 171-193.

Influenza A

In some embodiments, the methods and compositions described herein target influenza A. Influenza A virus is both best characterized and the most serious threat to public health, capable of inducing massive epidemics or pandemics.

In some embodiments, the methods and compositions described herein comprise a recombinant viral protein derived from influenza A. In some embodiments, the viral protein of an influenza A virus is selected from subtypes H1, H2, H3, H4, H5, H6, H7, H8, H9, H10, H11, H12, H13, H14, H15, or H16. In some embodiments, the influenza virus is selected from the group consisting of H1N1, H3N2, H5N1, and H7N9. In some embodiments, the type A virus is a seasonal strain, such as, /Texas/36/1991, A/Singapore/1986, A/New Caledonia/20/1999, A/Solomon Islands/03/2006, A/Brisbane/59/2007, or A/Wisconsin/67/2005. In some embodiments, the type A virus is a pandemic strain such as A/California/07/2009, A/California/04/2009, A/Belgium/145/2009, A/South Carolina/01/1918, or A/New Jersey/1976.

Influenza B

In some embodiments, the methods and compositions described herein target influenza B. Influenza B viruses generally mutate slower than influenza A viruses.

In some embodiments, the methods and compositions described herein comprise a recombinant viral protein derived from influenza B. In some embodiments, the viral protein of an influenza B virus is selected from a Yamagata lineage strain or a Victoria lineage strain. In some embodiments, the viral protein of an influenza B virus is selected from B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, or B/Brisbane/60/2008.

Hemagglutinin (HA)

In some embodiments, an immunogenic composition described herein comprises a hemagglutinin (HA) recombinant protein, polypeptide or both. In some embodiments, the HA recombinant protein comprises a non-hypervariable amino acid substituted for a hypervariable amino acid residue. In some embodiments, the HA recombinant protein comprises a non-hypervariable amino acid replaced with an amino acid that is a hypervariable-substitute. In some embodiments, the HA polypeptide comprises a highly conserved region of amino acid sequences.

HA is a glycoprotein on the surface of influenza virus responsible for interaction of the virus with host cell receptors. HA proteins on the virus surface are trimers of hemagglutinin protein monomers that are enzymatically cleaved to yield amino-terminal HA1 and carboxy-terminal HA2 polypeptides. The globular head consists exclusively of the major portion of the HA1 polypeptide, whereas the stem that anchors the hemagglutinin protein into the viral lipid envelope is comprised of HA2 and part of HA1. The globular head of a hemagglutinin protein includes two domains: the receptor binding domain (RBD), an ~148-amino acid residue domain that includes the sialic acid-binding site, and the vestigial esterase domain, a smaller ~75-amino acid residue region just below the RBD. The top part of the RBD adjacent to the 2,6-sialic acid recognition sites includes a large region (amino acids 131-143, 170-182, 205-215 and 257-262, 1918 numbering) (referred to herein as the RBD-A region) of over 6000 Å2 per trimer that is 95% conserved between A/South Carolina/1/1918 (1918 SC) and A/California/04/2009 (2009 CA) pandemic strains. The globular head includes several antigenic sites that include immunodominant epitopes. Examples include the Sa, Sb, Ca1, Ca2 and Cb antigenic sites (see, for example, Caton A J et al, 1982, Cell 31, 417-427). The RBD-A region includes the Sa antigenic site and part of the Sb antigenic site.

H1N1

In some embodiments, the immunogenic composition comprises an HA recombinant protein or polypeptide derived from H1N1. In some embodiments, the recombinant H1N1 HA protein or polypeptide comprises a non-hypervariable amino acid residue at an amino acid position selected from Table 1, or any combination thereof. In some embodiments, the recombinant H1N1 HA protein or polypeptide comprises an amino acid that is a hypervariable-substitute at an amino acid position selected from Table 1, or any combination thereof.

TABLE 1

List of Hypervariable Amino Acid Residues in H1N1 HA Protein

| 13T | 114N | 163K | 202T | 239D | 278A | 338V | 491T |
|-----|------|------|------|------|------|------|------|
| 14T | 137T | 178L | 203A | 241E | 287T | 362V | 516K |
| 52D | 145S | 179N | 214A | 251V | 288P | 382L | 544V |
| 53K | 147K | 180Q | 220T | 256K | 293N | 391K |      |
| 78I | 155H | 185D | 222R | 273T | 300E | 415N |      |
| 86S | 158A | 187G | 225K | 274M | 315I | 419K |      |
| 88S | 159K | 195G | 228K | 275E | 319K | 468N |      |
| 101N| 160S | 200S | 233T | 277N | 331L | 490N |      |

*residue numbering based on straight numbering of SEQ ID NO: 1. SEQ ID NO: 1 indicates these residues in bold.

In some embodiments, the recombinant H1N1 HA polypeptide comprises a highly conserved region of amino acid sequences. In some embodiments, the highly conserved region of amino acid sequences is selected from Table 2, or any combination thereof.

TABLE 2

Highly Conserved Regions in H1N1 HA Protein

| GYHANNST | NVTVTHS | SWSYIVE | QSRGLFGAIAGF |
|----------|---------|---------|---------------|
| (SEQ ID NO 7) | (SEQ ID NO 9) | (SEQ ID NO 11) | (SEQ ID NO 13) |
| QGSGYAAD | ITNKVNS | WTYNAELL | GCFEFYH |
| (SEQ ID NO 15) | (SEQ ID NO 17) | (SEQ ID NO 19) | (SEQ ID NO 21) |
| LGNPEC | EGGWTG | LLENER | |
| (SEQ ID NO 23) | (SEQ ID NO 25) | (SEQ ID NO 27) | |

H3N2

In some embodiments, the immunogenic composition comprises an HA recombinant protein or polypeptide derived from H3N2. In some embodiments, the recombinant H3N2 HA protein or polypeptide comprises a non-hypervariable amino acid residue at an amino acid position selected from Table 3, or any combination thereof. In some embodiments, the recombinant H3N2 HA protein or polypeptide comprises an amino acid that is a hypervariable-substitute at an amino acid position selected from Table 3, or any combination thereof.

TABLE 3

List of Hypervariable Amino Acid Residues in H3N2 HA Protein

| 7L | 26T | 73Q | 110Y | 151T | 172H | 189Q | 214S | 242I | 296E | 391D | 494I |
|----|-----|-----|------|------|------|------|------|------|------|------|------|
| 9Y | 41I | 78E | 117D | 153S | 173L | 202G | 215S | 243P | 315R | 394N | 495G |
| 14V | 47N | 91Q | 137N | 154A | 174N | 205K | 218I | 245R | 327Q | 400L | 500G |
| 16A | 49R | 94G | 138N | 156I | 175F | 206D | 219T | 277R | 328S | 402G | 505N |
| 18K | 61N | 98K | 140S | 158R | 176K | 208I | 228A | 278S | 342K | 422I | 506V |
| 19L | 64I | 99K | 144T | 160N | 179A | 209F | 238R | 291G | 362M | 466K | 509D |
| 22Y | 66E | 107S | 147T | 161S | 187N | 212A | 239I | 292K | 363V | 468K | 522E |
| 25S | 69D | 108K | 149N | 171T | 188E | 213Q | 241N | 294K | 377R | 469K | 545V |
| 546A | 560I | 561R | 562C | 563N | 559N | | | | | | |

*residue numbering based on straight numbering of SEQ ID NO: 3. SEQ ID NO: 3 indicates these residues in bold In some embodiments, the recombinant H3N2 HA polypeptide comprises a highly conserved region of amino acid sequences. In some embodiments, the highly conserved region of amino acid sequences is selected from Table 4, or any combination thereof.

TABLE 4

Highly Conserved Regions in H3N2 HA Protein

| | | | |
|---|---|---|---|
| LCLGHHA (SEQ ID NO 61) | GNLIAPRGYF (SEQ ID NO 63) | LKLATGMRN (SEQ ID NO 65) | FGAIAGF IENGWEG (SEQ ID NO 67) |
| KFHQIEKEF (SEQ ID NO 69) | DLTDSEM (SEQ ID NO 71) | LRENAED (SEQ ID NO 73) | |

Influenza B

In some embodiments, the immunogenic composition comprises an HA recombinant protein or polypeptide derived from influenza B. In some embodiments, the recombinant influenza B HA protein or polypeptide comprises a non-hypervariable amino acid residue at an amino acid position selected from Table 5, or any combination thereof. In some embodiments, the recombinant influenza B HA protein or polypeptide comprises an amino acid that is a hypervariable-substitute at an amino acid position selected from Table 5, or any combination thereof.

TABLE 5

List of Hypervariable Amino Acid Residues in Influenza B HA Protein

| | | | | | | |
|---|---|---|---|---|---|---|
| 55H | 95R | 151K | 180K | 213E | 277T | 570V |
| 63E | 96V | 152I | 181N | 217A | 282I | |
| 71K | 123P | 161I | 183T | 218K | 314K | |
| 73L | 131H | 163N | 187P | 224K | 328E | |
| 86K | 132I | 164G | 188L | 245G | 494E | |
| 88T | 137H | 165N | 190I | 248N | 513R | |
| 90K | 141N | 177K | 195I | 267V | 520D | |
| 91I | 144N | 178N | 197T | 270S | 566I | |

*residue numbering based on straight numbering of SEQ ID NO: 5. SEQ ID NO: 5 indicates these residues in bold.

In some embodiments, the recombinant influenza B HA polypeptide comprises a highly conserved region of amino acid sequences. In some embodiments, the highly conserved region of amino acid sequences is selected from Table 6, or any combination thereof.

TABLE 6

Highly Conserved Regions in Influenza B HA Protein

| | | | |
|---|---|---|---|
| VKTATQG EVNVTG (SEQ ID NO 194) | NCTDLDVAL (SEQ ID NO 95) | TSGCFPIMH DRTKIRQL (SEQ ID NO 97) | NLLRGYE (SEQ ID NO 99) |
| TMAWAVP (SEQ ID NO 101) | EDGGLPQS GRIWDYM (SEQ ID NO 103) | LPLIGEAD CLHE (SEQ ID NO 105) | YGGLNKSKP YYTG (SEQ ID NO 107) |
| CPIWVKTPL (SEQ ID NO 109) | GFFGAIAGF LEGGWEGM (SEQ ID NO 111) | AGWHGYTSHGAHG (SEQ ID NO 113) | AVAADLKSTQEA (SEQ ID NO 115) |
| KITKNLNSLSELE (SEQ ID NO 117) | KNLQRLS (SEQ ID NO 119) | EILELDEK VDDLRADT ISSQIELA VLLSNEGI INSEDEHL LALERKLK KMLGPSA (SEQ ID NO 121) | IGNGCFETKH KCNQTCLD (SEQ ID NO 123) |
| AGEFSLPTFD SLNITAASL (SEQ ID NO 125) | HTILLYYSTA ASSLAVTLM (SEQ ID NO 127) | | |

Neuraminidase (NA)

In some embodiments, an immunogenic composition described herein comprises a neuraminidase (NA) recombinant protein, polypeptide or both. In some embodiments, the NA recombinant protein comprises a non-hypervariable amino acid substituted for a hypervariable amino acid residue. In some embodiments, the NA recombinant protein comprises a non-hypervariable amino acid replaced with an amino acid that is a hypervariable-substitute. In some embodiments, the NA polypeptide comprises a highly conserved region of amino acid sequences.

NA is an enzyme found on the surface of influenza that enables the virus to be released from the host cells. Neuraminidases are enzymes that cleave sialic acid groups from glycoproteins and are required for virus replication. The NA protein also functions during entry of virus into the respiratory tract. The epithelial cells are bathed in mucus, a complex protective coating that contains may sialic acid-containing glycoproteins. When influenza virions enter the respirator tract, they are trapped in mucus where they bind sialic acids. This interaction would prevent the viruses from binding to a susceptible cell were it not for the action of the NA protein. When a virus particle encounters a cell, it binds the sialic acid-containing receptor and is rapidly taken into the cell before the NA protein can cleave the carbohydrate from the cell surface.

The NA is a tetramer of four identical polypeptides. Each polypeptide contains about 470 amino acids arranged in four domains, an N-terminal cytoplasmic sequence, followed by a membrane-anchoring hydrophobic transmembrane domain and a thin stalk of variable length, ending in a globular "head" domain that carries the enzyme active site. Crystal structures of NA encompass the catalytically active heads, either proteolytically cleaved from the virus or engineered as a soluble secreted protein. The intact NA has not been crystallized, but a cryoelectron microscopy study of the X-31 (A/Aichi/68, H3N2) reassortant virus has revealed considerable detail at near atomic resolution. The structure confirms that the N2 NA protrudes slightly further than the HA from the viral membrane, that there are 40-50 NA spikes per virion, and that these occur in clusters amid 300-400 HA spikes on an average sized virion of diameter 120 nm.

H1N1

In some embodiments, the immunogenic composition comprises an NA recombinant protein or polypeptide derived from H1N1. In some embodiments, the recombinant H1N1 NA protein or polypeptide comprises a non-hypervariable amino acid residue at an amino acid position selected from Table 7, or any combination thereof. In some embodiments, the recombinant H1N1 NA protein or polypeptide comprises an amino acid that is a hypervariable-substitute at an amino acid position selected from Table 7, or any combination thereof.

TABLE 7

List of Hypervariable Amino Acid Residues in H1N1 NA Protein

| 13I | 34I | 52S | 78Q | 94V | 166V | 222N | 263I | 286S | 331K | 354G | 389I | 432E |
|---|---|---|---|---|---|---|---|---|---|---|---|---|
| 14C | 40L | 53V | 79S | 101S | 173R | 232A | 264V | 287E | 332T | 365I | 393I | 449N |
| 15M | 42N | 59N | 80V | 106I | 188I | 234V | 267V | 288I | 336G | 366S | 395G | 450S |
| 16T | 44N | 64Q | 81V | 126P | 189N | 241I | 269M | 289T | 339S | 367S | 397N | 452T |
| 19M | 45Q | 70S | 82S | 130R | 200N | 248D | 270N | 311E | 340S | 369K | 398E | 453V |
| 20A | 46I | 74F | 84K | 149I | 214D | 249G | 274Y | 314I | 341N | 382G | 416D | 454G |
| 21N | 47E | 75A | 86A | 157T | 220R | 250Q | 275H | 321V | 344N | 385N | 427I | |
| 23I | 48T | 77G | 93P | 163I | 221N | 257R | 285S | 329N | 351F | 386N | 430R | |

*residue numbering based on straight numbering of SEQ ID NO: 2. SEQ ID NO: 2 indicates these residues in bold.

In some embodiments, the recombinant H1N1 NA polypeptide comprises a highly conserved region of amino acid sequences. In some embodiments, the highly conserved region of amino acid sequences is selected from Table 8, or any combination thereof.

TABLE 8

Highly Conserved Regions in H1N1 NA Protein

| | | | |
|---|---|---|---|
| MNPNQKIITIGS (SEQ ID NO 29) | RIGSKGDVFV (SEQ ID NO 31) | REPFISCS (SEQ ID NO 33) | TFFLTQGAL LNDKHSNGT (SEQ ID NO 35) |
| KDRSPYR (SEQ ID NO 37) | FESVAWSASACHDG (SEQ ID NO 39) | WLTIGISGPD (SEQ ID NO 41) | GAVAVLKY (SEQ ID NO 155) |
| ILRTQESEC (SEQ ID NO 43) | YEECSCYPD (SEQ ID NO 45) | CVCRDNWHGS NRPWVSFNQNL (SEQ ID NO 47) | NGVWIGRTKS (SEQ ID NO 49) |
| GFEMIWDPNGWT (SEQ ID NO 51) | WSGYSGSFV QHPELTGL (SEQ ID NO 53) | RPCFWVEL (SEQ ID NO 55) | WTSGSSISFCGV (SEQ ID NO 57) |
| WSWPDGAELPF (SEQ ID NO 59) | | | |

H3N2

In some embodiments, the immunogenic composition comprises an NA recombinant protein or polypeptide derived from H3N2. In some embodiments, the recombinant H3N2 NA protein or polypeptide comprises a non-hypervariable amino acid residue at an amino acid position selected from Table 9, or any combination thereof. In some embodiments, the recombinant H3N2 NA protein or polypeptide comprises an amino acid that is a hypervariable-substitute at an amino acid position selected from Table 9, or any combination thereof.

TABLE 9

List of Hypervariable Amino Acid Residues in H3N2 NA Protein

| | | | | | | | | | |
|---|---|---|---|---|---|---|---|---|---|
| 16T | 43N | 73I | 143V | 194V | 249K | 329N | 356D | 386P | 432E |
| 18S | 44S | 75K | 147D | 197D | 263V | 331S | 367S | 387N | 435E |
| 23F | 45P | 81L | 149V | 199K | 265T | 332S | 369K | 392I | 437L |
| 26I | 46P | 82A | 150R | 208N | 267T | 336H | 370L | 399D | 464I |
| 30I | 51M | 93N | 155Y | 215I | 303V | 338L | 372S | 400R | 468P |
| 40Y | 52L | 126P | 161N | 216V | 307I | 339D | 380I | 401G | |
| 41E | 56T | 127D | 172K | 220K | 310Y | 344E | 381E | 402N | |
| 42F | 62I | 140L | 176I | 221E | 313V | 346G | 385N | 416S | |

*residue numbering based on straight numbering of SEQ ID NO: 4. SEQ ID NO: 4 indicates these residues in bold.

In some embodiments, the recombinant H3N2 NA polypeptide comprises a highly conserved region of amino acid sequences. In some embodiments, the highly conserved region of amino acid sequences is selected from Table 10, or any combination thereof.

TABLE 10

Highly Conserved Regions in H3N2 NA Protein

| | | |
|---|---|---|
| QFALGQGTT (SEQ ID NO 75) | AWSSSSC (SEQ ID NO 77) | LRTQESEC (SEQ ID NO 79) |
| EECSCYP (SEQ ID NO 81) | CSGLVGDTPR (SEQ ID NO 83) | GVKGWAFD (SEQ ID NO 85) |
| NRCFYVELIRG (SEQ ID NO 87) | VFCGTSGTYG (SEQ ID NO 89) | GSWPDGA (SEQ ID NO 91) |

Influenza B

In some embodiments, the immunogenic composition comprises an NA recombinant protein or polypeptide derived from influenza B. In some embodiments, the recombinant influenza B NA protein or polypeptide comprises a non-hypervariable amino acid residue at an amino acid position selected from Table 11, or any combination thereof. In some embodiments, the recombinant influenza B NA protein or polypeptide comprises an amino acid that is a hypervariable-substitute at an amino acid position selected from Table 11, or any combination thereof.

TABLE 11

List of Hypervariable Amino Acid Residues in Influenza B NA Protein 42P
45I
49T
61Q
65R
67A
68T
73L
74L
107T
121V
126N
149G
172I
187K
199N
205V
220N
221N
236N
245S
249V
296R
321D
330N
341D
343D
344K
359K
372K
374E
385G
390A
393D
396A
397F
402V
403S
405K
437E
464D
466A

*residue numbering based on straight numbering of SEQ ID NO: 6. SEQ ID NO: 6 indicates these residues in bold.

In some embodiments, the recombinant influenza B NA polypeptide comprises a highly conserved region of amino acid sequences. In some embodiments, the highly conserved region of amino acid sequences is selected from Table 12, or any combination thereof.

TABLE 12

Highly Conserved Regions in Influenza B NA Protein

| | | | |
|---|---|---|---|
| HFALTHYAAQPG (SEQ ID NO 131) | DRNKLRHL (SEQ ID NO 133) | AWSGSACHDG (SEQ ID NO 135) | KYGEAYT DTYHSY (SEQ ID NO 137) |
| LRTQESACNCI (SEQ ID NO 139) | CRFLKIREGR (SEQ ID NO 141) | HTEECTCGFA (SEQ ID NO 143) | YTAKRPFVKL (SEQ ID NO 145) |
| KGGFVHQR (SEQ ID NO 147) | GRWYSRT (SEQ ID NO 149) | EPGWYSFGFE (SEQ ID NO 151) | EMVHDGG (SEQ ID NO 153) |

TABLE 12-continued

Highly Conserved Regions in
Influenza B NA Protein

ALLISPHRFGE
(SEQ ID NO 129)

M2 Ectodomain

In some embodiments, an immunogenic composition described herein comprises an M2 ectodomain (M2e) recombinant protein, polypeptide or both. In some embodiments, the M2e recombinant protein comprises a non-hypervariable amino acid substituted for a hypervariable amino acid residue. In some embodiments, the M2e recombinant protein comprises a non-hypervariable amino acid replaced with an amino acid residue that is a hypervariable-substitute. In some embodiments, the M2e polypeptide comprises a highly conserved region of amino acid sequences.

The M2 protein is a surface protein on the influenza virion encoded by the M segment. The M segment encodes MI from unspliced mRNA and M2 protein by mRNA splicing. M2 forms homotetramers and possesses ion channel activity that allows for acidification of the inside of the virion during endocytosis and facilitates the dissociation of the matrix protein MI from viral ribonucleoprotein complexes. The M2e, which is the exposed portion of the M2 protein found on the virion membrane, is highly conserved among influenza strains. Accordingly, the M2e protein is a target for universal influenza vaccine approaches.

In some embodiments, M2e protein sequences are obtained and aligned using a method described herein (e.g., the Dawn method) to identify hypervariable amino acid residues subject to antigenic shift/drift, and highly conserved regions of amino acid sequences.

In some embodiments, the immunogenic composition comprises an M2e recombinant protein or polypeptide derived from H1N1. In some embodiments, the recombinant H1N1 M2e protein or polypeptide comprises a non-hypervariable amino acid residue at a hypervariable amino acid residue, or any combination thereof. In some embodiments, the recombinant H1N1 M2e polypeptide comprises a highly conserved region of amino acid sequences, or any combination thereof.

In some embodiments, the immunogenic composition comprises an M2e recombinant protein or polypeptide derived from H3N2. In some embodiments, the recombinant H3N2 M2e protein or polypeptide comprises a non-hypervariable amino acid residue at a hypervariable amino acid residue, or any combination thereof. In some embodiments, the recombinant H3N2 M2e polypeptide comprises a highly conserved region of amino acid sequences, or any combination thereof.

In some embodiments, the immunogenic composition comprises an M2e recombinant protein or polypeptide derived from influenza B. In some embodiments, the recombinant influenza B M2e protein or polypeptide comprises a non-hypervariable amino acid residue at a hypervariable amino acid residue, or any combination thereof. In some embodiments, the recombinant influenza B M2e polypeptide comprises a highly conserved region of amino acid sequences, or any combination thereof.

Additional Influenza Proteins

In some embodiments, an immunogenic composition described herein comprises at least one additional influenza protein, polypeptides or both. In some embodiments the at least one additional influenza protein is selected from NP, M1, PA, PB2, PB2, NS1, and NS2. In some embodiments, the additional influenza protein comprises a non-hypervariable amino acid substituted for a hypervariable amino acid residue. In some embodiments, the additional influenza protein comprises a non-hypervariable amino acid replaced with an amino acid residue that is a hypervariable-substitute. In some embodiments, the additional influenza protein comprises a highly conserved region of amino acid sequences.

The nucleoprotein molecules encapsidate the viral single-stranded RNAs. Nucleoprotein molecules also participate in the nuclear import and export of vRNPs and viral replication, and interact with host proteins. The influenza viral polymerase (P complex) is a heterotrimer of subunits PA, PB1 and PB2. The P complex carries out mRNA transcription and replication of the influenza virus. The PA subunit N domain has a cation-dependent endonuclease active-site core; the catalytic residues His41, Glu80, Asp108 and Glu119 are conserved among influenza A subtypes and strains. The nonstructural protein NS1 binds double-stranded RNA (dsRNA) in a non-sequence specific manner. The NS1 protein has a conserved residue, Arg39 that interact with dsRNA. Accordingly, the additional influenza proteins are also targets for universal influenza vaccine approaches.

In some embodiments, the additional influenza protein sequences are obtained and aligned using a method described herein (e.g., the Dawn method) to identify hypervariable amino acid residues subject to antigenic shift/drift, and highly conserved regions of amino acid sequences.

In some embodiments, the immunogenic composition comprises an additional influenza protein or polypeptide derived from H1N1. In some embodiments, the recombinant H1N1 protein or polypeptide comprises a non-hypervariable amino acid residue at a hypervariable amino acid residue, or any combination thereof. In some embodiments, the recombinant H1N1 polypeptide comprises a highly conserved region of amino acid sequences, or any combination thereof.

In some embodiments, the immunogenic composition comprises an additional influenza protein or polypeptide derived from H3N2. In some embodiments, the recombinant H3N2 protein or polypeptide comprises a non-hypervariable amino acid residue at a hypervariable amino acid residue, or any combination thereof. In some embodiments, the recombinant H3N2 polypeptide comprises a highly conserved region of amino acid sequences, or any combination thereof.

In some embodiments, the immunogenic composition comprises an additional influenza protein or polypeptide derived from influenza B. In some embodiments, the recombinant influenza B protein or polypeptide comprises a non-hypervariable amino acid residue at a hypervariable amino acid residue, or any combination thereof. In some embodiments, the recombinant influenza B polypeptide comprises a highly conserved region of amino acid sequences, or any combination thereof.

In some embodiments, the immunogenic composition comprises an additional influenza protein or polypeptide having a highly conserved regions as annotated in any one of SEQ ID NOs: 171-193. In some embodiments, the protein or polypeptide comprises a non-hypervariable amino acid residue at an amino acid residue that is a hypervariable amino acid residue as annotated in any one of SEQ ID NOs: 171-193. In some embodiments, the protein or polypeptide comprises a hypervariable-substitute at an amino acid residue that is a hypervariable amino acid residue as annotated in any one of SEQ ID NOs: 171-193.

Methods for Identifying Hypervariable and Conserved Influenza Residues

In some embodiments, the present disclosure provides methods for identifying hypervariable and conserved residues in an influenza viral protein between types and/or subtypes of strains. In some embodiments, the hypervariable amino acid residues identified by the methods described herein are substituted with a non-hypervariable amino acid (e.g., alanine). In some embodiments, the hypervariable amino acid residues identified by the methods described herein are substituted with an amino acid residue that is a hypervariable-substitute (e.g., alanine). In some embodiments, the highly conserved regions of amino acids are used to generate polypeptides for peptide vaccines and/or as targets of nucleic acids.

In some embodiments, the present disclosure provides methods for evaluating the role of hypervariable and conserved residues on the ability to induce an immune response (e.g., production of antibodies).

Sequence Alignment—Dawn Method

Protein sequence evolutionary conservation analysis improves understanding of protein structure, function, and disease. Multiple sequence alignments of different isolates, orthologs, paralogs, and functional domains provide essential insights into protein function and structure. Evolutionary conservation level is directly correlated with likelihood of missense mutations' functional impact.

Missense mutations are typically either deleterious or neutral in regards to function impact. Deleterious mutations experience negative selection. Neutral mutations are not positively or negatively selected and can drift through populations. A few mutations experience positive selection and become fixed within populations. Aligning sequences from different species enable the estimation of residue functional importance based on sequence divergence of evolutionarily related proteins. Aligned residues that are identical are composed of a combination of functionally important residues and residues not observed to change due to stochastic chance. Aligned residue positions that are different can represent (1) functionally neutral residues, (2) positions that allow limited conservative residue changes of similar amino acid residues, and (3) positions with alignment errors (this varies by alignment tool used).

A protein enzyme typically consists of a globular domain with a conserved inner core with non-conserved residues observed on the solvent exposed surface. Protein folding includes structures like random coils, alpha helices, beta sheets, and loops/turns. Unlike a ball of yarn, protein peptide strands fold into the tertiary structure with the peptide strand traversing into the interior until typically turning in a solvent exposed loop. Residues in the inner core are typically conserved with amino acid substitutions likely impacting protein folding, structure, and/or function. These interior segments are typically what motif signature models such as, Profile analysis, Psi-Blast, and HAMMR, are derived from or trained on. See e.g., Gribskov, M. et al., *Proc. Natl. Acad. Sci.,* 84: 4355-4358 (1987); Altschul, S. F., et al., *Nucl. Acids Res.* 25:3389-3402 (1997); Eddy, S. R., *Bioinformatics,* 14:755-763 (1998). Ideally, these are the segments that should be aligned in a multiple sequence alignment without gapping allowed within each segment. Small insertions and gaps are observed in exterior turns/loops. Pascarella, S., and P. Argos, P., J Mol. Biol., 224: 461-471 (1992).

Multiple sequence alignment of protein sequences provides numerous insights into protein structures and functions. Available solutions for generating multiple sequence alignments is slow, and the resulting alignments are plagued by frequent over gapping. Scientists routinely realign subsegments within alignments to enhance alignment quality. Algorithm developers have treated protein sequences as text strings for comparisons. Some advanced algorithms include knowledge extracted from motifs, profiles, and structures.

In some embodiments, protein sequences are aligned using the Dawn method.

The Dawn multiple sequence alignment and conservation analysis tool uses conserved residues as anchors such that evolutionarily related sequences can be added to the alignment incrementally. This approach reduces the complexity of creating multiple sequence alignment, or of comparing every sequence to every other sequence. This works for both evolutionarily close or distant sequences and combinations of both.

The ability to identify distant orthologs is directly correlated with the proportion of essential residues in a protein. Doolittle, R. F., OF URFS AND ORFS: A Primer on How to Analyze Derived Amino Acid Sequences: University Science Books, (1986), characterized sequence alignments below 25% identity as being the "Twilight Zone"—a limit on sequence alignment approaches. Below 20% identify is termed the "Midnight Zone", an accepted theoretical limit to sequence analysis techniques.

Dawn aligns sequences based on the Divergence Model of protein evolution, and can align and characterize large numbers of related protein sequences rapidly. Using this tool, a performance improvement of at least two orders of magnitude improvement over current methods. Dawn is applied to three pressing challenges: identification of antiviral targets for therapeutics, multigene family alignment, and analysis of human missense mutations (variants). Dawn implements two concepts of (1) conserved core segments and (2) insertions in loops. Using the sequence analysis technique, Dawn is able to align some paralogs deep into the sequence alignment Twilight and Midnight Zones.

In some embodiments, the workflow for multiple sequence alignment strategy comprises:

1. Identify highly conserved protein segments and use these as vertical segments throughout the multiple sequence alignment;
2. Place insertions and gaps in candidate loop segments to align conserved segments. To minimize alignment gaps, align insertions and gaps in a loop region in overlapping alignment positions unless local sequence identity indicate two likely independent mutation events have likely occurred;
3. Residues in two homologs share high sequence identity between conserved segments that are ordered within a domain. Unrelated sequences can share common simple sequence motifs, but these can be ignored;
4. Conserved segments can be approximated by common k-mers between sequences. Multiple homologs will share a common set of ordered k-mers. Multiple unrelated sequences will not share ordered k-mer sequences outside of expected random sharing.

In some embodiments, the following definitions are used to define conserved segments:
- Ai=Multiple sequence alignment position, i, for sequence of interest;
- C(Ai)=−V with V>0—nonconserved position with V different amino acids observed at this alignment position;
- C(Ai)=0—nonconserved position with residue observed missing in sequences for this gene;
- C(Ai)=1—conserved positions for all sequences for this gene for organisms of the same taxonomic class;
- C(Ai)=1.T—conserved position for all sequences for this gene for taxonomic class of this sequence and T-1 additional taxonomic classes; and
- C(Ai)=V with V>1—conserved position with residue conserved in all sequences for V genes.

In some embodiments, the following definitions are used to define conserved variable or non-conserved segments:
- V(Ai)=number of nonconserved residues observed at alignment position, i, for the taxonomic class of interest. Allowable conservative substitutions defined by Bottema were used to define observed nonconservative substitutions. Bottema, C. D. K., et al., *Am J Hum Genet*, (49):820-838 (1991).

In some embodiments, an algorithm, MSAQ-compute.py (Multiple sequence alignment quality compute), developed in Python, is used to evaluate the quality of multiple sequence alignments. The algorithm accepts an MSA in Clustal format as an input, as well as optional parameters for the number of residues that should not be scored at the beginning and end of the alignment. This accommodates cases of partial sequence overlap and avoids imposing a penalty for otherwise good alignments with excess residues at the beginning or end. The algorithm generates an index of all scored positions within the MSA input file and tallies reported residues at each position to generate a consensus sequence for the alignment.

For each sequence in the MSA, the algorithm computes the number of residues that match the consensus sequence, the number of residues that are different from the corresponding position in the consensus sequence (mismatch), the total number of gap characters in the aligned sequence, and the total number of unique gaps in the aligned sequence. These values are reported in a "details" file generated by the algorithm. Additionally, these values are averaged across all sequences in the MSA to generate average match and average mismatch metrics.

The average length of all gaps in the MSA is also reported as well as the total number of gaps present in the alignment (summed across all sequences). Finally, based on the rationale that any gaps in a high quality alignment should overlap (i.e. input sequences should have alignment gaps at roughly the same positions), the number of non-overlapping gaps is computed. To generate this value, all gaps in the alignment are mapped to positions in the consensus sequence to generate ranges of gap positions. The number of such non-overlapping ranges is reported.

In some embodiments, viral protein sequences are selected from GenBank for influenza. For each selected virus protein, subsets are evaluated to measure execution runtimes using a single Linux core (no parallelization).

Alanine Scanning

The methods described supra are used to identify hypervariable amino acid residues. In some embodiments, the importance of a hypervariable amino acid residue for inducing an immune response is determined by alanine scanning.

As described herein, alanine scanning is a technique used to determine the contribution of a specific wild-type residue to the stability or function(s) (e.g., inducing an immune response) of given protein or polypeptide. The technique involves the substitution of an alanine residue for a wild-type residue in a polypeptide, followed by an assessment of the stability or function(s) (e.g., inducing an immune response) of the alanine-substituted derivative or mutant polypeptide and comparison to the wild-type polypeptide. In some embodiments, the residues identified as not critical are further evaluated to modulate the induction of an immune response. A non-limiting example of such analysis is deep mutational scanning. This method allows for the evaluation of large numbers of mutations. Other methods for analyzing the effect of amino acid residue mutations are known in the art. For example, arginine/glutamic acid scanning is employed to study the effects of bulky, charged amino acid residues on antigen binding. In an embodiment, an arginine amino acid in the hypervariable region is replaced by glutamic acid.

Inducing T Cell Responses with Highly Conserved Regions

T cell immune response plays an important role in eliciting and maintaining protective immunity against influenza virus. In a recent human study, repeated influenza virus boosted multifunctional memory CD4+ T cell populations. Specifically, IFN-γ and TNF-α secreting CD4 cell population have been shown to boost anti-virus antibody titers after repeated vaccination, and is correlated with maintenance of protective antibody titers. Trieu, M. C., et al., npj Vaccines, 3:37 (2018). doi:10.1038/s41541-018-0069-1. Similarly, administration of a combination vaccine comprising trivalent influenza vaccine and a VLP based vaccine showed enhanced CD8+ and CD4+ immune response, and CD4+ T-cell response is correlated with neutralization antibody titers. Skibinski, D. A. G., et al., Sci Rep. 8:18007 (2018).

In some embodiments, the present disclosure provides a polypeptide comprising highly conserved regions of amino acid sequences within a viral protein. In some embodiments, the conserved region is a continuous stretch of at least 7, 8, 9, 10, 11, or 12 invariant or minimally variable amino acid residues. In some embodiments, the polypeptide has 100% identity to a highly conserved region provided herein. In some embodiments, the polypeptide has 99%, 98%, 97%, 96%, 95%, 94%, 93%, 92%, 91% or 90% identity to a highly conserved region provided herein.

In some embodiments, a polypeptide comprising a highly conserved region is operably linked to at least one additional polypeptide comprising a different highly conserved region. In some embodiments, a polypeptide comprising a highly conserved region is operably linked to at least one additional polypeptide comprising the same highly conserved region. In some embodiments, 2, 3, 4, 5, 6, 7, 8, 9, 10, 11, 12, 13, 14, 15, 16, 17, 18, 19 or 20 polypeptides comprising highly conserved regions are operably linked to each other, wherein each polypeptide is the same or different. In some embodiments, at least 10, at least 20, at least 30, at least 40 or at least 50 polypeptides comprising highly conserved regions are operably linked to each other, wherein each polypeptide is the same or different.

In some embodiments, a polypeptide or polypeptides operably linked to each other, induce a T cell response, such as virus-specific CD8+ or CD4+ T cell responses. In some embodiments, an virus-specific CD8+ T cell response comprises CD8+ T cell proliferation or CD8+ T cell cytokine production or both, are induced. In some embodiments, CD8" T cell cytokine production increases by at least 5% or at least 10% or at least 15% or at least 20% or at least 25% or at least 30% or at least 35% or at least 40% or at least 45% or at least 50%. In some embodiments, the percentage of CD8" T cells among the total T cell population increases by at least 5% or at least 10% or at least 15% or at least 20% or at least 25% or at least 30% or at least 35% or at least 40% or at least 45% or at least 50%.

In one embodiment, the disclosure provides a method for eliciting T cell response to conserved polypeptides of influenza viruses, the method comprising administering to a subject in need thereof an immunogenic composition comprising at least one influenza virus polypeptide comprising high conserved amino acid sequence, wherein the T cell response immune response to the highly conserved amino acid sequence is elicited in the subject. In one embodiment, eliciting T cell immune response in a subject comprises stimulating cytokine production (e.g., IFN-γ or TNF-α).

In another embodiment, eliciting an immune response in a subject comprises stimulating virus polypeptide-specific CD4+ or CD8+ T cell activity, e.g., priming, proliferation and/or survival (e.g., increasing the effector/memory T cell population). In one aspect, eliciting a T-cell immune response in a subject comprises stimulating virus-specific CD4+ T cell activity (e.g., increasing helper T cell activity). In other aspects, the CD4+ T cell immune response stimulates cell responses (e.g., increasing antibody production). In some embodiments, enhancing T cell immune response in a subject comprises stimulating cytokine production, stimulating antigen-specific CD8+ T cell responses, stimulating antigen-specific CD4+ helper cell responses, increasing the effector memory CD62Llo T cell population, stimulating B cell activity or stimulating virus-specific antibody production, or any combination of the foregoing responses.

In some embodiments, the enhanced immune response comprises an virus-specific CD8+ T cell response, wherein the CD8+ T cell response comprises an increase in the percentage of effector memory CD62Llo T cells among CD8+ T cells.

Inducing B Cell Responses by Targeting Hypervariable Amino Acid Residues

Most neutralizing antibodies bind to the loops that surround the virus receptor binding site and interfere with receptor binding and attachment. Since these loops are highly variable, most antibodies targeting these regions are strain-specific, and elicit limited, strain-specific immunity. Fully human monoclonal antibodies against influenza virus hemagglutinin with broad cross-neutralizing potency have been generated. Functional and structural analysis have revealed that these antibodies interfere with the membrane fusion process and are directed against highly conserved epitopes in the stem domain of the influenza HA protein (Throsby et al., Plos One 12(3): 1-15 (2008); Ekiert et al., Science 324:246-251 (2009), US2009/0311265, US2012/0039898, US2014/0120113).

In some embodiments, the present disclosure provides an influenza viral protein or fragment thereof, wherein hypervariable amino acid residues are replaced with a non-hypervariable amino acid. Non-hypervariable amino acid residues include, but are not limited to, alanine and glycine. In some embodiments, a non-hypervariable amino acid residue is referred to as a hypervariable-substitute. In some embodiments, the hypervariable amino acid residues are replaced with alanine, glycine, valine, leucine, isoleucine, and methionine. In some embodiments, the hypervariable amino acid residues are replaced with alanine and glycine. In some embodiments, the hypervariable amino acids are replaced with the exemplary and/or preferred amino acids to preserve the conformation of the viral protein and to minimize disruption to adjacent or overlapping conserved regions. In some embodiments, bulky and charged arginine amino acid residues are replaced with glutamic acid residues. In some embodiments, the polypeptide comprises a fragment of the amino acid sequence of the viral proteins. In some embodiments, the fragment comprises the entire amino acid sequence of the viral protein. In some embodiments, viral proteins and fragments thereof can be used in combination.

In some embodiments, the present disclosure provides immunogenic composition comprising at least viral protein or fragment thereof wherein 1-5, 6-10, 11-15, 16-20, 21-25, 26-30, 31-35, 36-40, 41-45, 46-50, 51-55, 56-60 hypervariable amino acid residues are replaced with non-hypervariable amino acid residues. In some embodiments at one, two, three, four, five or more hypervariable amino acids are replaced with non-hypervariable amino acid residues.

In some embodiments, the present disclosure provides immunogenic composition comprising at least viral protein or fragment thereof wherein 1-5, 6-10, 11-15, 16-20, 21-25, 26-30, 31-35, 36-40, 41-45, 46-50, 51-55, 56-60 hypervariable amino acid residues are replaced with amino acid residues that are hypervariable-substitute. In some embodiments at one, two, three, four, five or more hypervariable amino acids are replaced with an amino acid residue that is a hypervariable-substitute.

In some embodiments, substituting the hypervariable amino acid residues with non-hypervariable amino acid residues directs the immune response away from the residues subject to antigenic drift/shift and induces an immune response to the highly conserved regions of amino acid sequences. By targeting the highly conserved regions, such polypeptides can be used for protection against current and yet to exist influenza strains.

In some embodiments, the polypeptides described herein induce a B cell response (e.g., antibody production). In some embodiments, the B cell response is an antigen-specific antibody response. In some embodiments, the B cell response elicit neutralizing antibodies directed to the highly conserved regions in the viral protein. In some embodiments, the neutralizing antibodies are neutralizing against multiple strains of influenza viruses.

In another aspect, the disclosure provides a method of directing the specificity of an B cell immune response in a subject by administering to a subject an immunogenic composition comprising the viral protein, wherein one or more hypervariable amino acid residues of the virus protein are replaced with non-hypervariable amino acid residues.

In another embodiment, administration of immunogenic composition having the amino acid residue substitution results in the immune response to be directed to an highly conserved B cell epitope, and thus eliciting one or more protective neutralizing antibodies. In some embodiments, the neutralizing antibodies provide protective immunity against multiple strains of influenza virus.

Targeting Highly Conserved Regions with Nucleic Acid Molecules

In some embodiments, the present disclosure provides nucleic acid molecules having substantial complementarity to a highly conserved region of amino acid residues. Such nucleic acid molecules are capable of disrupting the transcription and/or translation of a viral protein comprising the base sequence.

Exemplary nucleic acid molecules that can modulate protein function include antisense oligonucleotides and RNA interference molecules (e.g., small interfering RNA (siRNA), microRNA (miRNA) and shRNA).

Antisense oligonucleotides are capable of blocking or decreasing the expression of a desired target gene by targeting nucleic acids encoding the gene or subunit thereof. Methods are known to those of ordinary skill in the art for the preparation of antisense oligonucleotide molecules that will specifically bind one or more target gene(s) without cross-reacting with other polynucleotides. Exemplary sites of targeting include, but are not limited to, the initiation codon, the 5' regulatory regions, including promoters or enhancers, the coding sequence, including any conserved consensus regions, and the 3' untranslated region. In some embodiments, the antisense oligonucleotides are about 10 to about 100 nucleotides in length, about 15 to about 50 nucleotides in length, about 18 to about 25 nucleotides in length, or more. In certain embodiments, the oligonucleotides further comprise chemical modifications to increase nuclease resistance and the like, such as, for example, phosphorothioate linkages and 2'-O-sugarmodifications known to those of ordinary skill in the art.

RNA interference (RNAi) is a biological process in which RNA molecules inhibit gene expression or translation by neutralizing targeted mRNA molecules. Specifically, RNAi refers to a post-transcriptional silencing mechanism initiated by small double-stranded RNA molecules that suppress expression of genes with sequence homology. Key to the mechanism of RNAi are small interfering RNA (siRNA) strands, which have complementary nucleotide sequences to a targeted messenger RNA (mRNA) molecule. siRNAs are short, single-stranded nucleic acid molecules capable of inhibiting or down-regulating gene expression in a sequence-specific manner; see, for example, Zamore et al., Cell 101:25 33 (2000); Bass, Nature 411:428-429(2001); Elbashir et al., Nature 411:494-498 (2001); and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. Methods of preparing a siRNA molecule for use in gene silencing are described in U.S. Pat. No. 7,078,196, which is hereby incorporated by reference. Generally, one would prepare siRNA molecules that will specifically target one or more mRNAs without cross-reacting with other polynucleotides. siRNA molecules can be generated by methods known in the art, such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

Nucleic Acids Encoding Influenza Polypeptides

In some aspects, the polypeptides described herein are encoded by a nucleic acid molecule (e.g., DNA, RNA).

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Transcription and translation of coding sequences are typically regulated by "control elements," including, but not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "promoter" is a nucleotide sequence which initiates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. In addition, such promoters can also have tissue specificity, for example, the CD80 promoter is only inducible in certain immune cells, and the myoD promoter is only inducible in muscle cells. It is intended that the term "promoter" or "control element" includes full-length promoter regions and functional (e.g., controls transcription or translation) segments of these regions. A promoter is "derived from" a gene encoding a co-stimulatory molecule if it has the same or substantially the same basepair sequence as a region of the promoter region of the co-stimulatory molecule, complements thereof, or if it displays sequence identity as described below.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Nucleotide sequences selected for use in the present disclosure can be derived from known sources, for example, by isolating the same from cells containing a desired gene or nucleotide sequence using standard techniques. Similarly, the nucleotide sequences can be generated synthetically using standard modes of polynucleotide synthesis that are well known in the art. See, e.g., Edge et al. (1981) Nature 292:756-762; Nambair et al. (1994) Science 223:1299-1301: Jay et al. (1984) J. Biol. Chem. 259:6311-6317. Generally, synthetic oligonucleotides can be prepared by either the phosphotriester method as described by Edge et al., supra, and Duckworth et al. (1981) Nucleic Acids Res. 9:1691-1706, or the phosphoramidite method as described by Beaucage et al. (1981) Tet. Letts. 22:1859, and Matteucci et al. (1981) J. Am. Chem. Soc. 103:3185.

Another method for obtaining nucleic acid sequences for use herein is by recombinant means. Thus, a desired nucleotide sequence can be excised from a plasmid carrying the same using standard restriction enzymes and procedures. Site specific DNA cleavage is performed by treating with the suitable restriction enzyme (or enzymes) under conditions which are generally understood in the art, and the particulars of which are specified by manufacturers of commercially available restriction enzymes. If desired, size separation of the cleaved fragments may be performed by polyacrylamide gel or agarose gel electrophoresis using standard techniques.

Yet another convenient method for isolating specific nucleic acid molecules is by the polymerase chain reaction (PCR). Mullis et al. (1987) Methods Enzymol. 155:335-350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used. This method also allows for the facile addition of nucleotide sequences onto the ends of the DNA product by incorporating these added sequences onto the oligonucleotide primers (see, e.g., PCR Protocols, A Guide to Methods and Applications, Innis et al (eds) Harcourt Brace Jovanovich Publishers, NY (1994)). PCR conditions used for each amplification reaction are empirically determined. A number of parameters influence the success of a reaction. Among them are annealing temperature and time, extension time, Mg2+ and ATP concentration, pH, and the relative concentration of primers, templates, and deoxyribonucleotides.

Once coding sequences for desired proteins have been prepared or isolated, such sequences can be cloned into any suitable vector or replicon. Numerous cloning vectors are known to those of skill in the art, and the selection of an appropriate cloning vector is a matter of choice. Ligations to other sequences are performed using standard procedures, known in the art.

In some aspects, a nucleic acid molecule described herein is provided in an expression vector. In some embodiments, the vector comprises the nucleic acid molecule that codes for the peptides operatively linked to appropriate expression control sequences. Methods of affecting this operative linking, either before or after the nucleic acid molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

A number of viral based systems have been used for gene delivery. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors, such as the modified N2 vector described herein. Retroviral vectors can be constructed using techniques well known in the art. See, e.g., U.S. Pat. No. 5,219,740; Mann et al. (1983) Cell 33:153-159.

Adenovirus based systems have been developed for gene delivery and are suitable for delivering the nucleic acid molecules described herein. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro. For example, adenoviruses can infect human cells of hematopoietic, lymphoid and myeloid origin. Furthermore, adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; Rich et al. (1993) Human Gene Therapy 4:461-476. Adeno-associated viral vector (AAV) can also be used to administer the polynucleotides described herein. AAV vectors can be derived from any AAV serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain one or more functional flanking inverted terminal repeat (ITR) sequences. Functional ITR sequences are necessary for the rescue, replication and packaging of the AAV virion. Thus, an AAV vector includes at least those sequences required in cis for replication and packaging (e.g., functional ITRs) of the virus. The ITR sequence need not be the wild-type nucleotide sequence, and may be altered, e.g., by the insertion, deletion or substitution of nucleotides, so long as the sequence provides for functional rescue, replication and packaging.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is bounded (5' and 3') with functional AAV ITR sequences. Suitable AAV constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179: 1867-1875.

Models for Assessing Prophylactic and Therapeutic Efficacy In Vitro Models

In some embodiments, in vitro evaluation are utilized to screen vaccine candidates. See e.g., Tapia-Calle, G., et al., Vaccines (Basel) 5(3) pii: E21 (2017). doi: 10.3390/vaccines5030021. Dendritic cells (DCs) play an important in the development of innate and adaptive immune responses. In a study, a DC line (MUT-3) and primary monocyte-derived DCs (Mo-DCs) were employed to screen whole inactivated and subunit influenza vaccines. The Mo-DCs were stimulated with both vaccines and showed upregulated protein expression of activation markers (MHC II, CD86 and CD40) and changes in cytokine secretion in response to whole inactivated vaccines. The Mo-DCs additionally showed increase in gene coding for surface markers of DC cells. The results show that Mo-DCs derived from either fresh or frozen/thawed PBMCs could be utilized to screen vaccine candidates.

In another embodiment, long-term cultures of unfractionated PBMCS were employed to assess recall T cell responses to vaccine candidates. See e.g., Tapia-Calle, G., et al., Vaccines (Basel) 7(4). pii: E181 (2019). doi: 10.3390/vaccines7040181. After stimulation with whole inactivated and subunit influenza vaccines. T cell-mediated immune responses, e.g., activation, proliferation, increase in cytotoxic potential and IFN-γ responses were evaluated. CD4+ and CD8+ phenotyping showed that effector and central memory T cells were activated. Additionally, vaccine induced follicular T helper cell responses (TFH) were also elicited.

In some embodiments, long-term cultures human precision-cut lung slices (PCLS) from human donors are used as an ex vivo model to evaluate immune response to stimulation by influenza vaccine. See e.g., Temann, A., et al., Hum Vac Immunother 13(2):351-358 (2017). Upon stimulation with influenza vaccines, PCLS showed upregulation of cytokine secretions, e.g., IFN-γ, TNF-α and IL-2.

In Vivo Models

Various animal models for evaluating influenza vaccines are known in the art. Margine, I., Krammer, F., Pathogens 3(4):845-874 (2014). Immunogenicity and protective efficacy of candidate influenza vaccines have been tested in e.g., chicken, mouse, ferret, pigs, and non-human primates models.

Ferrets were the first species to be successfully infected with human influenza isolates, and is susceptible to a wide range of human isolates without prior adaptation. Ferrets display clinical symptoms similar to human disease when infected with human influenza, although the presence and severity of symptoms vary depending on the challenge viral strain and route of administration.

Wild mice are not natural hosts of the influenza viruses. However, mice are widely used in influenza research due to their small size, low cost, availability of immunological reagents, availability of laboratory mice strains that can be infected with certain influenza, and availability of transgenic mice strains with targeted gene disruptions to study host responses. Generally, influenza viruses require adaption in mice to be able to infect mice and replicate. The process of adaptation, i.e., repeated in vivo passage in mouse lungs will cause antigenic and phenotypic changes in the adapted virus. However, several pathogenic pandemic influenza strains, such as H1N1, H5N1, and H7, are able to cause disease in mice without prior adaption.

Pigs are an attractive model for influenza research as they are naturally infected by both human and avian influenza viruses. Innate and adaptive B- and T-cell immunity against influenza have been characterized in the pig model. Holzer, B., et al., Front. Immunol. 10:98 (2019). doi: 10.3389/fimmu.2019.00098.

Imunogenicity and challenge influenza studies have been conducted in pigs. For example cold adapted 2017-2018 Northern Hemisphere LAIV vaccine Fluenz Tetra (Astra-Zeneca) containing two type A viruses: H1N1 A/Slovenia/2903/2015, MEDI 279432 107.0±0.5 FFU [A/Michigan/45/2015 (H1N1) pdm09—like strain]; H3N2 A/New Caledonia/71/2014, MEDI 263122 107.0±0.5 FFU [A/Hong Kong/4801/2014 (H3N2)—like strain] and two type B (IBV) viruses; (B/Brisbane/60/2008, MEDI 228030) 107.0±0.5 FFU (B/Brisbane/60/2008-like strain) and B/Phuket/3073/2013, MEDI 254977) 107.0±0.5 FFU (B/Phuket/3073/2013-like strain) were administered intranasally to pigs. Holzer, B., et al., Front. Immunol 10:2625 (2019). doi: 10.3389/fimmu.2019.02625. Four weeks after immunization, the pigs were challenged intranasally with wild-type viruses contained in the LAIV vaccine.

Nasal swabs were collected to test virus load. Serum and bronchoalveolar lavage (BAL) fluid were collected and tested for antibody and neutralizing antibody titers in ELISA and microneutralization (MN) assays, respectively. Cellular response were tested in IFN-γ ELISPOT and intracellular cytokine staining of cells collected from peripheral blood, trachea bronchial lymph nodes (TBLNs) and BALs.

Nonhuman primates are naturally infected by human influenza virus, and are considered good models of human responses to influenza infection and vaccination. Although ethical and economical considerations limit the use of non-human primates in influenza vaccine research, their use is challenge experiments are useful in testing pandemic influenza virus strains.

In some embodiments, the immunogenic compositions herein are tested in immunogenicity and/or challenge studies in animal models.

Immunogenic Compositions

Also provided herein are immunogenic compositions (e.g., vaccines) comprising combinations or cocktails of the recombinant viral proteins and/or polypeptides described herein. In some embodiments, the immunogenic compositions comprise a nucleic acid molecule encoding the recombinant viral proteins and/or polypeptides described herein. In some embodiments, the compositions further comprise a pharmaceutically acceptable carrier.

In some embodiments, immunogenic compositions described herein further comprise one or more adjuvants. For example, alum, aluminum salts (Baylor et al., 2002, Vaccine, 20:S18; incorporated herein by reference) and monophosphoryl lipid A (MPL; Ribi et al., 1986, Immunology and Immunopharmacology of Bacterial Endotoxins, Plenum Publ. Corp., NY, p. 407; incorporated herein by reference) can be used as adjuvants in human vaccines. Alternatively or additionally, new compounds are currently being tested as adjuvants in human vaccines, such as: MF59 (See, e.g., Ott et al., "MF59—Design and Evaluation of a Safe and Potent Adjuvant for Human Vaccines" in Vaccine Design: The Subunit and Adjuvant Approach (Powell, M. F. and Newman, M. J. eds.) Plenum Press, New York, 1995, pp. 277-296; incorporated herein by reference); CpG oligodeoxynudeotide (ODN) adjuvants such as CPG 7909 (Cooper et al., 2004, Vaccine, 22:3136; incorporated herein by reference); Monophosphoryl lipid A (MPL) adjuvants and lipid A mimetis including AS04 (Didierlaurent, A. M. et al, J. Immunol., 2009, 183: 6186-6197; incorporated by reference herein), monophosphoryl lipid A (MPL, GSK) and glucopyranosyl lipid A GLA (Immune Design Corporation, IDC); AF03 (Klucker, M. F. et al, J. Pharm Sci., 2012, 101: 4490-4500; incorporated herein by reference); the TLR-3 ligand polyinosinic:polycytidylic acid [poly(I:C)]; TLR9 adjuvants such as IC31 (Riedl, K. et al., Vaccine, 2008, 26: 3461-3468; incorporated herein by reference); imidazoquinolines (double cyclic organic molecules that act as TLR-7/8 agonists) such as imiquimod (R837) or resiquimod (R848); saponins such as QS21 (Ghochikyan et al., 2006, Vaccine, 24:2275; incorporated herein by reference), ISCOMATRIX adjuvant (Duewell, P., et al., J. Immunol, 2011, 187: 55-63; incorporated herein by reference), and Matrix-M.™. (Novavax).

Additionally, some adjuvants are known in the art to enhance the immunogenicity of influenza vaccines, such as poly[di(carboxylatophenoxy)phosphazene] (PCCP; Payne et al., 1998, Vaccine, 16:92; incorporated herein by reference), interferon-gamma. (Cao et al., 1992, Vaccine, 10:238; incorporated herein by reference), block copolymer P1205 (CRL1005; Katz et al., 2000, Vaccine, 18:2177; incorporated herein by reference), interleukin-2 (IL-2; Mbwuike et al., 1990, Vaccine, 8:347; incorporated herein by reference), and polymethyl methacrylate (PMMA; Kreuter et al., 1981, J. Pharm. Sci., 70:367; incorporated herein by reference).

In some embodiments, the immunogenic compositions include one or more inactive agents such as a sterile, biocompatible carrier including, but not limited to, sterile water, saline, buffered saline, or dextrose solution. In some embodiments, the composition contains any of a variety of additives, such as stabilizers, buffers, excipients (e.g., sugars, amino acids, etc.), or preservatives. Pharmaceutically acceptable carriers used in particular embodiments include, but are not limited to, saline, buffered saline, dextrose, water, glycerol, ethanol, and combinations thereof. In some embodiments, the carrier and composition are sterile, and the formulation suits the mode of administration. In some embodiments, an immunogenic composition contains minor amounts of wetting or emulsifying agents, or pH buffering agents. In some embodiments, a pharmaceutical composition is a liquid solution, suspension, emulsion, tablet, pill, capsule, sustained release formulation, or powder. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

In some embodiments, an immunogenic composition is formulated for intradermal injection, intranasal administration or intramuscular injection. In some embodiments, injectables are prepared in conventional forms, either as liquid solutions or suspensions, solid forms suitable for solution or suspension in liquid prior to injection, or as emulsions. In some embodiments, injection solutions and suspensions are prepared from sterile powders, granules, and. General considerations in the formulation and manufacture of pharmaceutical agents for administration by these routes may be found, for example, in Remington's Pharmaceutical Sciences, 19.sup.th ed., Mack Publishing Co., Easton, Pa., 1995; incorporated herein by reference. At present the oral or nasal spray or aerosol route (e.g., by inhalation) are most commonly used to deliver therapeutic agents directly to the lungs and respiratory system. In some embodiments, compositions in accordance with the invention are administered using a device that delivers a metered dosage of composition (e.g., of an optimized HA polypeptide). Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662 (all of which are incorporated herein by reference).

Intradermal compositions may also be administered by devices which limit the effective penetration length of a needle into the skin, such as those described in WO1999/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO1997/37705, and WO1997/13537 (all of which are incorporated herein by reference). Also suitable are ballistic powder/particle delivery devices which use compressed gas to accelerate vaccine in powder form through the outer layers of the skin to the dermis. Additionally, conventional syringes may be used in the classical mantoux method of intradermal administration.

Preparations for parenteral administration include sterile aqueous or nonaqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In some embodiments, the compositions are administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Use

In some embodiments, the polypeptides described herein are capable of eliciting an immune response against an influenza virus. In some embodiments, the polypeptides can be used as vaccines to protect individuals against influenza infection. In some embodiments, the nucleic acid molecules encoding polypeptides described herein are capable of eliciting an immune response against an influenza virus. In some embodiments, the nucleic acid molecules can be used as vaccines to protect individuals against influenza infection.

In some embodiments, the disclosure provides a method of vaccinating a subject against influenza, in particular, against various strains of influenza. Such methods employ the immunogenic compositions of the present disclosure. Accordingly, in some embodiments, the method comprises administering an immunogenic composition to a subject such that an immune response against influenza virus is produced in the subject. In some embodiments, the polypeptides described herein are capable of eliciting neutralizing antibodies to influenza. In some embodiments, the nucleic acid molecules encoding polypeptides described herein are capable of eliciting neutralizing antibodies to influenza.

Immunogenic compositions of the present disclosure can be used to vaccinate individuals using a prime/boost protocol. Such a protocol is described in U.S. Patent Publication No. 2011/0177122, which is incorporated herein by reference in its entirety. In such a protocol, a first immunogenic composition may be administered to the individual (prime) and then after a period of time, a second immunogenic composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition.

In some embodiments, the subject is at risk for infection with influenza. In some embodiments, the subject has been exposed to influenza. For example, the subject may be an elderly individual, a child, an infant or an immunocompromised individual. As used herein, the terms exposed, exposure, and the like, indicate the subject has come in contact with a person or animal that is known to be infected with influenza. Immunogenic compositions of the present disclosure may be administered using techniques well known to those in the art and described herein.

In some embodiments, the polypeptides and immunogenic compositions of the present disclosure is used to protect a subject against infection by antigenically divergent influenza. In some embodiments, the nucleic acid molecules and immunogenic compositions of the present disclosure is used to protect a subject against infection by antigenically divergent influenza.

Methods of preparing and administering immunogenic compositions to a subject in need thereof are well known in the art or readily determined by those skilled in the art. The dosage and frequency of administration may depend on whether the treatment is prophylactic or therapeutic.

The immunogenic composition and polypeptides of the disclosure are suitable for administration to mammals (e.g., primates, (e.g., humans, chimpanzees, monkeys, baboons), rats (e.g., cotton rats), mice, cows (e.g., calves), guinea pigs, ferrets and hamsters). In some embodiments, the disclosure provides a method of inducing an immune response in a mammal, comprising the step of administering a composition (e.g., an immunogenic composition) of the disclosure to the mammal. The compositions (e.g., an immunogenic composition) can be used to produce a vaccine formulation for immunizing a mammal. The mammal is typically a human, and the immunogenic composition typically comprises a polypeptide comprising an amino acid sequence of an influenza viral protein. In some embodiments, the mammal is a human, and the immunogenic composition comprises a nucleic acid molecule encoding a polypeptide comprising an amino acid sequence of an influenza viral protein.

The disclosure also provides a composition of for use as a medicament, e.g., for use in immunizing a patient against influenza infection.

The disclosure also provides the use of a polypeptide as described above in the manufacture of a medicament for raising an immune response in a patient. In some embodiments, the disclosure provides the use of a nucleic acid molecule described herein in the manufacture of a medicament for raising an immune response in a patient.

The immune response raised by these methods and uses will generally include an antibody response, preferably a protective antibody response. Methods for assessing antibody responses after influenza vaccination are well known in the art.

Compositions of the invention can be administered in a number of suitable ways, such as intramuscular injection (e.g., into the arm or leg), subcutaneous injection, intranasal administration, oral administration, intradermal administration, transcutaneous administration, transdermal administration, and the like. The appropriate route of administration will be dependent upon the age, health and other characteristics of the mammal A clinician will be able to determine an appropriate route of administration based on these and other factors.

Immunogenic compositions, and vaccine formulations, may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >50 years old, >60 years old, >65 years, and preferably >75 years), the young (e.g., <6 years old, such as 4-6 years old, <5 years old), and pregnant women. The vaccines are not limited to these groups, however, and may be used more generally in a population.

Treatment can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Administration of more than one dose (typically two doses) is particularly useful in immunologically naive patients. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, and the like.)

Vaccine formulations produced using a composition of the disclosure may be administered to patients at substantially the same time as (e.g., during the same medical consultation or visit to a healthcare professional or vaccination center) other vaccines.

In some embodiments, the immunogenic compositions, polypeptides or nucleic acid molecules described herein are administered as a therapeutic to a subject infected with influenza.

Kits

The immunogenic composition or polypeptide of the disclosure can be provided in a kit. In some embodiments, a nucleic acid molecule of the disclosure is provided in a kit. In some embodiments, the kit includes (a) a container that contains a composition that includes one or more unit doses of the immunogenic composition or polypeptide, and optionally (b) instructions for use. In some embodiments, the kit includes (a) a container that contains a composition that includes one or more unit doses of the immunogenic composition or nucleic acid molecule, and optionally (b) instructions for use. The unit doses of the immunogenic composition or polypeptide are sufficient to cause an immunogenic response (e.g., antibody production) in a subject. In some embodiments, the unit doses of the immunogenic composition or nucleic acid molecule are sufficient to cause an immunogenic response (e.g., antibody production) in a subject. The kit can also include reagents and instructions useful in the testing (assaying) for an immunogenic response. Such methods of assaying for an immunogenic response include, but are not limited to, any of the testing methods described herein. In one embodiment, the kit includes one or more additional agents for treating influenza. For example, the kit includes a first container that contains a composition that includes the immunogenic composition, and a second container that includes the one or more additional agents.

In some embodiments, the instructions provide methods of administering the immunogenic composition, e.g., in a suitable dose, dosage form, or mode of administration (e.g., a dose, dosage form, or mode of administration described herein), to treat a subject who is infected with influenza, or who is at risk of being infected with influenza.

In addition to the immunogenic composition or polypeptide, the composition in the kit can include other ingredients, such as a solvent or buffer, a stabilizer, or a preservative. The agent can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the polypeptide and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "alanine scanning" refers to a technique used to determine the contribution of a specific wild-type residue to the stability or function(s) (e.g., binding affinity) of a given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

The term "ameliorating" refers to any therapeutically beneficial result in the treatment of a disease state, e.g., infection, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g., insertion of about three to about five or even up to about ten, fifteen, or twenty amino acid residues. The inserted residue(s) can be naturally occurring or non-naturally occurring as disclosed above. An "amino acid deletion" refers to the removal of at least one amino acid residue from a predetermined amino acid sequence. The following table provides exemplary and preferred substitutions for all 20 amino acids.

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |

| Original Residues | Exemplary Substitutions | Preferred Substitutions |
| --- | --- | --- |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diaminobutyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, met, Leu, Phe, Ala, norleucine | Leu |

The term "antigen presenting cell" or "APC" is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "base pair" refers to two nucleobases on opposite complementary nucleic acid strands that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds. Base pairing interactions that do not follow these rules can occur in natural, non-natural, and synthetic nucleic acids and are referred to herein as "non-Watson-Crick base pairing" or alternatively "non-complementary base pairing".

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide can have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant has an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In some embodiments, there is one amino acid difference between a starting polypeptide sequence and the sequence derived there from. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from a sequence set forth in the sequence listing table. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from a sequence set forth in the sequence listing table. In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from a sequence set forth in the sequence listing table. In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from a sequence set forth in the sequence listing table.

In certain embodiments, the polypeptides of the disclosure are encoded by a nucleotide sequence. Nucleotide sequences of the disclosure can be useful for a number of applications, including: cloning, gene therapy, protein expression and purification, mutation introduction, DNA vaccination of a host in need thereof, antibody generation for, e.g., passive immunization, PCR, primer and probe generation, and the like. In certain embodiments, the nucleotide sequence of the invention comprises, consists of, or consists essentially of, a nucleotide sequence selected from a sequence set forth in the sequence listing table. In certain embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence selected from a sequence set forth in the sequence listing table. In certain embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence selected from a sequence set forth in the sequence listing table. In certain embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence selected from a sequence set forth in the sequence listing table.

It will also be understood by one of ordinary skill in the art that the polypeptides suitable for use in the compositions and methods disclosed herein can be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues can be made. Mutations can be introduced by standard techniques, such as site-directed mutagenesis and PCR-mediated mutagenesis.

The polypeptides suitable for use in the compositions and methods disclosed herein can, in some embodiments, comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a polypeptide is preferably replaced with another amino acid residue from the same side chain family. In some embodiments, a string of amino acids can be replaced with a structurally similar string that differs in order and/or composition of side chain family members. Alternatively, in some embodiments, mutations can be introduced randomly along all or part of a coding sequence, such as by saturation mutagenesis, and the resultant mutants can be incorporated into polypeptides of the disclosure and screened for their ability to induce an immune response.

As used herein, the term antigen "cross-presentation" refers to presentation of exogenous protein antigens to T cells via MHC class I and class II molecules on APCs.

As used herein, the term "cytotoxic T lymphocyte (CTL) response" refers to an immune response induced by cytotoxic T cells. CTL responses are mediated primarily by CD8" T cells.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a determinant or site on an antigen (e.g., hemagglutinin) to which an antigen-binding protein (e.g., an immunoglobulin, antibody, or antigen-binding fragment) specifically binds. The epitopes of protein antigens can be demarcated into "linear epitopes" and "conformational epitopes". As used herein, the term "linear epitope" refers to an epitope formed from a contiguous, linear sequence of linked amino acids. Linear epitopes of protein antigens are typically retained upon exposure to chemical denaturants (e.g., acids, bases, solvents, cross-linking reagents, chaotropic agents, disulfide bond reducing agents) or physical denaturants (e.g. thermal heat, radioactivity, or mechanical shear or stress). In some embodiments, an epitope is non-linear, also referred to as an interrupted epitope. As used herein, the term "conformational epitope" or "non-linear epitope" refers to an epitope formed from noncontiguous amino acids juxtaposed by tertiary folding of a polypeptide. Conformational epitopes are typically lost upon treatment with denaturants. An epitope typically includes at least 3, 4, 5, 6, 7, 8, 9, 10, 11, 12, 13, 14 or 15 amino acids in a unique spatial conformation. In some embodiments, an epitope includes fewer than 25, 24, 23, 22, 21, 20, 19, 18, 17, 16, 15, 14, 13, 12, 11, 10, 9, 8, 7, 6 or 5 amino acids in a unique spatial conformation. An epitope that is recognized by a T cell receptor is generally referred to as a T-cell epitope. An epitope that is recognized by an antibody or a B cell receptor is generally referred to as a B-cell epitope. Generally, an antibody, or antigen-binding fragment thereof, specific for a particular target molecule will preferentially recognize and bind to a specific epitope on the target molecule within a complex mixture of proteins and/or macromolecules. As used herein, the T and/or B cell epitopes comprises conserved amino acid residues, hypervariable amino acid residues, or combinations thereof of a viral protein. In other embodiments, the T and/or B cell epitopes comprises conserved amino acid residues of the viral proteins.

As used herein, the term "epitope mapping" refers to a process or method of identifying the binding site, or epitope, of an antibody, or antigen-binding fragment thereof, on its target protein antigen. Epitope mapping methods and techniques are provided herein.

As used herein, the term "fragment" in the context of an amino acid sequence refers to an amino acid sequence comprising a portion of consecutive amino acid residues from a parent sequence. In a specific embodiment, the term refers to an amino acid sequence of 8 to 15, 10 to 20, 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, or 200 consecutive amino acid residues of a parent sequence.

As used herein, the term "hemagglutinin protein" (or "HA protein') refers to a protein or polypeptide whose amino acid sequence includes at least one characteristic sequence of an influenza type A or B HA. A wide variety of HA sequences from influenza isolates are known in the art; indeed, the National Center for Biotechnology Information (NCBI) maintains a database (http://www.ncbi.nlm.nih.gov/genomes/FLU/) that, as of the filing of the present application includes approximately 40,000 HA sequences (for type A and B viruses). Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., human, avian, seal etc.). For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus.

As used herein, "conserved" or "highly conserved regions" are influenza virus sequences from different strains, or consensus sequences, which have been employed to provide an antigen with broad protective properties. Sequence alignments are relied on to yield a "consensus" sequence, where many genetic sequences are incorporated into a single sequence. A consensus sequence may thus minimize the genetic distance between vaccine strains and viruses and so may elicit more cross-reactive immune responses than an immunogen derived from any single influenza virus.

As used herein, the term "hybridization" refers to the process of a first single-stranded nucleic acid, or a portion, fragment, or region thereof, annealing to a second single-stranded nucleic acid, or a portion, fragment, or region thereof, either from the same or separate nucleic acid molecules, mediated by Watson-Crick base pairing to form a secondary and/or tertiary structure. Complementary strands of linked nucleobases able to undergo hybridization can be from either the same or separate nucleic acids. Due to the thermodynamically favorable hydrogen bonding interaction between complementary base pairs, hybridization is a fundamental property of complementary nucleic acid sequences. Such hybridization of nucleic acids, or a portion or fragment thereof, may occur with "near" or "substantial" complementarity, as well as with exact complementarity.

As used herein, the term "hypervariable" refers to amino acid residues and/or protein regions that are abundant and surface exposed, and is a primary target of the immune response against the standard influenza vaccine. The immune response to influenza is overwhelmingly driven against the hypervariable regions of the virus. Thus, in traditional influenza vaccination or natural infections, the protective immune response is overwhelmingly directed at a limited number of continuously evolving, strain-specific, primary antigenic determinants on the surface of the influenza proteins, and there is minimal cross reaction with or protection against other serotypes of influenza.

As used herein, the term "non-hypervariable" or "hypervariable-substitute" refers to an amino acid residue that is substituted for a hypervariable amino acid residue, wherein the substitution eliminates or substantially reduces a strain-specific immune response (e.g., antibody response) against the region containing the hypervariable amino acid residue. In some embodiments, the non-hypervariable residue is one that when substituted for the hypervariable amino acid residue, provides surface epitope with reduced antigenicity. In some embodiments, the non-hypervariable residue is selected from is a nonpolar, aliphatic R group amino acid, e.g., alanine, glycine, valine, leucine, isoleucine, and methionine. In some embodiments, the non-hypervariable residue is conserved at the same position in a plurality of influenza strains.

As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

The terms "inducing an immune response" and "enhancing an immune response" are used interchangeably and refer to the stimulation of an immune response (i.e., either passive or adaptive) to a particular antigen. The term "induce" as used with respect to inducing CDC or ADCC refer to the stimulation of particular direct cell killing mechanisms.

As used herein, the term "influenza strains" is based upon, e.g., the ability of influenza to agglutinate red blood cells (RBCS or erythrocytes). Influenza strains are typically categorized based upon their immunologic or antigenic profile. An HAI titer is typically defined as the highest dilution of a serum that completely inhibits hemagglutination. See, e.g., Schild, et al., Bull. Wld Hlth Org., 1973, 48:269-278, etc. Those of skill in the art will be quite familiar with categorization and classification of influenza into strains and the methods to do so. Antibodies specific for particular influenza strains can bind to the virus and, thus, prevent such agglutination. Assays determining strain types based on such inhibition are typically known as hemagglutinin inhibition assays (HI assays or HAI assays) and are standard and well known methods in the art to characterize influenza strains. Of course, those of skill in the art will be familiar with other assays, e.g., ELISA, indirect fluorescent antibody assays, immunohistochemistry, Western blot assays, etc. with which to characterize influenza strains and the use of and discussion herein of HI assays should not be necessarily construed as limiting.

As used herein "influenza types and subtypes" are influenza A and B virus typically associated with influenza outbreaks in human populations. The type A viruses are categorized into subtypes based upon differences within their hemagglutinin and neuraminidase surface glycoprotein antigens. Hemagglutinin in type A viruses has 14 known subtypes and neuraminidase has 9 known subtypes. In humans, currently only about 3 different hemagglutinin and 2 different neuraminidase subtypes are known, e.g., H1, H2, H3, N1, and N2. In particular, two major subtypes of influenza A have been active in humans, namely, H1N1 and H3N2. H1N2, however has recently been of concern.

As used herein, the term "influenza vaccine" refers to an immunogenic composition capable of stimulating an immune response, administered for the prevention, amelioration, or treatment of influenza virus infection. An influenza vaccine may include, for example, attenuated or killed influenza virus, virus-like particles (VLPs) and/or antigenic polypeptides (e.g., the engineered hemagglutinins described herein) or DNA derived from them, or any recombinant versions of such immunogenic materials.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with an immunogenic composition).

The term "in vivo" refers to processes that occur in a living organism.

As used herein, "immunogenic composition" refers to a composition that comprises at least one antigen which elicits an immunological response in the host to which the immunogenic composition is administered. Such immunological responses can be a cellular and/or antibody-mediated immune response to the immunogenic composition.

As used herein, the terms "linked," "operably linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "MHC molecules" refers to two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the terms "NA" and "neuraminidase" refer to any influenza neuraminidase, such as an influenza A neuraminidase, an influenza B neuraminidase, or an influenza C neuraminidase. A typical neuraminidase comprises domains known to those of skill in the art including a cytoplasmic domain, a transmembrane domain, a stalk domain, and a globular head domain. As used herein, the terms "neuraminidase" and "NA" encompass neuraminidase polypeptides that are modified by post-translational processing such as disulfide bond formation, glycosylation (e.g., N-linked glycosylation), As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nucleic acid" is used in its broadest sense and encompasses any compound and/or substance that includes a polymer of nucleotides. These polymers are often referred to as polynucleotides. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). In some embodiments, alignment of sequences is conducted by the Dawn method (Ricke, D. O. & Shcherbina, A. 2015 *IEEE High Performance Extreme Computing Conference (HPEC)*, doi:10.1109.HPEC.2015.7322463 (2015)).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "recombinant influenza vaccine" refers to influenza-specific immunogenic composition comprising one or more of engineered influenza viral proteins described herein (e.g., hemagluttinin, neuraminidase), including, but not limited to whole influenza virus, subunit preparations thereof, virus-like particles, recombinant protein (i.e., preparations composed of recombinant HA purified to varying degree), and DNA- and viral vector-based vaccines. Recombinant influenza vaccines as described herein may optionally contain one or more adjuvants.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The term "T cell" refers to a type of white blood cell that can be distinguished from other white blood cells by the presence of a T cell receptor on the cell surface. There are several subsets of T cells, including, but not limited to, T helper cells (a.k.a. TH cells or CD4" T cells) and subtypes, including $T_H1$, $T_H2$, $T_H3$, $T_H17$, $T_H9$, and THE cells, cytotoxic T cells (i.e., Tc cells, CD8" T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including CD4⁺

FOXP3+ T_reg cells, CD4+FOXP3- T_reg cells, Tr1 cells, Th3 cells, and T_reg 17 cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

As used herein, the terms "T cell activation" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. T cell activation requires at least two signals to become fully activated. The first occurs after engagement of the T cell antigen-specific receptor (TCR) by the antigen-major histocompatibility complex (MHC), and the second by subsequent engagement of co-stimulatory molecules (e.g., CD28). These signals are transmitted to the nucleus and result in clonal expansion of T cells, upregulation of activation markers on the cell surface, differentiation into effector cells, induction of cytotoxicity or cytokine secretion, induction of apoptosis, or a combination thereof.

As used herein, the term "T cell-mediated response" refers to any response mediated by T cells, including, but not limited to, effector T cells (e.g., CD8" cells) and helper T cells (e.g., CD4" cells). T cell mediated responses include, for example, T cell cytotoxicity and proliferation.

As used herein, the terms "therapeutically effective amount" or "therapeutically effective dose," or similar terms used herein are intended to mean an amount of an agent (e.g., a nucleic acid molecule) that will elicit the desired biological or medical response (e.g., an improvement in one or more symptoms of an infection).

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "vaccination" refers to the administration of an immunogenic composition intended to generate an immune response, for example to a disease-causing agent such as influenza. Vaccination can be administered before, during, and/or after exposure to a disease-causing agent, and/or to the development of one or more symptoms, and in some embodiments, before, during, and/or shortly after exposure to the agent. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response. In some embodiments, vaccination includes multiple administrations, appropriately spaced in time, of an immunogenic composition.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

EXAMPLES

Example 1: Identification of Residues in H1N1

To identify highly conserved amino acid residues between strains of a particular type and/or subtype of influenza virus, amino acid sequences were obtained and aligned. Specifically, the Dawn method, described in Ricke, D. O & Shcherbina, A., *IEEE High Performance Extreme Computing Conference (HPEC)*, doi: 1031109/HPEC.2015.7322463 (2015), herein incorporated by reference, was used to align 52,443 influenza A H1N1 hemagglutinin amino acid sequences and 51,784 influenza A H1N1 neuraminidase amino acid sequences. FIG. 1 shows an alignment of a section of amino acid residues in the H1N1 HA protein from strains in years 2009-2019.

SEQ ID NO: 1 provides the amino acid sequence for hemagglutinin from the A/Michigan/45/2015 H1N1 strain. SEQ ID NO: 2 provides the amino acid sequence for neuraminidase from the A/Michigan/45/2015 strain H1N1 strain.

Highly variable residues were identified for both proteins, along with residues having low variability. The following sequence for hemagglutinin indicates hypervariable residues in bold and conserved regions are underlined.

```
                                          (SEQ ID NO: 1)
MKAILVVLLYTFTTANADTLCIGYHANNSTDT

VDTVLEKNVTVTHSVNLLEDKHNGKLCKLRGV

APLHLGKCNIAGWILGNPECESLSTASSWSYI

VETSNSDNGTCYPGDFINYEELREQLSSVSSF

ERFEIFPKTSSWPNHDSNKGVTAACPHAGAKS

FYKNLIWLVKKGNSYPKLNQSYINDKGKEVLV

LWGIHHPSTTADQQSLYQNADAYVFVGTSRYS

KKFKPEIATRPKVRDQEGRMNYYWTLVEPGDK

ITFEATGNLVVPRYAFTMERNAGSGIIISDTP

VHDCNTTCQTPEGAINTSLPFQNIHPITIGKC

PKYVKSTKLRLATGLRNVPSIQSRGLFGAIAG

FIEGGWTGMVDGWYGYHHQNEQGSGYAADLKS

TQNAIDKITNKVNSVIEKMNTQFTAVGKEFNH

LEKRIENLNKKVDDGFLDIWTYNAELLVLLEN

ERTLDYHDSNVKNLYEKVRNQLKNNAKEIGNG

CFEFYHKCDNTCMESVKNGTYDYPKYSEEAKL

NREKIDGVKLESTRIYQILAIYSTVASSLVLV

VSLGAISFWMCSNGSLQCRICI
```

FIG. 2 provides the amino acid sequence and nucleic acid sequences for the H1N1 hemagglutinin protein with the nucleic acid sequences underlined for highly conserved regions and shown by boxes for the hypervariable amino acid residues.

The following sequence for neuraminidase indicates hypervariable residues in bold and conserved regions are underlined.

(SEQ ID NO: 2)
MNPNQKIITIGSICMTIGMANLILQIGNIISI

WVSHSIQIGNQSQIETCNQSVITYENNTWVNQ

TYVNISNINFAAGQSVVSVKLAGNSSLCPVSG

WAIYSKDNSVRIGSKGDVFVIREPFISCSPLE

CRTFFLTQGALLNDKHSNGTIKDRSPYRTLMS

CPIGEVPSPYNSRFESVAWSASACHDGINWLT

IGISGPDSGAVAVLKYNGIITDTIKSWRNNIL

RTQESECACVNGSCFTIMIDGPSDGQASYKIF

RIEKGKIIKSVEMKAPNYHYEECSCYPDSSEI

TCVCRDNWHGSNRPWVSFNQNLEYQMGYICSG

VTGDNPRPNDKTGSCGPVSSNGANGVKGFSFK

YGNGVWIGRTKSISSRKGFEMIWDPNGWTGTD

NKFSIKQDIVGINEWSGYSGSFVQHPELTGLD

CIRPCFWVELIRGRPEENTIWTSGSSISFCGV

NSDTVGWSWPDGAELPFTIDK

Example 2: Identification of Residues in H3N2

Using the same method described in Example 1, hypervariable amino acid residues and highly conserved regions were identified in the hemagglutinin and neuraminidase proteins of H3N2. Specifically, 42,653 hemagglutinin amino acid sequences and 29,491 neuraminidase amino acid sequences were aligned using the Dawn method.

SEQ ID NO: 3 provides the amino acid sequence for hemagglutinin from the A/Mississippi/27/2013 H3N2 strain. SEQ ID NO: 4 provides the amino acid sequence for neuraminidase from the Neuraminidase A/Miyagi/N1289/2005 H3N2 strain.

Highly variable residues were identified for both proteins, along with residues having low variability. The following sequence for hemagglutinin indicates hypervariable residues in bold and conserved regions are underlined.

(SEQ ID NO: 3)
MKTIIALSYILCLVFAQKLPPYGNSTATLCLG

HHALPNGTIVKTITNDRIEVTNATELVQNSSI

GEICDSPHQILDGENCTLIDALLGDPQCDGFQ

NKKWDLFVERSKAYSNCYPYDVPDYASLRSLV

ASSGTLEFNNESFNWTGVTQNGTSSACIRRSN

SSFFSRLNWLTHLNFKYPAINVIMPNNEQFDK

LYIWGVHHPGTDKDQIFLYAQSSGRITVSTKR

SQQAVIPNIGSRPRIRNIPSRISIYWTIVKPG

DILLINSTGNLIAPRGYFKIRSGKSSIMRSDA

PIGKCKSECITPNGSIPNDKPFQNVNRITYGA

CPRYVKQSTLKLATGMRNVPEKQTRGIFGAIA

GFIENGWEGMVDGWYGFRHQNSEGRGQAADLK

STQAAIDQINGKLNRLIGKTNEKFHQIEKEFS

EVEGRIQDLEKYVEDTKIDLWSYNAELLVALE

NQHTIDLTDSEMNKLFEKTKKQLRENAEDMGN

GCFKIYHKCDNACIGSIRNGTYDHNVYRDEAL

NNRFQIKGVELKSGYKDWILWISFAISCFLLC

VAIKGFIMWACQKGNIRCNIRCNICI

The following sequence for neuraminidase indicates hypervariable residues in bold and conserved regions are underlined.

(SEQ ID NO: 4)
MNPNQKIITIGSVSLTISTICFFMQIAILITT

VTLHFKQYEFNSPPNNQVMLCEPTIIERNITE

IVYLTNTTIEKEICPKLAEYRKWSKPQCNITG

FAPFSKDNSIRLSAGGDIWVTREPYVSCDPDK

CYQFALGQGTTLNNVHSNDIVRDRTPYRTLLM

NELGVPFHLGTKQVCIAWSSSSCHDGKAWLHV

CVTGDDKNATASFIYNGRLVDSIVSWSKEILR

TQESECVCINGTCTVVMTDGSASGKADTKILF

IEEGKIVHTSTLSGSAQHVEECSCYPRYPGVR

CVCRDNWKGSNRPIVDINIKDYSIVSSYVCSG

LVGDTPRKNDSSSSSHCLDPNNEEGGHGVKGW

AFDDGNDVWMGRTISEKLRSGYETFXVIEGWS

NPNSKLQINRQVIVDRGNRSGYSGIFSVEGKS

CINRCFYVELIRGRKEETEVLWTSNSIVVFCG

TSGTYGTGSWPDGADINLMPI

Example 3: Identification of Residues in Influenza B

Using the same method described in Example 1, hypervariable amino acid residues and highly conserved regions were identified in the hemagglutinin and neuraminidase proteins of influenza B. Specifically, 20,906 hemagglutinin amino acid sequences and 14,546 neuraminidase amino acid sequences were aligned using the Dawn method.

SEQ ID NO: 5 provides the amino acid sequence for hemagglutinin from the B/Brisbane/60/2008 influenza B strain. SEQ ID NO: 6 provides the amino acid sequence for neuraminidase from the B/Wisconsin/05/2016 influenza B strain.

Highly variable residues were identified for both proteins, along with residues having low variability. The following sequence for hemagglutinin indicates hypervariable residues in bold and conserved regions are underlined.

```
                                        (SEQ ID NO: 5)
MKAIIVLLMVVTSNADRICTGITSSNSPHVVK

TATQGEVNVTGVIPLTTTPTKSHFANLKGTET

RGKLCPKCLNCTDLDVALGRPKCTGKIPSARV

SILHEVRPVTSGCFPIMHDRTKIRQLPNLLRG

YEHIRLSTHNVINAENAPGGPYKIGTSGSCPN

ITNGNGFFATMAWAVPKNDKNKTATNPLTIEV

PYICTEGEDQITVWGFHSDDETQMAKLYGDSK

PQKFTSSANGVTTHYVSQIGGFPNQTEDGGLP

QSGRIVVDYMVQKSGKTGTITYQRGILLPQKV

WCASGRSKVIKGSLPLIGEADCLHEKYGGLNK

SKPYYTGEHAKAIGNCPIWVKTPLKLANGTKY

RPPAKLLKERGFFGAIAGFLEGGWEGMIAGWH

GYTSHGAHGVAVAADLKSTQEAINKITKNLNS

LSELEVKNLQRLSGAMDELHNEILELDEKVDD

LRADTISSQIELAVLLSNEGIINSEDEHLLAL

ERKLKKMLGPSAVEIGNGCFETKHKCNQTCLD

RIAAGTFDAGEFSLPTFDSLNITAASLNDDGL

DNHTILLYYSTAASSLAVTLMIAIFVVYMVSR

DNVSCSICL
```

The following sequence for neuraminidase indicates hypervariable residues in bold and conserved regions are underlined.

```
                                        (SEQ ID NO: 6)
MLPSTIQTLTLFLTSGGVLLSLYVSASLSYLL

YSDILLKFSPTEITAPTMPLDCANASNVQAVN

RSATKGVTLLLLPEPEWTYPRLSCPGSTFQKA

LLISPHRFGETKGNSAPLIIREPFVACGPNEC

KHFALTHYAAQPGGYYNGTRGDRNKLRHLISV

KLGKIPTVENSIFHMAAWSGSACHDGKEWTYI

GVDGPDNNALLKVKYGEAYTDTYHSYANNILR

TQESACNCIGGNCYLMITDGSASGVSECRFLK

IREGRIIKEIFPTGRVKHTEECTCGFASNKTI

ECACRDNRYTAKRPFVKLNVETDTAEIRLMCT

DTYLDTPRPNDGSITGPCESDGDKGSGGIKGG

FVHQRMKSKIGRWYSRTMSKTERMGMGLYVKY

GGDPWADSDALAFSGVMVSMKEPGWYSFGFEI

KDKKCDVPCIGIEMVHDGGKETWHSAATAIYC

LMGSGQLLWDTVTGVDMAL
```

Example 4: Production of B Cell Immune Response

To determine whether the hypervariable residues identified in HA and NA proteins as described in Examples 1-3, alanine scanning of each residue and combinations of residues is performed. FIG. 3 shows an exemplary sequence wherein each hypervariable residue identified in the H1N1 HA protein described in Example 1 is replaced with an alanine.

Each mutated HA and NA protein comprising an alanine is subjected to in vitro and in vivo testing to determine what mutations will elicit an immune response to highly conserved amino acid regions and provide protection against influenza infection.

In one study, mutated HA or NA proteins, or combinations thereof, are administered to a subject (e.g., a pig). Serum, BAL, and TBLN samples are collected and tested in ELISA or neutralization assays to determine antibodies titers to the highly conserved amino acid regions. Generation of such antibodies indicates the immune response has been directed to such regions and thus the mutated proteins are suitable as a universal influenza vaccine. In another study, after administration of the mutated HA or NA proteins, or combinations thereof, subjects are challenged with various influenza virus strains and infection levels are monitored. The ability of the mutated HA or NA proteins to prevent infection by different influenza strains indicates the mutated proteins are suitable as a universal influenza vaccine.

Example 5: Production of T Cell Immune Response

To determine whether the highly conserved regions of amino acids identified in Examples 1-3 are capable of eliciting a T cell immune response, immunogenic compositions comprising polypeptides having amino acid sequences of the conserved regions are generated and administered to subjects. In some studies, polypeptides comprising different regions are combined by operably linking the polypeptides together.

PBMCS are collected at various time points after immunization, and are cultured with 15-mer peptide pools encompassing the sequence of the polypeptide or operably linked polypeptides. T cell activation is measured by assessing proliferation, production of cytokines and/or the cytotoxic ability of the cells against different influenza virus strains. The ability of the polypeptide or operably linked polypeptides to induce cytokine induction or induce killing of different strains by T cells indicates the polypeptide(s) are suitable as a universal influenza vaccine.

In another study, polypeptide(s) or operably linked polypeptides are administered to a subject (e.g., a pig) which is then challenged with various influenza virus strains and infection levels are monitored. The ability of the polypeptide(s) to prevent infection by different influenza strains indicates they are suitable as a universal influenza vaccine.

Example 6: Therapeutic Efficacy of Nucleic Acids Targeting Highly Conserved Regions To determine whether targeting the highly conserved regions identified in Examples 1-3 provides therapeutic efficacy, nucleic acid molecules (e.g., siRNA or miRNA) having substantial complementarity to nucleotide sequences encoding the highly conserved regions are generated.

In one study, a nucleic acid molecule targeting a highly conserved region is contacted with various influenza virus strains. Ability of the viruses to infect cells is assessed after contact. If the nucleic acid molecule disrupts the life cycle of the virus and prevents infection, the nucleic acid molecule may be suitable for treating influenza infection.

| SEQ ID NO | Description | Sequence |
|---|---|---|
| 1 | H1N1 Hemagglutinin A/Michigan/ 45/2015 strain (amino acid) GenBank: MK622940.1 | MKAILVVLLYTTTANADTLCIGYHANNSTDT VDTVLEKNVTVTHSVNLLEDKHNGKLCKLRGV APLHLGKCNIAG<u>WI</u>LGNPECESLSTASSWSYI VETSNSDNGTCYPGDFINYEELREQLSSVSSF <u>ERFEIFPK</u>TSSWPNHDSNKGVTAACPHAGAKS FYKNLIWLVKKGNSYPKLNQSYINDKGKEVLV LWGIHHPSTTADQQSLYQNADAYVFVGTSRYS KKFKPEIATRPKVRDQEGRMNYYWTLVEPGDK ITFEATGNLVVPRYAFTMERNAGSGIIISDTP VHDCNTTCQTPEGAINTSLPFQNIHPITIGKC PKYVKSTKLRLATGLRNVPS<u>IQSRGLFGAIAG FI</u>EGGWTGMVDGWYGYHHQNEQGSGYAADLKS TQNAIDKITNKVNSVIEKMNTQFTAVGKEFNH LEKRIENLNKKVDDGFLDIWTYNAELLVLLEN ERTLDYHDSNVKNLYEKVR<u>N</u>QLKNNAKEIGNG <u>C</u>FEFYHKCDNTCMESVKNGTYDYPKYSEEAKL <u>NREK</u>IDGVKLESTRIYQILAIYSTVASSLVLV VSLGAISFWMCSNGSLQCRICI (underline = highly conserved; bold = hypervariable) |
| 2 | H1N1 Neuraminidase A/Michigan/ 45/2015 strain (amino acid) GenBank: MK622934.1 | MNPNQKIITIGSICMTIGMANLILQIGNIISI WVSHSIQIGNQSQIETCNQSVITYENNTWVNQ TYVNISNINFAAGQSVVSVKLAGNSSLCPVSG WAIYSKDNSVRIGSKGDVFVIREPPFISCSPLE CRTFFLTQGALLNDKHSNGTIKDRSPYRTLMS CPIGEVPSPYNSRFESVAWSASACHDGINWLT IGISGPDSGAVAVLKYNGIITDTIKSWRNNIL RTQESECACVNGSCFTIMIDGPSDGQASYKIF RIEKGKIIKSVEMKAPNYHYEECSCYPDSSEI TCVCRDNWHGSNRPWVSFNQNLEYQMGYICSG VTGDNPRPNDKTGSCGPVSSNGANGVKGFSFK YGNGVWIGRTKSISSRKGFEMIWDPNGWTGTD NKFSIKQDIVGINEWSGYSGSFVQHPELTGLD CIRPCFWVELIRGRPEENTIWTSGSSISFCGV NSDTVGWSWPDGAELPFTIDK (underline = highly conserved; bold = hypervariable) |
| 3 | H3N2 Hemagglutinin A/Mississippi/ 27/2013 strain (amino acid) GenBank: AIK26600.1 | MKTIIALSYILCLVFAQKLPPYGNSTATLCLG HHALPNGTIVKTITNDRIEVTNATELVQ<u>NSSI GE</u>ICDSPHQILDGENCTLIDALLGDPQCDGFQ NKKWDLFVERSKAYSNCYPYDVPDYASLRSLV ASSGTLEFNNESFNWTGVTQNGTSSACIRRSN SSFFSRLNWLTHLNFKYPAINVIMPNNEQFDK LYIWGVHHPGTDKDQIFLYAQSSGRITVSTKR SQQAVIPNIGSRPRIRNIPSRISIYWTIVKPG DILLINSTGNLIAPRGYFKIRSGKSSIMRSDA PIGKCKSECITPNGSIPNDKPFQNVNRITYGA CPRYVKQSTLKLATGMRNVPEKQTRGIFGAIA GFIENGWEGMVDGWYGFRHQNSEGRGQAADLK STQAAIDQINGKLNRLIGKTNEKFHQIEKEFS EVEGRIQDLEKYVEDTKIDLWSYNAELLVALE NQHTIDLTDSEMNKLFEKTKKQLRENAEDMGN GCFKIYHKCDNACIGSIRNGTYDHNVYRDEAL NNRFQIKGVELKSGYKDWILWISFAISCFLLC VAIKGFIMWACQKGNIRCNIRCNICI (underline = highly conserved; bold = hypervariable) |
| 4 | H3N2 Neuraminidase A/Miyagi/N12 89/2005 strain (amino acid) GenBank: AB271522.1 | MNPNQKIITIGSVSLTISTICFFMQIAILITT VTLHFKQYEFNSPPNNQVMLCEPTIIERNITE IVYLTNTTIEKEICPKLAEYRKWSKPQCNITG <u>FA</u>PPFSKDNSIRLSAGGDIWVTREPYVSCDPDK CYQFALGQGTTLNNVHSNDIVRDRTPYRTLLM NELGVPFHLGTKQVCIAWSSSSCHDGKAWLHV CVTGDDKNATASFIYNGRLVDSIVSWSKEILR TQESECVCINGTCTVVMTDGSASGKADTKILF IEEGKIVHTSTLSGSAQHVEECSCYPRYPGVR CVCRDNWKGSNRPIVDINIKDYSIVSSYVCSG LVGDTPRKNDSSSSHCLDPNNEEGGHGVKGW <u>AF</u>DDGNDVWMGRTISEKLRSGYETFXVIEGWS NPNSKLQINRQVIVDRGNRSGYSGIFSVEGKS CINRCFYVELIRGRKEETEVLWTSNSIVVFCG TSGTYGTGSWPDGAD<u>INL</u>MPI |

-continued

SEQUENCE LISTING TABLE

| SEQ ID NO | Description | Sequence |
|---|---|---|
| | | (underline = highly conserved; bold = hypervariable) |
| 5 | Influenza B Hemagglutinin B/Brisbane/60/ 2008 strain (amino acid) GenBank: KX058884.1 | MKAIIVLLMVVTSNADRICTGITSSNSPHVVK TATQGEVNVTGVIPLTTTPTKSHFANLKGTET RGKLCPKCLNCTDLDVALGRPKCTGKIPSARV SILHEVRPVTSGCFPIMHDRTKIRQLPNLLRG YEHIRLSTHNVINAENAPGGPYKIGTSGSCPN ITNGNGFFATMAWAVPKNDKNKTATNPLTIEV PYICTEGEDQITVWGFHSDDETQMAKLYGDSK PQKFTSSANGVTTHYVSQIGGFPNQTEDGGLP QSGRIVVDYMVQKSGKTGTITYQRGILLPQKV WCASGRSKVIKGSLPLIGEADCLHEKYGGLNK SKPYYTGEHAKAIGNCPIWVKTPLKLANGTKY RPPAKLLKERGFFGAIAGFLEGGWEGMIAGWH GYTSHGAHGVAVAADLKSTQEAINKITKNLNS LSELEVKNLQRLSGAMDELHNEILELDEKVDD LRADTISSQIELAVLLSNEGIINSEDEHLLAL ERKLKKMLGPSAVEIGNGCFETKHKCNQTCLD RIAAGTFDAGEFSLPTFDSLNITAASLNDDGL DNHTILLYYSTAASSLAVTLMIAIFVVYMVSR DNVSCSICL (underline = highly conserved; bold = hypervariable) |
| 6 | Influenza B Neuraminidase B/Wisconsin/ 05/2016 strain (amino acid) GenBank: KX007164.1 | MLPSTIQTLTLFLTSGGVLLSLYVSASLSYLL YSDILLKFSPTEITAPTMPLDCANASNVQAVN RSATKGVTLLLLPEPEWTYPRLSCPGSTFQKA LLISPHRFGETKGNSAPLIIREPFVACGPNEC KHFALTHYAAQPGGYYNGTRGDRNKLRHLISV KLGKIPTVENSIFHMAAWSGSACHDGKEWTYI GVDGPDNNALLKVKYGEAYTDTYHSYANNILR TQESACNCIGGNCYLMITDGSASGVSECRFLK IREGRIIKEIFPTGRVKHTEECTCGFASNKTI ECACRDNRYTAKRPFVKLNVETDTAEIRLMCT DTYLDTPRPNDGSITGPCESDGDKGSGGIKGG FVHQRMKSKIGRWYSRTMSKTERMGMGLYVKY GGDPWADSDALAFSGVMVSMKEPGWYSFGFEI KDKKCDVPCIGIEMVHDGGKETWHSAATAIYC LMGSGQLLWDTVTGVDMAL (underline = highly conserved; bold = hypervariable) |
| 7 | H1N1 Hemagglutinin conserved region (amino acid) | GYHANNST |
| 8 | H1N1 Hemagglutinin conserved region (nucleic acid) | ggttatcatgcgaacaattcaaca |
| 9 | H1N1 Hemagglutinin conserved region (amino acid) | NVTVTHS |
| 10 | H1N1 Hemagglutinin conserved region (nucleic acid) | aatgtaacagtaacacactct |

-continued

| SEQ ID NO | Description | Sequence |
|---|---|---|
| 11 | H1N1 Hemagglutinin conserved region (amino acid) | SWSYIVE |
| 12 | H1N1 Hemagglutinin conserved region (nucleic acid) | tcatggtcctacattgtggaa |
| 13 | H1N1 Hemagglutinin conserved region (amino acid) | QSRGLFGAIAGF |
| 14 | H1N1 Hemagglutinin conserved region (nucleic acid) | caatctagaggcctattcggggccattgccggcttc |
| 15 | H1N1 Hemagglutinin conserved region (amino acid) | QGSGYAAD |
| 16 | H1N1 Hemagglutinin conserved region (nucleic acid) | caggggtcaggatatgcagccgac |
| 17 | H1N1 Hemagglutinin conserved region (amino acid) | ITNKVNS |
| 18 | H1N1 Hemagglutinin conserved region (nucleic acid) | attactaacaaagtaaattct |
| 19 | H1N1 Hemagglutinin conserved region (amino acid) | WTYNAELL |
| 20 | H1N1 Hemagglutinin conserved region (nucleic acid) | tggacttacaatgccgaactgttg |
| 21 | H1N1 Hemagglutinin conserved region | GCFEFYH |

-continued

SEQUENCE LISTING TABLE

| SEQ ID NO | Description | Sequence |
|---|---|---|
| | (amino acid) | |
| 22 | H1N1 Hemagglutinin conserved region (nucleic acid) | gcctgctttgaattttaccac |
| 23 | H1N1 Hemagglutinin conserved region (amino acid) | LGNPEC |
| 24 | H1N1 Hemagglutinin conserved region (nucleic acid) | ctgggaaatccagagtgt |
| 25 | H1N1 Hemagglutinin conserved region (amino acid) | EGGWTG |
| 26 | H INI Hemagglutinin conserved region (nucleic acid) | gaagggggtggacaggg |
| 27 | H1N1 Hemagglutinin conserved region (amino acid) | LLENER |
| 28 | H1N1 Hemagglutinin conserved region (nucleic acid) | ctattggaaaatgaaaga |
| 29 | H1N1 Neuraminidase conserved region (amino acid) | MNPNQKI1TIGS |
| 30 | H1N1 Neuraminidase conserved region (nucleic acid) | atgaatccaaaccaaaagataataaccattggttcg |
| 31 | H1N1 Neuraminidase conserved region (amino acid) | RIGSKGDVFV |
| 32 | H1N1 Neuraminidase conserved | agaatcggttccaagggggatgtgtttgtc |

-continued

SEQUENCE LISTING TABLE

| SEQ ID NO | Description | Sequence |
|---|---|---|
| | region (nucleic acid) | |
| 33 | H1N1 Neuraminidase conserved region (amino acid) | REPFISCS |
| 34 | H1N1 Neuraminidase conserved region (nucleic acid) | agggaaccattcatatca |
| 35 | H1N1 Neuraminidase conserved region (amino acid) | TFFLTQGALLNDKHSNGT |
| 36 | H1N1 Neuraminidase conserved region (nucleic acid) | accttcttcttgactcaaggggccttgctaaa tgacaaacattccaatggaacc |
| 37 | H1N1 Neuraminidase conserved region (amino acid) | KDRSPYR |
| 38 | H1N1 Neuraminidase conserved region (nucleic acid) | aaagacaggagcccataccga |
| 39 | H1N1 Neuraminidase conserved region (amino acid) | FESVAWSASACHDG |
| 40 | H1N1 Neuraminidase conserved region (nucleic acid) | tttgagtcagtcgcttggtcagcaagtgcttgtcatgatggc |
| 41 | H1N1 Neuraminidase conserved region (amino acid) | WLTIGISGPD |
| 42 | H1N1 Neuraminidase conserved region (nucleic acid) | tggctaacaattggaatttctggcccagac |

SEQUENCE LISTING TABLE

| SEQ ID NO | Description | Sequence |
|---|---|---|
| 43 | H1N1 Neuraminidase conserved region (amino acid) | ILRTQESEC |
| 44 | H1N1 Neuraminidase conserved region (nucleic acid) | atattgagaacacaagagtctgaatgt |
| 45 | H1N1 Neuraminidase conserved region (amino acid) | YEECSCYPD |
| 46 | H1N1 Neuraminidase conserved region (nucleic acid) | tatgaggaatgctcctgttaccctgat |
| 47 | H1N1 Neuraminidase conserved region (amino acid) | CVCRDNWHGSNRPWVSFNQNL |
| 48 | H1N1 Neuraminidase conserved region (nucleic acid) | tgtgtgtgcagggataactggcatggctcgaatcgaccgtgggtgtctttcaaccagaatctg |
| 49 | H1N1 Neuraminidase conserved region (amino acid) | NGVWIGRTKS |
| 50 | H1N1 Neuraminidase conserved region (nucleic acid) | aatggtgtttggatagggagaactaaaagc |
| 51 | H1N1 Neuraminidase conserved region (amino acid) | GFEMIWDPNGWT |
| 52 | H1N1 Neuraminidase conserved region (nucleic acid) | ggttttgagatgatttgggatccgaatggatggact |
| 53 | H1N1 Neuraminidase | WSGYSGSFVQHPELTGL |

-continued

SEQUENCE LISTING TABLE

| SEQ ID NO | Description | Sequence |
|---|---|---|
| | conserved region (amino acid) | |
| 54 | H1N1 Neuraminidase conserved region (nucleic acid) | tggtcagggtatagcgggagttttgttcagcatcc agaactaacagggctg |
| 55 | H1N1 Neuraminidase conserved region (amino acid) | RPCFWVEL |
| 56 | H1N1 Neuraminidase conserved region (nucleic acid) | agaccttgcttctgggttgaacta |
| 57 | H1N1 Neuraminidase conserved region (amino acid) | WTSGSS1SFCGV |
| 58 | H1N1 Neuraminidase conserved region (nucleic acid) | tggactagcgggagcagcatatcctttttgtggtgta |
| 59 | H1N1 Neuraminidase conserved region (amino acid) | WSWPDGAELPF |
| 60 | H1N1 Neuraminidase conserved region (nucleic acid) | tggtcttggccagacggtgctgagttgccattt |
| 61 | H3N2 Hemagglutinin conserved region (amino acid) | LCLGHHA |
| 62 | H3N2 Hemagglutinin conserved region (nucleic acid) | ctgtgccttgggcaccatgcatta |
| 63 | H3N2 Hemagglutinin conserved | GNLIAPRGYF |

-continued

| SEQ ID NO | Description | Sequence |
|---|---|---|
| | region (amino acid) | |
| 64 | H3N2 Hemagglutinin conserved region (nucleic acid) | gggaatctaattgctcctaggggttacttc |
| 65 | H3N2 Hemagglutinin conserved region (amino acid) | LKLATGMRN |
| 66 | H3N2 Hemagglutinin conserved region (nucleic acid) | ctgaaattggcaacaggaatgcgaaat |
| 67 | H3N2 Hemagglutinin conserved region (amino acid) | FGAIAGFIENGWEG |
| 68 | H3N2 Hemagglutinin conserved region (nucleic acid) | tttggcgcaatagcaggtttcatagaaaatggttgggagggg |
| 69 | H3N2 Hemagglutinin conserved region (amino acid) | KFHQIEKEF |
| 70 | H3N2 Hemagglutinin conserved region (nucleic acid) | aaattccatcagattgaaaagaattc |
| 71 | H3N2 Hemagglutinin conserved region (amino acid) | DLTDSEM |
| 72 | H3N2 Hemagglutinin conserved region (nucleic acid) | gatctaactgactcagaaatg |
| 73 | H3N2 Hemagglutinin conserved region (amino acid) | LRENAED |

-continued

SEQUENCE LISTING TABLE

| SEQ ID NO | Description | Sequence |
|---|---|---|
| 74 | H3N2 Hemagglutinin conserved region (nucleic acid) | ctgagggaaaatgctgaggat |
| 75 | H3N2 Neuraminidase conserved region (amino acid) | QFALGQGTT |
| 76 | H3N2 Neuraminidase conserved region (nucleic acid) | caatttgcccttggacagggaacaaca |
| 77 | H3N2 Neuraminidase conserved region (amino acid) | AWSSSSC |
| 78 | H3N2 Neuraminidase conserved region (nucleic acid) | gcatggtccagctcaagttgt |
| 79 | H3N2 Neuraminidase conserved region (amino acid) | LRTQESEC |
| 80 | H3N2 Neuraminidase conserved region (nucleic acid) | ctcaggacccaggagtcagaatgc |
| 81 | H3N2 Neuraminidase conserved region (amino acid) | EECSCYP |
| 82 | H3N2 Neuraminidase conserved region (nucleic acid) | gaggagtgctcctgctatcct |
| 83 | H3N2 Neuraminidase conserved region (amino acid) | CSGLVGDTPR |
| 84 | H3N2 Neuraminidase | tgctcaggacttgttggagacacacccaga |

-continued

SEQUENCE LISTING TABLE

| SEQ ID NO | Description | Sequence |
|---|---|---|
| | conserved region (nucleic acid) | |
| 85 | H3N2 Neuraminidase conserved region (amino acid) | GVKGWAFD |
| 86 | H3N2 Neuraminidase conserved region (nucleic acid) | ggagtgaaaggctgggcctttgat |
| 87 | H3N2 Neuraminidase conserved region (amino acid) | NRCFYVELIRG |
| 88 | H3N2 Neuraminidase conserved region (nucleic acid) | aatcggtgcttttatgtggagttgataaggga |
| 89 | H3N2 Neuraminidase conserved region (amino acid) | VFCGTSGTYG |
| 90 | H3N2 Neuraminidase conserved region (nucleic acid) | gtgttttgtggcacctcaggtacatatgga |
| 91 | H3N2 Neuraminidase conserved region (amino acid) | GSWPDGA |
| 92 | H3N2 Neuraminidase conserved region (nucleic acid) | ggctcatggcctgatggggcg |
| 93 | Influenza B Hemagglutinin conserved region (amino acid) | VKTATQEVNVTG |
| 94 | Influenza B Hemagglutinin conserved region (nucleic | gtcaaaactgctactcaaggggaggtcaatgtgactggt |

-continued

| SEQ ID NO | Description | Sequence |
|---|---|---|
| | SEQUENCE LISTING TABLE | |
| | acid) | |
| 95 | Influenza B Hemagglutinin conserved region (amino acid) | NCTDLDVAL |
| 96 | Influenza B Hemagglutinin conserved region (nucleic acid) | aactgcacagatctggacgtagccttg |
| 97 | Influenza B Hemagglutinin conserved region (amino acid) | TSGCFPIMHDRTKIRQL |
| 98 | Influenza B Hemagglutinin conserved region (nucleic acid) | acatctgggtgctttcctataatgcacgac agaacaaaaattagacagctg |
| 99 | Influenza B Hemagglutinin conserved region (amino acid) | NLLRGYE |
| 100 | Influenza B Hemagglutinin conserved region (nucleic acid) | aaccttctccgaggatacgaa |
| 101 | Influenza B Hemagglutinin conserved region (amino acid) | TMAWAVP |
| 102 | Influenza B Hemagglutinin conserved region (nucleic acid) | acaatggcttgggccgtccca |
| 103 | Influenza B Hemagglutinin conserved region (amino acid) | EDGGLPQSGRIVVDYM |
| 104 | Influenza B Hemagglutinin conserved region (nucleic acid) | gaagacggaggactaccacaaagtggta gaattgttgttgattacatg |

SEQUENCE LISTING TABLE

| SEQ ID NO | Description | Sequence |
|---|---|---|
| 105 | Influenza B Hemagglutinin conserved region (amino acid) | LPLIGEADCLHE |
| 106 | Influenza B Hemagglutinin conserved region (nucleic acid) | ttgcctttaattggagaagcagattgcctccacgaa |
| 107 | Influenza B Hemagglutinin conserved region (amino acid) | YGGLNKSKPYYTG |
| 108 | Influenza B Hemagglutinin conserved region (nucleic acid) | tacggtggattaaacaaaagcaagccttactacacaggg |
| 109 | Influenza B Hemagglutinin conserved region (amino acid) | CPIWVKTPL |
| 110 | Influenza B Hemagglutinin conserved region (nucleic acid) | tgcccaatatgggtgaaaacacccttg |
| 111 | Influenza B Hemagglutinin conserved region (amino acid) | GFFGAIAGFLEGGWEGM |
| 112 | Influenza B Hemagglutinin conserved region (nucleic acid) | ggtttcttcggagctattgctggtttcttag aaggaggatgggaaggaatg |
| 113 | Influenza B Hemagglutinin conserved region (amino acid) | AGWHGYTSHGAHG |
| 114 | Influenza B Hemagglutinin conserved region (nucleic acid) | gcaggttggcacggatacacatcccatggggcacatgga |
| 115 | Influenza B Hemagglutinin | AVAADLKSTQEA |

-continued

SEQUENCE LISTING TABLE

| SEQ ID NO | Description | Sequence |
|---|---|---|
| | conserved region (amino acid) | |
| 116 | Influenza B Hemagglutinin conserved region (nucleic acid) | gcggtggcagcagaccttaagagcactcaagaggcc |
| 117 | Influenza B Hemagglutinin conserved region (amino acid) | KITKNLNSLSELE |
| 118 | Influenza B Hemagglutinin conserved region (nucleic acid) | aagataacaaaaaatctcaactctttgagtgagctggaa |
| 119 | Influenza B Hemagglutinin conserved region (amino acid) | KNLQRLS |
| 120 | Influenza B Hemagglutinin conserved region (nucleic acid) | aagaatcttcaaagactaagc |
| 121 | Influenza B Hemagglutinin conserved region (amino acid) | EILELDEKVDDLRADTISSQIELAVLLSNEGIINSED EHLLALERKLKKMLGPSA |
| 122 | Influenza B Hemagglutinin conserved region (nucleic acid) | gaaatactagaactagatgagaaagtggatga tctcagagctgatacaataagctcacaaatag aactcgcagtcctgctttccaatgaaggaata ataaacagtgaagatgaacatctcttggcgct tgaaagaaagctgaagaaaatgctgggcccct ctgct |
| 123 | Influenza B Hemagglutinin conserved region (amino acid) | IGNGCFETKHKCNQTCLD |
| 124 | Influenza B Hemagglutinin conserved region (nucleic acid) | atagggaatggatgctttgaaaccaaac acaagtgcaaccagacctgtctcgac |
| 125 | Influenza B Hemagglutinin conserved region | AGEFSLPTFDSLNITAASL |

-continued

SEQUENCE LISTING TABLE

| SEQ ID NO | Description | Sequence |
|---|---|---|
| | (amino acid) | |
| 126 | Influenza B Hemagglutinin conserved region (nucleic acid) | gcaggagaattttctctccccacctttg attcactgaatattactgctgcatcttta |
| 127 | Influenza B Hemagglutinin conserved region (amino acid) | HTILLYYSTAASSLAVTLM |
| 128 | Influenza B Hemagglutinin conserved region (nucleic acid) | catactatactgctttactactcaactgc tgcctccagtttggctgtaacactgatg |
| 129 | Influenza B Neuraminidase conserved region (amino acid) | ALLISPHRFGE |
| 130 | Influenza B Neuraminidase conserved region (nucleic acid) | gcactcctaattagccctcatagattcggagaa |
| 131 | Influenza B Neuraminidase conserved region (amino acid) | HFALTHYAAQPG |
| 132 | Influenza B Neuraminidase conserved region (nucleic acid) | cactttgctttaacccattatgcagcccaaccaggg |
| 133 | Influenza B Neuraminidase conserved region (amino acid) | DRNKLRHL |
| 134 | Influenza B Neuraminidase conserved region (nucleic acid) | gacagaaacaagctgaggcatcta |
| 135 | Influenza B Neuraminidase conserved region (amino acid) | AWSGSACHDG |

-continued

SEQUENCE LISTING TABLE

| SEQ ID NO | Description | Sequence |
|---|---|---|
| 136 | Influenza B Neuraminidase conserved region (nucleic acid) | gcatggagcgggtccgcgtgccatgatggt |
| 137 | Influenza B Neuraminidase conserved region (amino acid) | KYGEAYTDTYHSY |
| 138 | Influenza B Neuraminidase conserved region (nucleic acid) | aaatatggagaagcatatactgacacataccattcctat |
| 139 | Influenza B Neuraminidase conserved region (amino acid) | LRTQESACNCI |
| 140 | Influenza B Neuraminidase conserved region (nucleic acid) | ctaagaacacaagaaagtgcctgcaattgcatc |
| 141 | Influenza B Neuraminidase conserved region (amino acid) | CRFLKIREGR |
| 142 | Influenza B Neuraminidase conserved region (nucleic acid) | tgcagatttcttaagattcgagagggccga |
| 143 | Influenza B Neuraminidase conserved region (amino acid) | HTEECTCGFA |
| 144 | Influenza B Neuraminidase conserved region (nucleic acid) | cacactgaggaatgcacatgcggatttgcc |
| 145 | Influenza B Neuraminidase conserved region (amino acid) | YTAKRPFVKL |
| 146 | Influenza B Neuraminidase conserved | tacacagcaaaaagacctttgtcaaatta |

-continued

| SEQ ID NO | Description | Sequence |
|---|---|---|
| | region (nucleic acid) | |
| 147 | Influenza B Neuraminidase conserved region (amino acid) | KGGFVHQR |
| 148 | Influenza B Neuraminidase conserved region (nucleic acid) | aagggaggatttgttcatcaaaga |
| 149 | Influenza B Neuraminidase conserved region (amino acid) | GRWYSRT |
| 150 | Influenza B Neuraminidase conserved region (nucleic acid) | ggaaggtggtactctcgaacg |
| 151 | Influenza B Neuraminidase conserved region (amino acid) | EPGWYSFGFE |
| 152 | Influenza B Neuraminidase conserved region (nucleic acid) | gaacctggttggtattcctttggcttcgaa |
| 153 | Influenza B Neuraminidase conserved region (amino acid) | EMVHDGG |
| 154 | Influenza B Neuraminidase conserved region (nucleic acid) | gagatggtacatgatggtgga |
| 155 | H1N1 Neuraminidase conserved region (amino acid) | GAVAVLKY |
| 156 | H1N1 Neuraminidase conserved region (nucleic acid) | ggggcagtggctgtgttaaagtac |

-continued

SEQUENCE LISTING TABLE

| SEQ ID NO | Description | Sequence |
|---|---|---|
| 157 | Variant of H1N1 Hemagglutinin A/Michigan/45/ 2015 strain (amino acid) GenBank: MK622940.1 Hypervariable residues substituted with Ala | MKAILVVLLYTFAAANADTLCIGYH ANNSTDTVDTVLEKNVTVTHSVNLL EAAHNGKLCKLRGVAPLHLGKCNIA GWALGNPECEALATASSWSYIVETS ASDNGTCYPGDFIAYEELREQLSSV SSFERFEIFPKASSWPNHDANAGVT AACPAAGAAAFYANLIWLVKKGNSY PKAAASYINAKAKEVLVLWAIHHPA TAADQQSLYQNADAYVFVGASAYSA KFAPEIAARPKVRAQAGRMNYYWTL AEPGDAITFEATGNLVVPRYAFAAA RAAGSGIIISDAAVHDCATTCQTPA GAINTSLPFQNIHPATIGACPKYVK STKLRAATGLRNAPSIQSRGLFGAI AGFIEGGWTGMADGWYGYHHQNEQG SGYAADAKSTQNAIDAITNKVNSVI EKMNTQFTAVGKEFAHLEARIENLN KKVDDGFLDIWTYNAELLVLLENER TLDYHDSNVKNLYEKVRAQLKNNAK EIGNGCFEFYHKCDAACMESVKNGT YDYPKYSEEAKLNREAIDGVKLEST RIYQILAIYSTVASSLVLAVSLGAI SFWMCSNGSLQCRICI* |
| 158 | Influenza A H1N1 Hemagglutinin 2009 residues 145-229 | SNKGVTAACPHAGAKSFYKNLIWLVKKGNSYPKLSKSYIN DKGKEVLVLWGIHHPSTSADQQSLYQNADAYVFVGSSRYS KKFKP |
| 159 | Influenza A H1N1 Hemagglutinin 2010 residues 145-229 | SNKGVTAACPHAGAKSFYKNLIWLVKKGNSYPKLSKSYIN DKGKEVLVLWGIHHPPTSADQQSLYQNADAYVFVGTSRYS KKFKP |
| 160 | Influenza A H1N1 Hemagglutinin 2011 residues 145-229 | TTRGTTVACSHSGANSFYRNLLWIVKKGNSYPKLSKSYTNN KGKEVLVIWGVHHPPTDSDQQTLYQNNHTYVSVGSSKYYK RLTP |
| 161 | Influenza A H1N1 Hemagglutinin 2012 residues 145-229 | SNKGVTAACPHAGAKGFYKNLIWLVKKGNSYPKLSKSYIN DKGKEVLVLWGIHHPSTTADQQSLYQNADTYWVGTSRYS KKFKP |
| 162 | Influenza A H1N1 Hemagglutinin 2013 residues 145-229 | SNKGVTAACPHAGAKSFYKNLIWLVKKGNSYPKLSKSYIN DKGKEVLVLWGIHHPSTTADQQSLYQNANAYVFVGTSKYS KKFKP |
| 163 | Influenza A H1N1 Hemagglutinin 2014 residues 145-229 | SNKGVTAACPHAGAKSFYKNLIWLVKKGNSYPKLSKSYIN DKGKEVLVLWGIHHPSTSADQQSLYQNADAYVFVGTSRYS KKFKP |
| 164 | Influenza A H1N1 Hemagglutinin 2015 residues 145-229 | SNKGVTAACPHAGAKSFYKNLIWLVKKGNSYPKLSKSYIN DKGKEVLVLWGIHHPSTSADQQSLYQNADAYWVGTSRYS KKFKP |
| 165 | Influenza A H1N1 Hemagglutinin 2016 residues 145-229 | SNKGVTAACPHAGAKSFYKNLIWLVKKGNSYPKLNQSYIN DKGKEVLVLWGIHHPSTTADQQSLYQNADAYVFVGTSRYS KKFKP |

-continued

SEQUENCE LISTING TABLE

| SEQ ID NO | Description | Sequence |
|---|---|---|
| 166 | Influenza A H1N1 Hemagglutinin 2017 residues 145-229 | SNKGVTAACPHAGAKSFYKNLIWLVKKGNSYPKLNQTYIN DKGKEVLVLWGIHHPPTTADQQSLYQNADAYVFVGTSRYS KKFKP |
| 167 | Influenza A H1N1 Hemagglutinin 2018 residues 145-229 | SDKGVTAACPHAGAKSFYKNLIWLVKKGNSYPKLNQTYIN DKGKEVLVLWGIHHPPTIADQQSLYQNADAYVFVGTSRYS KKFKP |
| 168 | Influenza A H1N1 Hemagglutinin 2019 residues 145-229 | SNKGVTAACPHAGAKSFYKNLIWLVKKGNSYPKINQTYIND KGKEVLVLWGIHHPPTTADQQSLYQNADAYVFVGTSRYSK KFKP |
| 169 | H1N1 Hemagglutinin A/Michigan/ 45/2015 strain (nucleotide) GenBank: MK622940.1 | atgaaggcaatactagtagttctgctatat acatttacaaccgcaaatgcagacacatta tgtataggttatcatgcgaacaattcaaca gacactgtagacacagtactagaaaagaat gtaacagtaacacactctgttaaccttctg gaagacaagcataacggaaaactatgcaaa ctaagaggggtagccccattgcatttgggt aaatgtaacattgctggctggatcctggga aatccagagtgtgaatcrctctccacagca agttcatggtcctacattgtgaaacatct aattcagacaatggaacgtgttacccagga gatttcatcaattatgaggagctaagagag caattgagctcagtgtcatcatttgaaagg tttgagatattccccaagacaagttcatgg cccaatcatgactcgaacaaaggtgtaacg gcagcatgtcctcacgctggagcaaaaagc ttctacaaaaacttgatatggctagttaaa aaaggaaattcatacccaaagcttaaccaa tcctacattaatgataaagggaaagaagtc ctcgtgctgtggggcattcaccatccatct actactgctgaccaaaagtctctatcag aatgcagatgcatatgttttgtggggaca tcaagatacagcaagaagttcaagccggaa atagcaacaagacccaaagtgagggatcaa gaagggagaatgaactattactggacacta gtagagccgggagacaaaataacattcgaa gcaactggaaatctagtggtaccgagatat gcattcacaatggaaagaaatgctggatct ggtattatcatttcagatacaccagtccac gattgcaatacaacttgtcagacacccgag ggtgctataaacaccagcctcccatttcag aatatacatccgatcacaattggaaaatgt ccaaagtatgtaaaaagcacaaaattgaga ctggccacaggattgaggaatgttccgtct attcaatctagaggcctattcggggccatt gccggcttcattgaagggggtggacaggg atggtagatggatggtacggttatcaccat caaaatgagcagggtcaggatatgcagcc gacctgaagagcacacaaaatgccattgac aagattactaacaaagtaaattctgttatt gaaaagatgaatacacagttcacagcagtg ggtaaagagttcaaccacctggaaaaaaga atagagaatctaaataaaaaagttgatgat ggtttcctggacatttggacttacaatgcc gaactgttggttctattggaaaatgaaaga actttggactatcacgattcaaatgtgaag aacttgtatgaaaaagtaagaaaccagtta aaaaacaatgccaaggaaattggaaacggc tgctttgaattttaccacaaatgcgataac acgtgcatggaaagtgtcaaaaatgggact tatgactacccaaaatactcagaggaagca aaattaaacagagaaaaaatagatgggta aagctggaatcaacaaggatttaccagatt ttggcgatctattcaactgtcgccagttca ttggtactggtagtctccctgggggcaatc |

SEQUENCE LISTING TABLE

| SEQ ID NO | Description | Sequence |
|---|---|---|
| | | agcttctggatgtgctctaatgggtctcta cagtgtagaatatgtatttaa |
| 170 | Variant of H1N1 Hemagglutinin A/Michigan/ 45/2015 strain (nucleotide) GenBank: MK622940.1 Hypervariable residues substituted with Ala | atgaaggcaatactagtagttctgctatat acatttgcagccgcaaatgcagacacatta tgtataggttatcatgcgaacaattcaaca gacactgtagacacagtactagaaaagaat gtaacagtaacacactctgttaaccttctg gaagccgcgcataacggaaaactatgcaaa ctaagaggggtagccccattgcatttgggt aaatgtaacattgctggctgggccctggga aatccagagtgtgaagcrctcgccacagca agttcatggtcctacattgtggaaacatct gcttcagacaatggaacgtgttacccagga gatttcatcgcttatgaggagctaagagag caattgagctcagtgtcatcatttgaaagg tttgagatattccccaaggcaagttcatgg cccaatcatgacgcgaacgcaggtgtaacg gcagcatgtcctgccgctggagcagcagcc ttctacgcaaacttgatatggctagttaaa aaaggaaattcatacccaaaggctgccgca tcctacattaatgctaaagcgaaagaagtc ctcgtgctgtgggccattcaccatccagct actgctgctgaccaacaaagtctctatcag aatgcagatgcatatgtttttgtggggaca tcagcatacagcgcgaagttcgcgccggaa atagcagcaagacccaaagtgagggctcaa gcaggagaatgaactattactggacacta gcagagccgggagacgcaataacattcgaa gcaactggaaatctagtggtaccgagatat gcattcgcagcggcaagagctgctggatct ggtattatcatttcagatgcagcagtccac gattgcgctacaacttgtcagacacccgcg ggtgctataaacaccagcctcccatttcag aatatacatccggccacaattggagcatgt ccaaagtatgtaaaaagcacaaaattgaga gcggccacaggattgaggaatgctccgtct attcaatctagaggcctattcggggccatt gccggcttcattgaagggggtggacaggg atggcagatggatggtacggttatcaccat caaaatgagcagggtcaggatatgcagcc gacgcgaagagcacacaaaatgccattgac gcgattactaacaaagtaaattctgttatt gaaaagatgaatacacagttcacagcagtg ggtaaagagttcgcccacctggaagcaaga atagaaatctaaataaaaaagttgatgat ggtttcctggacatttggacttacaatgcc gaactgttggttctattggaaaatgaaaga actttggactatcacgattcaaatgtgaag aacttgtatgaaaaagtaagagcccagtta aaaaacaatgccaaggaaattggaaacggc tgctttgaattttaccacaaatgcgatgcc gcgtgcatggaaagtgtcaaaaatgggact tatgactacccaaaatactcagaggaagca aaattaaacagagaagcaatagatggggta aagctggaatcaacaaggatttaccagatt ttggcgatctattcaactgtcgccagttca ttggtactggcagtctccctggggcaatc agcttctggatgtgctctaatgggtctcta cagtgtagaatatgtatttaa |
| 171 | H3N2 M1 Protein | <u>MSLLTEVETYVLSIVPSGPLKAEIAQRLE</u>D<u>VFAGKNTDLEAL</u><br><u>MEWLKTRPILSPLTKGILGFVFTLTVPSERGLQRRRFVQNAL</u><br><u>NGNGDPNNMDKAVKLYRKLKREITFHGAKE</u>IALSYSAGAL<br>ASCMGLIYNRMGAVTTEVAFGLVCATCEQIADSQHRSHRQ<br>MVATTNPLIKHENRMVLASTTAKAMEQMAGSSEQAAEAM<br>EIASQARQMVQAMRAIGTHPSSSTGLRDDLLENLQTYQKR<br>MGVQMQRFK<br>(underline = highly conserved; bold = hypervariable) |
| 172 | H3N2 NEP Protein | MDSNTV<u>SSFQDILLRMSK</u>MQ<u>LGSSSEDLNGMITQFESLKIY</u><br>RDSLGEA<u>VMRMGDLHLL</u>QNRNGKWREQLGQKFEEIRWLIE |

-continued

| SEQ ID NO | Description | Sequence |
|---|---|---|
| | | EVRHRLRTTENSFEQITFMQALQLLFEVEQEIRTFSFQLI<br>(underline = highly conserved;<br>bold = hypervariable) |
| 173 | H3N2 NP Protein | MASQGTKRSYEQMETDGDRQNATEIRASVGKMIDGIGRFYI<br>QMCTELKLSDHEGRLIQNSLTIEKMVLSAFDERRNKYLEEH<br>PSAGKDPKKTGGPIYRRVDGKWMRELVLYDKEEIRRIWRQ<br>ANNGEDATSGLTHIMIWHSNLNDATYQRTRALVRTGMDPR<br>MCSLMQGSTLPRRSGAAGAAVKGIGTMVMELIRMVKRGIN<br>DRNFWRGENGRKTRSAYERMCNILKGKFQTAAQRAMVDQ<br>VRESRNPGNAEIEDLIFLARSALILRGSVAHKSCLPACAYGP<br>AVSSGYDFEKEGYSLVGIDPFKLLQNSQIYSLIRPNENPAHK<br>SQLVWMACHSAAFEDLRLLSFIRGTKVSPRGKLSTRGVQIA<br>SNENMDNMGSSTLELRSGYWAIRTRSGGNTNQQRASAGQ<br>TSVQPTFSVQRNLPFEKSTIMAAFTGNTEGRTSDMRAEIIR<br>MMEGAKPEEVSFRGRGVFELSDEKATNPIVPSFDMSNEGSY<br>FFGDNAEEYDN<br>(underline = highly conserved;<br>bold = hypervariable) |
| 174 | H3N2 NS1 Protein | MDSNTVSSFQVDCFLWHIRKQVVDQKLSDAPFLDRLRRDQ<br>RSLRGRGNTLGLDIKAATHVGKQIVEKILKEESDEALKMT<br>MVSTPASRYITDMTIEELSRNWFMLMPKQKVEGPLCIRMD<br>QAIMEKNIMLKANFNVIFGRLETIVLLRAFTEEGAIVGEISPL<br>PSFPGHTIEDVKNAIGVLIGGLEWNDNTVRVSKNLQRFAWR<br>SSNENGGPPLTPK<br>(underline = highly conserved;<br>bold = hypervariable) |
| 175 | H3N2 NS2 Protein | MDSNTVSSFQDILLRMSKMQLGSSSEDLNGMITQFESLKIYR<br>DSLGEAVMRMGDLHLLQNRNGKWREQLGQKFEEIRWLIEE<br>VRHRLKTTENSFEQITFMQALQLLFEVEQEIRTFSFQLI<br>(underline = highly conserved;<br>bold = hypervariable) |
| 176 | H3N2 PA Protein | MEDFVRQCFNPMIVELAEKAMKEYGEDLKIETNKFAAICTH<br>LEVCFMYSDFHFINEQGESIVVELDDPNALLKHRFEIIEGRD<br>RTMAWTVVNSICNTTGAGKPKFLPDLYDYKENRFIEIGVTR<br>REVHIYYLEKANKIKSENTHIHIFSFTGEEMATKADYTLDEE<br>SRARIKTRLFTIRQEMANRGLWDSFRQSERGEETIEEKFEITG<br>TMRRLADQSLPPNFSCLENFRAYVDGFEPNGCIEGKLSQMS<br>KEVNAQIEPFLKTTPRPIKLPSGPPCYQRSKFLLMDALKLSIE<br>DPSHEGEGIPLYDAIKCIKTFFGWKEPYIVKPHEKGINSNYLL<br>SWKQVLSELQDIENEEKIPRTKNMKKTSQLKWALGENMAP<br>EKVDFENCRDISDLKQYDSEEPELRSLSSWIQSEFNKACELT<br>DSVWIELDEIGEDVAPIEHIASMRRNYFTAEVSHCRATEYIM<br>KGVYINTALLNASCAAMDDFQLIPMISKCRTKEGRRKTNLY<br>GFIIKGRSHLRNDTDVVNFVSMEFSLTDPRLEPHKWEKYCV<br>LEIGDMLLRSAIGQISRPMFLYVRTNGTSKVKMKWGMEMR<br>RCLLQSLQQIESMIEAESSVKEKDMTKEFFENKSEAWPIGES<br>PKGVEEGSIGKVCRTLLAKSVFNSLYASPQLEGFSAESRKLL<br>LIVQALRDKLEPGTFDLGGLYEAIEECLINDPWVLLNASWF<br>NSFLTHALK<br>(underline = highly conserved;<br>bold = hypervariable) |
| 177 | H3N2 PA-X Protein | MEDFVRQCFNPMIVELAEKAMKEYGEDLKIETNKFAAICTH<br>LEVCFMYSDFHFINEQGESIVVELDDPNALLKHRFEIIEGRD<br>RTMAWTVVNSICNTTGAGKPKFLPDLYDYKENRFIEIGVTR<br>REVHIYYLEKANKIKSENTHIHIFSFTGEEMATKADYTLDEE<br>SRARIKTRLFTIRQEMANRGLWDSFVSPKEAKKQLKKNLKS<br>QELCAGLPTKVSHRTSPALRILEPMWMDSNRTAALRASFLK<br>CPKK<br>(underline = highly conserved;<br>bold = hypervariable) |
| 178 | H3N2 PB1 Protein | MDVNPTLLFLKVPAQNAISTTFPYTGDPPYSHGTGTGYTMD<br>TVNRTHQYSERGKWTTNTETGAPQLNPIDGPLPEDNEPSGY<br>AQTDCVLEAMAFLEESHPGIFENSCLETMEAVQQTRVDKLT<br>QGRQTYDWTLNRNQPAATALANTIEVFRSNGLTANESGRLI<br>DFLKDVMESMDKEEMEITTHFQRKRRVRDNMTKKMVTQR<br>TIGKKKQRVNKRGYLIRALTLNTMTKDAERGKLKRRAIATP<br>GMQIRGFVYFVETLARSICEKLEQSGLPVGGNEKKAKLANV |

SEQUENCE LISTING TABLE

| SEQ ID NO | Description | Sequence |
|---|---|---|
| | | VRKMMTNSQDTELSFTITGDNTKWNENQNPRMFLAMITYIT<br>KNQPEWFRNILSIAPIMFSNKMARLGKGYMFESKRMKLRT<br>QIPAEMLASIDLKYFNESTRKKIEKIRPLLIDGTASLSPGMM<br>MGMFNMLSTVLGVSILNLGQKKYTKTTYWWDGLQSSDDF<br>ALIVNAPNHEGIQAGVDRFYRTCKLVGINMSKKKSYINKTG<br>TFEFTSFFYRYGFVANFSMELPSFGVSGINESADMSIGVTVIK<br>NNMIINNDLGPATAQMALQLFIKDYRYTYRCHRGDTQIQTR<br>RSFEIKKLWDQTQSRTGLLVSDGGPNLYNIRNLHIPEVCLK<br>WELMDENYRGRLCNPLNPFVSHKEIESVNNAVVMPAHGPA<br>KSMEYDAVATTHSWIPKRNRSILNTSQRGILEDEQMYQKCC<br>NLFEKFFPSSSYRRPIGISSMVEAMVSRARIDARIDFESGRIK<br>KEEFSEIMKICSTIEELRRQK<br>(underline = highly conserved;<br>bold = hypervariable) |
| 179 | H3N2 PB2 Protein | MERIKELRNLMSQSRTREILTKTTVDHMAIIKKYTSGRQEKN<br>PSLRMKWMMAMKYPITADKRITEMVPERNEQGQTLWSK<br>MSDAGSDRVMVSPLAVTWWNRNGPVTSTVHYPKVYKTYF<br>DKVERLKHGTFGPVHFRNQVKIRRRVDINPGHADLSAKEA<br>QDVIMEVVFPNEVGARILTSESQLTITKEKKEELRDCKISPL<br>MVAYMLERELVRKTRFLPVAGGTSSIYIEVLHLTQGTCWEQ<br>MYTPGGGVRNDDVDQSLIIAARNIVRRAAVSADPLASLLEM<br>CHSTQIGGTRMVDILRQNPTEEQAVDICKAAMGLRISSSFSF<br>GGFTFKRTSGSSVKKEEEVLTGNLQTLRIRVHEGYEEFTMV<br>GKRATAILRKATRRLVQLIVSGRDEQSIAEAIIVAMVFSQED<br>CMIKAVRGDLNFVNRANQRLNPMHQLLRHFQKDAKVLFQ<br>NWGVEHIDSVMGMVGVLPDMTPSTEMSRGIRVSKMGVD<br>EYSSTERVVVSIDRFLRVRDQRGNVLLSPEEVSETQGTERLT<br>ITYSSSMMWEINGPESVLVNTYQWIIRNWEAVKIQWSQNPA<br>MLYNKMEFEPFQSLVPKATRSQYSGFVRTLFQQMRDVLGT<br>FDTAQIIKLLPFAAAPPKQSRMQFSSLTVNVRGSGMRILVRG<br>NSPVFNYNKTTKRLTILGKDAGTLIEDPDESTSGVESAVLRG<br>FLIIGKEDRRYGPALSINELSNLAKGEKANVLIGQGDVVLV<br>MKRKRDSSILTDSQTATKRIRMAIN<br>(underline = highly conserved;<br>bold = hypervariable |
| 180 | Influenza B bm2 Protein | MLEPFQILSICSFILSALHFMAWTIGHLNQIKRGVNMKIRIKG<br>PNKETINREVSILRHSYQKEIQAKEAMKEVLSDNMEVLSDHI<br>VIEGLSAEEIIKMGETVLEVEELH<br>(underline = highly conserved;<br>bold = hypervariable) |
| 181 | Influenza B bm1 Protein | MSLFGDTIAYLLSLTEDGEGKAELAEKLHCWFGGKEFDLDS<br>ALEWIKNKRCLTDIQKALIGASICFLKPKDQERKRRFITEPLS<br>GMGTTATKKKGLILAERKMRKCVSFHEAFEIAEGHESSALL<br>YCLMVMYLNPGNYSMQVKLGTLCALCEKQASHSHRAHSR<br>AARSSVPGVRREMQMVSAMNTAKTMNGMGKGEDVQKLA<br>EELQSNIGVLRSLGASQKNGEGIAKDVMEVLKQSSMGNSAL<br>VKKYL<br>(underline = highly conserved;<br>bold = hypervariable) |
| 182 | Influenza B nep Protein | MADNMTTTQIEWRMKKMAIGSSIHSSSVLMKDIQSQFEQL<br>KLRWESYPNLVKSTDYHQKRETIRLVTEELYLLSKRIDDNIL<br>FHKTVIANSSIIADMVVSLSLLETLYEMKDVVEVYSRQCL<br>(underline = highly conserved;<br>bold = hypervariable) |
| 183 | Influenza B ns1 Protein | MADNMTTTQIEVGPGATNATINFEAGILECYERLSWQRALD<br>YPGQDRLNRLKRKLESRIKTHNKSEPESKRMSLEERKAIGV<br>KMMKVLLFMNPSAGIEGFEPYCMKSSSNSNCPKYNWTDYP<br>STPGRCLDDIEEEPDDVDGPTEIVLRDMNNKDARQKIKEEV<br>NTQKEGKFRLTIKRDMRNVLSLRVLVNGTFLKHPNGYKSLS<br>TLHRLNAYDQSGRLVAKLVATDDLTVEDEEDGHRILNSLFE<br>RLNEGHSKPIRAAETAVGVLSQFGQEHRLSPEEGDN<br>(underline = highly conserved;<br>bold = hypervariable) |

| SEQ ID NO | Description | Sequence |
|---|---|---|
| 184 | Influenza B ns2 Protein | MADNMTTTQIEVVRMKKMAIGSSTHSSSVLM<u>KDIQSQFEQL</u> <u>KLRWESYPNLVKSTDYHQKRETIRLVTEELYLLSKRIDDNIL</u> <u>FHKTVIANSSIIADM</u>VVS<u>LSLLETLYEMKDVVEVYSRQCL</u> (underline = highly conserved; bold = hypervariable) |
| 185 | Influenza B pa Protein | <u>MDTFITRNFQTTIIQKAKNTMAEFSEDPELQPAMLFNICVHL</u> <u>EVCYVI</u>S<u>DMNFLDEEGKAYTALEGQGKEQNLRPQYEVIEG</u> <u>MPRTIAVVMVQRSLAQEHGIETPKYLADLFDYKTKRFIEVGI</u> <u>TKGLADDYFWKKKEKLGNSMELMIFSYNQDYSLSNESSLD</u> <u>EEGKGRVLSRLTELQAELSLKNLWQVLIGEEDVEKGIDF</u>KL <u>GQTISRLRDISVPAGFSNFEGMRSYIDNIDPKGAIERNLARMS</u> <u>PLVSVTPKKL</u>K<u>WEDLRPIGPHIY</u>N<u>HELPEVPYNAFLLMSDEL</u> <u>GLANMTEGKSKKPKTLAKECLEKYSTLRDQTDPILI</u>M<u>KSEK</u> <u>ANENFLWKLWRDCVNTISNEE</u>M<u>SNELQKTNYAKWATGDG</u> <u>LTYQKIMKEVAIDDETMCQEEPKIPNKCRVAAWVQTEMNL</u> <u>LSTLTSKRALDLPEIGPD</u>V<u>APVEHVGSERRKYFVNEINYCKA</u> <u>STVMMKYVLFHTSLLNESNASMGKYKVIPITNRV</u>V<u>NEKGES</u> <u>FDMLYGLAVKGQSHLRGDTDVVTVVTFEFSSTDPRVD</u>S<u>GK</u> <u>WPKYTVFRIGSLFV</u>S<u>GREKSVYLYCRVNGTNKIQMKWGME</u> <u>ARRCLLQSMQQMEAIVEQESSIQGYDMTKACFKGDRVNSP</u> <u>KTFSIGTQEGKLVKGSFGKALRVIFTKCLMHYVFGNAQLEG</u> <u>FSAESRRLLLLIQALKDRKGPWVFDLEGMYSGIEECISNNPW</u> <u>VIQSAYWFNEWLGFEKEGSKVLESVDEIMDE</u> (underline = highly conserved; bold = hypervariable) |
| 186 | Influenza B pb1 Protein | <u>MNINPYFLFIDVP</u>I<u>QAAISTTFPYTGVPPYSHGTGTGY</u>T<u>IDTVI</u> <u>RTHEYSNKGKQY</u>V<u>SDITGCTM</u>V<u>DPTNGPLPEDNEPSAYAQL</u> <u>DCVLEALDRMDEEHPGLFQAASQNAMEALMVTTVDKLTQ</u> <u>GRQTFDWTVCRNQPAATALNTTITSFRLNDLNGADKGGL</u>V <u>PFCQDIIDSLD</u>K<u>PEMTFFSVKNIKKKLPAKNRKGFLIKRIPMK</u> V<u>KDRISRVEYIKRALSLNTMTKDAERGKLKRRAIATAGIQIR</u> <u>GFVLVVENLAKNICENLEQSGLPVGGNEKKAKLSNAVAKM</u> <u>LSNCPPGGISMTVTGDNTKWNECLNPRIFLAMTERITRDSP</u>I <u>WFRDFCSIAPVLFSNKIARLGKGFM</u>I<u>TSKTKRLKAQIPCPDLF</u> <u>SIPLERYNEETRAKL</u>KK<u>LKPFFNEEGTASLSPGMMMGMFN</u> <u>MLSTVLGVAALGIKNIGNKEYLWDGLQSSDDFALFVNAKD</u> <u>EETCMEGINDFYRTCKLLGINMSKKKSYCNETGMFEFTSMF</u> <u>YRDGFVSNFAMEIPSFGVAGVNESADMAIGMTIIKNNMINN</u> <u>GMGPATAQTAIQLFIADYRYTYKCHRGDSKVEGKRMKIIKE</u> <u>LWENTKGRDGLLVADGGPNIYNLRNLHIPEIVLKYNLMDPE</u> <u>YKGRLLHPQNPFVGHLSIEGIKEADITPAHGPVKKMDYDAV</u> <u>SGTHSWRTKRNRSILNTDQRNMIEEEQCYAKCCNLFEACFN</u> <u>SASYRKPVGQHSMLEAMAHRLRMDARLDYESGRMSKDDF</u> <u>EKAMAHLGEIGYT</u> (underline = highly conserved; bold = hypervariable) |
| 187 | Influenza B pb2 Protein | <u>MTLAKIELLKQLLRDNEAKTVLKQTTVDQYNIIRKFNTSRIE</u> <u>KNPSLRMKWAMCSNFPLALTKGDMANRIPLEYKGIQLKTN</u> <u>AEDIGTKGQMCSIAAVTWWNTYGPIGDTEGFE</u>K<u>VYESFFLR</u> <u>KMRLDNATWGRITFGPVERVRKRVLLNPLTKEMPPDEASN</u> <u>VIMEILFPKEAGIPRESTWIHRELIKEKREKLKGTMITPIVLAY</u> <u>MLERELVARRRFLPVAGATSAEFIEMLHCLQGENWRQIYHP</u> <u>GGNKLTESRSQSMIVACRKIIRRSIVASNPLELAVEIANKTVI</u> <u>DTEPLKSCL</u>T<u>AIDGGDVACDIIRAALGLKIRQRQRFGRLELK</u> <u>RISGRGFKNDEEILIGNGTI</u>Q<u>KIGIWDGEEEFHVRCGECRGIL</u> <u>KKSKMM</u>RM<u>EKLLINSAKKEDM</u>K<u>DLIILCMVFSQDTRMFQGV</u> <u>RGEINFLNRAGQLLSPMYQLQRYFL</u>S<u>RSNDLFDQWGYEESP</u> <u>KASELHGINE</u>L<u>MNASDYTLKGVVVT</u>K<u>NVIDDFSSTETEKVS</u> <u>ITKNLSLIKRTGEVIMGANDVSELESQAQLMITYDTPKMWE</u> <u>MGTTKELVQNTYQWV</u>L<u>KNLVTEKAQFLLGKEDMFQWDAF</u> <u>EAFESIIPQKMAGQYSGFARAVLKQMRDQEVMKTDQFIKLL</u> <u>PFCFSPPPKLRSNGEPYQFLRLVLKGGGENFIEVRKGSPLFSY</u> <u>NPQTEVLTICGRMMSLKGKIEDEERNRSMGNAVLAGFLVSG</u> <u>KYDPDLGDFKTIEELEKLKPGEKANILLYQGKPVKVVKRKR</u> <u>YSALSNDISQGIKRQRMTVESMGWALS</u> (underline = highly conserved; bold = hypervariable) |

-continued

SEQUENCE LISTING TABLE

| SEQ ID NO | Description | Sequence |
|---|---|---|
| 188 | H1N1 M Protein | MSLLTEVETYVLSIIPSGPLKAEIAQRLESVFAGKNTDLEAL<br>MEWLKTRPILSPLTKGILGFVFTLTVPSERGLQRRRFIQNAL<br>NGNGDPNNMDRAVKLYKKLKREITFHGAKEVSLSYSTGAL<br>ASCMGLIYNRMGTVTTEAAFGLVCATCEQIADSQHRSHRQ<br>MATTTNPLIRHENRMVLASTTAKAMEQVAGSSEQAAEAME<br>VANQTRQMVHAMRTIGTHPSSSAGLRDDLLENLQAYQKR<br>MGVQMQRFK<br>(underline = highly conserved;<br>bold = hypervariable) |
| 189 | H1N1 ns1 Protein | MDSNTMSSFQVDCFLWHIRKRFADNGLGDAPFLDRLRRDQ<br>KSLKGRGNTLGLDIETATLVGKQIVEWILKEESSETLRMTI<br>ASVPTSRYLSDMTLEEMSRDWFMLMPRQKIIGPLCVRLDQ<br>AIMEKNIVLKANFSVIFNRLETLILLRAFTEEGAIVGEISP<br>LPSLPGHTYEDVKNAVGVLIGGLEWNGNTVRVSENIQRFA<br>WRNCDENGRPSLPPEQK<br>(underline = highly conserved;<br>bold = hypervariable) |
| 190 | H1N1 pa Protein | MEGFVRQCFNPMIVELAEKAMKEYGEDPKIETNKFAAICTH<br>LEVCFMYSDFHFIDERGESIIVESGDPNALLKHRFEIIEGRDRI<br>MAWTVVNSICNTTGVEKPKFLPDLYDYKENRFIEIGVTRRE<br>VHIYYLEKANKIKSEKTHIHIFSFTGEEMATKADYTLDEESR<br>ARIKTRLFTIRQEMASRSLWDSFRQSERGEETIEEKFEITGTM<br>RKLADQSLPPNFSSLENFRAYVDGFEPNGCIEGKLSQMSKE<br>VNAKIEPFLRTTPRPLRLPDGPLCHQRSKFLLMDALKLSIED<br>PSHEGEGIPLYDAIKCMKTFFGWKEPNIVKPHEKGINPNYL<br>MTWKQVLAELQDIENEEKIPRTKNMKRTSQLKWALGENM<br>APEKVDFDDCKDVGDLKQYDSDEPEPRSLASWVQNEFNKA<br>CELTDSSWIELDEIGEDVAPIEHIASMRRNYFTAEVSHCRAT<br>EYIMKGVYINTALLNASCAAMDDFQLIPMISKCRTKEGRRK<br>TNLYGFIIKGRSHLRNDTDVVNFVSMEFSLTDPRLEPHKWE<br>KYCVLEIGDMLLRTAIGQVSRPMFLYVRTNGTSKIKMKWG<br>MEMRRCLLQSLQQIESMIEAESSVKEKDMTKEFFENKSETW<br>PIGESPRGVEEGSIGKVCRTLLAKSVFNSLYASPQLEGFSAES<br>RKLLLIVQALRDNLEPGTFDLGGLYEAIEECLINDPWVLLNA<br>SWFNSFLTHALK<br>(underline = highly conserved;<br>bold = hypervariable) |
| 191 | H1N1 pb1 Protein | MDVNPTLLFLKIPAQNAISTTFPYTGDPPYSHGTGTGYTMDT<br>VNRTHQYSEKGKWTTNTETGAPQLNPIDGPLPEDNEPSGYA<br>QTDCVLEAMAFLEESHPGIFENSCLETMEVVQQTRVDKLTQ<br>GRQTYDWTLNRNQPAATALANTIEVFRSNGLTANESGRLID<br>FLKDVMESMNKEEIEITTHFQRKRRVRDNMTKKMVTQRTI<br>GKKKQRLNKRGYLIRALTLNTMTKDAHRGKLKRRAIATPG<br>MQIRGFVYFVETLARSICEKLEQSGLPVGGNEKKAKLANVV<br>RKMMTNSQDTEISFTITGDNTKWNENQNPRMFLAMITYITR<br>NQPEWFRNILSMAPIMFSNKMARLGRGYMFESKRMKIRTQI<br>PAEMLASIDLKYFNESTKKKIEKIRPLLIDGTASLSPGMMMG<br>MFNMLSTVLGVSILNLGQKKYTKTIYWWDGLQSSDDFALI<br>VNAPNHEGIQAGVDRFYRTCKLVGINMSKKKSYINKTGTFE<br>FTSFFYRYGFVANFSMELPSFGVSGVNESADMSIGVTVIKNN<br>MINNDLGPATAQMALQLFIKDYRYTYRCHRGDTQIQTRRSF<br>ELKKLWDQTQSKVGLLVSDGGPNLYNIRNLHIPEVCLKWEL<br>MDDDYRGRLCNPLNPFVSHKEIDSVNNAVVMPAHGPAKSM<br>EYDAVATTHSWIPKRNRSILN<br>TSQRGILEDEQMYQKCCNLFEKFFPSSSYRRPVGISSMVEAM<br>VSRARIDARVDFESGRIKKEEFSEIMKICSTIEELRRQK<br>(underline = highly conserved;<br>bold = hypervariable) |
| 192 | H1N1 pb2 Protein | AMGLRISSSFSFGGFTFKRTSGSSVKREEEVLTGNLQTLKLT<br>VHEGYEEFTMVGKRATAILRKATRRLIQLIVSGRDEQSIVEA<br>IVVAMVFSQEDCMVKAVRGDLNFVNRANQRLNPMHQLLR<br>HFQKDAKVLFLNWGVEPIDNVMGMIGILPDMTPSTEMSMR<br>GVRVSKMGVDEYSNAERVVVSIDRFLRVRDQRGNVLLSPE<br>EVSETQGTEKLTITYSSSMMWEINGPESVLINTYQWIIRNWE<br>TVKIQWSQNPTMLYNKMEFEPFQSLVPKAIRGQYSGFVRTL<br>FQQMRDVLGTFDTTQIIKLLPFAAAPPKQSRMQFSSLTVNVR<br>GSGMKILVRGNSPVFNYNKTTKRLTVLGKDAGTLTEDPDE<br>GTAGVESAVLRGFLILGKEDRRYGPALSINELSNLAKGEKA |

| SEQ ID NO | Description | Sequence |
|---|---|---|
| | | <u>NVLIGQGDVVLVMKRKRDSS</u>ILTDSQTA<u>TKRIRMAIN</u><br>(underline = highly conserved;<br>bold = hypervariable) |
| 193 | H1N1 NS2 Protein | MDSNTMSSFQDILMRMSKMQLGSSSEDLNGMVTRFESLKI<br>YRDSLGETVMRMGDLHYLQSRNEKWREQLGQKFEEIRWLI<br>EEMRHRLKATENSFEQITFMQALQLLLEVEQEIRAFSFQLI<br>(underline = highly conserved;<br>bold = hypervariable) |

SEQUENCE LISTING

```
Sequence total quantity: 193
SEQ ID NO: 1             moltype = AA  length = 566
FEATURE                  Location/Qualifiers
REGION                   1..566
                         note = misc_feature - H1N1 Hemagglutinin A/Michigan/45/2015
                          strain (amino acid) GenBank: MK622940.1
source                   1..566
                         mol_type = protein
                         organism = synthetic construct
SEQUENCE: 1
MKAILVVLLY TFTTANADTL CIGYHANNST DTVDTVLEKN VTVTHSVNLL EDKHNGKLCK    60
LRGVAPLHLG KCNIAGWILG NPECESLSTA SSWSYIVETS NSDNGTCYPG DFINYEELRE   120
QLSSVSSFER FEIFPKTSSW PNHDSNKGVT AACPHAGAKS FYKNLIWLVK KGNSYPKLNQ   180
SYINDKGKEV LVLWGIHHPS TTADQQSLYQ NADAYVFVGT SRYSKKFKPE IATRPKVRDQ   240
EGRMNYYWTL VEPGDKITFE ATGNLVVPRY AFTMERNAGS GIIISDTPVH DCNTTCQTPE   300
GAINTSLPFQ NIHPITIGKC PKYVKSTKLR LATGLRNVPS IQSRGLFGAI AGFIEGGWTG   360
MVDGWYGYHH QNEQGSGYAA DLKSTQNAID KITNKVNSVI EKMNTQFTAV GKEFNHLEKR   420
IENLNKKVDD GFLDIWTYNA ELLVLLENER TLDYHDSNVK NLYEKVRNQL KNNAKEIGNG   480
CFEFYHKCDN TCMESVKNGT YDYPKYSEEA KLNREKIDGV KLESTRIYQI LAIYSTVASS   540
LVLVVSLGAI SFWMCSNGSL QCRICI                                       566

SEQ ID NO: 2             moltype = AA  length = 469
FEATURE                  Location/Qualifiers
REGION                   1..469
                         note = misc_feature - H1N1 Neuraminidase A/Michigan/45/2015
                          strain (amino acid) GenBank: MK622934.1
source                   1..469
                         mol_type = protein
                         organism = synthetic construct
SEQUENCE: 2
MNPNQKIITI GSICMTIGMA NLILQIGNII SIWVSHSIQI GNQSQIETCN QSVITYENNT    60
WVNQTYVNIS NTNFAAGQSV VSVKLAGNSS LCPVSGWAIY SKDNSVRIGS KGDVFVIREP   120
FISCSPLECR TFFLTQGALL NDKHSNGTIK DRSPYRTLMS CPIGEVPSPY NSRFESVAWS   180
ASACHDGINW LTIGISGPDS GAVAVLKYNG IITDTIKSWR NNILRTQESE CACVNGSCFT   240
IMTDGPSDGQ ASYKIFRIEK GKIIKSVEMK APNYHYEECS CYPDSSEITC VCRDNWHGSN   300
RPWVSFNQNL EYQMGYICSG VFGDNPRPND KTGSCGPVSS NGANGVKGFS FKYGNGVWIG   360
RTKSISSRKG FEMIWDPNGW TGTDNKFSIK QDIVGINEWS GYSGSFVQHP ELTGLDCIRP   420
CFWVELIRGR PEENTIWTSG SSISFCGVNS DTVGWSWPDG AELPFTIDK              469

SEQ ID NO: 3             moltype = AA  length = 570
FEATURE                  Location/Qualifiers
REGION                   1..570
                         note = misc_feature - H3N2 Hemagglutinin
                          A/Mississippi/27/2013 strain (amino acid) GenBank:
                          AIK26600.1
source                   1..570
                         mol_type = protein
                         organism = synthetic construct
SEQUENCE: 3
MKTIIALSYI LCLVFAQKLP PYGNSTATLC LGHHAVPNGT IVKTITNDRI EVTNATELVQ    60
NSSIGEICDS PHQILDGENC TLIDALLGDP QCDGFQNKKW DLFVERSKAY SNCYPYDVPD   120
YASLRSLVAS SGTLEFNNES FNWTGVTQNG TSSACIRRSN SSFFSRLNWL THLNFKYPAL   180
NVTMPNNEQF DKLYIWGVHH PGTDKDQIFL YAQSSGRITV STKRSQQAVI PNIGSRPRIR   240
NIPSRISIYW TIVKPGDILL INSTGNLIAP RGYFKIRSGK SSIMRSDAPI GKCKSECITP   300
NGSIPNDKPF QNVNRITYGA CPRYVKQSTL KLATGMRNVP EKQTRGIFGA IAGFIENGWE   360
GMVDGWYGFR HQNSEGRGQA ADLKSTQAAI DQINGKLNRL IGKTNEKFHQ IEKEFSEVEG   420
RIQDLEKYVE DTKIDLWSYN AELLVALENQ HTIDLTDSEM NKLFEKTKKQ LRENAEDMGN   480
```

```
GCFKIYHKCD NACIGSIRNG TYDHNVYRDE ALNNRFQIKG VELKSGYKDW ILWISFAISC    540
FLLCVALKGF IMWACQKGNI RCNIRCNICI                                    570

SEQ ID NO: 4            moltype = AA  length = 469
FEATURE                 Location/Qualifiers
REGION                  1..469
                        note = misc_feature - H3N2 Neuraminidase
                          A/Miyagi/N1289/2005 strain (amino acid) GenBank: AB271522.1
SITE                    378
                        note = misc_feature - Xaa can be any naturally occurring
                          amino acid
source                  1..469
                        mol_type = protein
                        organism = synthetic construct
SEQUENCE: 4
MNPNQKIITI GSVSLTISTI CFFMQIAILI TTVTLHFKQY EFNSPPNNQV MLCEPTIIER    60
NITEIVYLTN TTIEKEICPK LAEYRKWSKP QCNITGFAPF SKDNSIRLSA GGDIWVTREP   120
YVSCDPDKCY QFALGQGTTL NNVHSNDIVR DRTPYRTLLM NELGVPFHLG TKQVCIAWSS   180
SSCHDGKAWL HVCVTGDDKN ATASFIYNGR LVDSIVSWSK EILRTQESEC VCINGTCTVV   240
MTDGSASGKA DTKILFIEEG KIVHTSTLSG SAQHVEECSC YPRYPGVRCV CRDNWKGSNR   300
PIVDINIKDY SIVSSYVCSG LVGDTPRKND SSSSSHCLDP NNEEGGHGVK GWAFDDGNDV   360
WMGRTISEKL RSGYETFXVI EGWSNPNSKL QINRQVIVDR GNRSGYSGIF SVEGKSCINR   420
CFYVELIRGR KEETEVLWTS NSIVVFCGTS GTYGTGSWPD GADINLMPI              469

SEQ ID NO: 5            moltype = AA  length = 585
FEATURE                 Location/Qualifiers
REGION                  1..585
                        note = misc_feature - Influenza B Hemagglutinin
                          B/Brisbane/60/2008 strain (amino acid) GenBank: KX058884.1
source                  1..585
                        mol_type = protein
                        organism = synthetic construct
SEQUENCE: 5
MKAIIVLLMV VTSNADRICT GITSSNSPHV VKTATQGEVN VTGVIPLTTT PTKSHFANLK    60
GTETRGKLCP KCLNCTDLDV ALGRPKCTGK IPSARVSILH EVRPVTSGCF PIMHDRTKIR   120
QLPNLLRGYE HIRLSTHNVI NAENAPGGPY KIGTSGSCPN ITNGNGFFAT MAWAVPKNDK   180
NKTATNPLTI EVPYICTEGE DQITVWGFHS DDETQMAKLY GDSKPQKFTS SANGVTTHYV   240
SQIGGFPNQT EDGGLPQSGR IVVDYMVQKS GKTGTITYQR GILLPQKVWC ASGRSKVIKG   300
SLPLIGEADC LHEKYGGLNK SKPYYTGEHA KAIGNCPIWV KTPLKLANGT KYRPPAKLLK   360
ERGFFGAIAG FLEGGWEGMI AGWHGYTSHG AHGVAVAADL KSTQEAINKI TKNLNSLSEL   420
EVKNLQRLSG AMDELHNEIL ELDEKVDDLR ADTISSQIEL AVLLSNEGII NSEDEHLLAL   480
ERKLKKMLGP SAVEIGNGCF ETKHKCNQTC LDRIAAGTFD AGEFSLPTFD SLNITAASLN   540
DDGLDNHTIL LYYSTAASSL AVTLMIAIFV VYMVSRDNVS CSICL                  585

SEQ ID NO: 6            moltype = AA  length = 467
FEATURE                 Location/Qualifiers
REGION                  1..467
                        note = misc_feature - Influenza B Neuraminidase
                          B/Wisconsin/05/2016 strain (amino acid) GenBank: KX007164.1
source                  1..467
                        mol_type = protein
                        organism = synthetic construct
SEQUENCE: 6
MLPSTIQTLT LFLTSGGVLL SLYVSASLSY LLYSDILLKF SPTEITAPTM PLDCANASNV    60
QAVNRSATKG VTLLLLPEPE WTYPRLSCPG STFQKALLIS PHRFGETKGN SAPLIIREPF   120
VACGPNECKH FALTHYAAQP GGYYNGTRGD RNKLRHLISV KLGKIPTVEN SIFHMAAWSG   180
SACHDGKEWT YIGVDGPDNN ALLKVKYGEA YTDTYHSYAN NILRTQESAC NCIGGNCYLM   240
ITDGSASGVS ECRFLKIREG RIIKEIFPTG RVKHTEECTC GFASNKTIEC ACRDNRYTAK   300
RPFVKLNVET DTAEIRLMCT DTYLDTPRPN DGSITGPCES DGDKGSGGIK GGFVHQRMKS   360
KIGRWYSRTM SKTERMGMGL YVKYGGDPWA DSDALAFSGV MVSMKEPGWY SFGFEIKDKK   420
CDVPCIGIEM VHDGGKETWH SAATAIYCLM GSGQLLWDTV TGVDMAL                467

SEQ ID NO: 7            moltype = AA  length = 8
FEATURE                 Location/Qualifiers
REGION                  1..8
                        note = misc_feature - H1N1 Hemagglutinin conserved region
                          (amino acid)
source                  1..8
                        mol_type = protein
                        organism = synthetic construct
SEQUENCE: 7
GYHANNST                                                             8

SEQ ID NO: 8            moltype = DNA  length = 24
FEATURE                 Location/Qualifiers
misc_feature            1..24
                        note = H1N1 Hemagglutinin conserved region (nucleic acid)
```

```
source                  1..24
                        mol_type = other DNA
                        organism = synthetic construct
SEQUENCE: 8
ggttatcatg cgaacaattc aaca                                              24

SEQ ID NO: 9            moltype = AA  length = 7
FEATURE                 Location/Qualifiers
REGION                  1..7
                        note = misc_feature - H1N1 Hemagglutinin conserved region
                        (amino acid)
source                  1..7
                        mol_type = protein
                        organism = synthetic construct
SEQUENCE: 9
NVTVTHS                                                                 7

SEQ ID NO: 10           moltype = DNA  length = 21
FEATURE                 Location/Qualifiers
misc_feature            1..21
                        note = H1N1 Hemagglutinin conserved region (nucleic acid)
source                  1..21
                        mol_type = other DNA
                        organism = synthetic construct
SEQUENCE: 10
aatgtaacag taacacactc t                                                 21

SEQ ID NO: 11           moltype = AA  length = 7
FEATURE                 Location/Qualifiers
REGION                  1..7
                        note = misc_feature - H1N1 Hemagglutinin conserved region
                        (amino acid)
source                  1..7
                        mol_type = protein
                        organism = synthetic construct
SEQUENCE: 11
SWSYIVE                                                                 7

SEQ ID NO: 12           moltype = DNA  length = 21
FEATURE                 Location/Qualifiers
misc_feature            1..21
                        note = H1N1 Hemagglutinin conserved region (nucleic acid)
source                  1..21
                        mol_type = other DNA
                        organism = synthetic construct
SEQUENCE: 12
tcatggtcct acattgtgga a                                                 21

SEQ ID NO: 13           moltype = AA  length = 12
FEATURE                 Location/Qualifiers
REGION                  1..12
                        note = misc_feature - H1N1 Hemagglutinin conserved region
                        (amino acid)
source                  1..12
                        mol_type = protein
                        organism = synthetic construct
SEQUENCE: 13
QSRGLFGAIA GF                                                           12

SEQ ID NO: 14           moltype = DNA  length = 36
FEATURE                 Location/Qualifiers
misc_feature            1..36
                        note = H1N1 Hemagglutinin conserved region (nucleic acid)
source                  1..36
                        mol_type = other DNA
                        organism = synthetic construct
SEQUENCE: 14
caatctagag gcctattcgg ggccattgcc ggcttc                                 36

SEQ ID NO: 15           moltype = AA  length = 8
FEATURE                 Location/Qualifiers
REGION                  1..8
                        note = misc_feature - H1N1 Hemagglutinin conserved region
                        (amino acid)
source                  1..8
                        mol_type = protein
                        organism = synthetic construct
SEQUENCE: 15
QGSGYAAD                                                                8
```

| | | |
|---|---|---|
| SEQ ID NO: 16 | moltype = DNA length = 24 | |
| FEATURE | Location/Qualifiers | |
| misc_feature | 1..24 | |
| | note = H1N1 Hemagglutinin conserved region (nucleic acid) | |
| source | 1..24 | |
| | mol_type = other DNA | |
| | organism = synthetic construct | |
| SEQUENCE: 16 | | |
| caggggtcag gatatgcagc cgac | | 24 |
| | | |
| SEQ ID NO: 17 | moltype = AA length = 7 | |
| FEATURE | Location/Qualifiers | |
| REGION | 1..7 | |
| | note = misc_feature - H1N1 Hemagglutinin conserved region (amino acid) | |
| source | 1..7 | |
| | mol_type = protein | |
| | organism = synthetic construct | |
| SEQUENCE: 17 | | |
| ITNKVNS | | 7 |
| | | |
| SEQ ID NO: 18 | moltype = DNA length = 21 | |
| FEATURE | Location/Qualifiers | |
| misc_feature | 1..21 | |
| | note = H1N1 Hemagglutinin conserved region (nucleic acid) | |
| source | 1..21 | |
| | mol_type = other DNA | |
| | organism = synthetic construct | |
| SEQUENCE: 18 | | |
| attactaaca aagtaaattc t | | 21 |
| | | |
| SEQ ID NO: 19 | moltype = AA length = 8 | |
| FEATURE | Location/Qualifiers | |
| REGION | 1..8 | |
| | note = misc_feature - H1N1 Hemagglutinin conserved region (amino acid) | |
| source | 1..8 | |
| | mol_type = protein | |
| | organism = synthetic construct | |
| SEQUENCE: 19 | | |
| WTYNAELL | | 8 |
| | | |
| SEQ ID NO: 20 | moltype = DNA length = 24 | |
| FEATURE | Location/Qualifiers | |
| misc_feature | 1..24 | |
| | note = H1N1 Hemagglutinin conserved region (nucleic acid) | |
| source | 1..24 | |
| | mol_type = other DNA | |
| | organism = synthetic construct | |
| SEQUENCE: 20 | | |
| tggacttaca atgccgaact gttg | | 24 |
| | | |
| SEQ ID NO: 21 | moltype = AA length = 7 | |
| FEATURE | Location/Qualifiers | |
| REGION | 1..7 | |
| | note = misc_feature - H1N1 Hemagglutinin conserved region (amino acid) | |
| source | 1..7 | |
| | mol_type = protein | |
| | organism = synthetic construct | |
| SEQUENCE: 21 | | |
| GCFEFYH | | 7 |
| | | |
| SEQ ID NO: 22 | moltype = DNA length = 21 | |
| FEATURE | Location/Qualifiers | |
| misc_feature | 1..21 | |
| | note = H1N1 Hemagglutinin conserved region (nucleic acid) | |
| source | 1..21 | |
| | mol_type = other DNA | |
| | organism = synthetic construct | |
| SEQUENCE: 22 | | |
| gcctgctttg aattttacca c | | 21 |
| | | |
| SEQ ID NO: 23 | moltype = AA length = 6 | |
| FEATURE | Location/Qualifiers | |
| REGION | 1..6 | |
| | note = misc_feature - H1N1 Hemagglutinin conserved region (amino acid) | |

```
source                  1..6
                        mol_type = protein
                        organism = synthetic construct
SEQUENCE: 23
LGNPEC                                                                    6

SEQ ID NO: 24           moltype = DNA   length = 18
FEATURE                 Location/Qualifiers
misc_feature            1..18
                        note = H1N1 Hemagglutinin conserved region (nucleic acid)
source                  1..18
                        mol_type = other DNA
                        organism = synthetic construct
SEQUENCE: 24
ctgggaaatc cagagtgt                                                       18

SEQ ID NO: 25           moltype = AA   length = 6
FEATURE                 Location/Qualifiers
REGION                  1..6
                        note = misc_feature - H1N1 Hemagglutinin conserved region
                        (amino acid)
source                  1..6
                        mol_type = protein
                        organism = synthetic construct
SEQUENCE: 25
EGGWTG                                                                    6

SEQ ID NO: 26           moltype = DNA   length = 18
FEATURE                 Location/Qualifiers
misc_feature            1..18
                        note = H1N1 Hemagglutinin conserved region (nucleic acid)
source                  1..18
                        mol_type = other DNA
                        organism = synthetic construct
SEQUENCE: 26
gaagggggt ggacaggg                                                        18

SEQ ID NO: 27           moltype = AA   length = 6
FEATURE                 Location/Qualifiers
REGION                  1..6
                        note = misc_feature - H1N1 Hemagglutinin conserved region
                        (amino acid)
source                  1..6
                        mol_type = protein
                        organism = synthetic construct
SEQUENCE: 27
LLENER                                                                    6

SEQ ID NO: 28           moltype = DNA   length = 18
FEATURE                 Location/Qualifiers
misc_feature            1..18
                        note = H1N1 Hemagglutinin conserved region (nucleic acid)
source                  1..18
                        mol_type = other DNA
                        organism = synthetic construct
SEQUENCE: 28
ctattggaaa atgaaaga                                                       18

SEQ ID NO: 29           moltype = AA   length = 12
FEATURE                 Location/Qualifiers
REGION                  1..12
                        note = misc_feature - H1N1 Neuraminidase conserved region
                        (amino acid)
source                  1..12
                        mol_type = protein
                        organism = synthetic construct
SEQUENCE: 29
MNPNQKIITI GS                                                             12

SEQ ID NO: 30           moltype = DNA   length = 36
FEATURE                 Location/Qualifiers
misc_feature            1..36
                        note = H1N1 Neuraminidase conserved region (nucleic acid)
source                  1..36
                        mol_type = other DNA
                        organism = synthetic construct
SEQUENCE: 30
atgaatccaa accaaaagat aataaccatt ggttcg                                   36
```

```
SEQ ID NO: 31            moltype = AA   length = 10
FEATURE                  Location/Qualifiers
REGION                   1..10
                         note = misc_feature - H1N1 Neuraminidase conserved region
                         (amino acid)
source                   1..10
                         mol_type = protein
                         organism = synthetic construct
SEQUENCE: 31
RIGSKGDVFV                                                                  10

SEQ ID NO: 32            moltype = DNA   length = 30
FEATURE                  Location/Qualifiers
misc_feature             1..30
                         note = H1N1 Neuraminidase conserved region (nucleic acid)
source                   1..30
                         mol_type = other DNA
                         organism = synthetic construct
SEQUENCE: 32
agaatcggtt ccaaggggga tgtgtttgtc                                            30

SEQ ID NO: 33            moltype = AA   length = 8
FEATURE                  Location/Qualifiers
REGION                   1..8
                         note = misc_feature - H1N1 Neuraminidase conserved region
                         (amino acid)
source                   1..8
                         mol_type = protein
                         organism = synthetic construct
SEQUENCE: 33
REPFISCS                                                                     8

SEQ ID NO: 34            moltype = DNA   length = 18
FEATURE                  Location/Qualifiers
misc_feature             1..18
                         note = H1N1 Neuraminidase conserved region (nucleic acid)
source                   1..18
                         mol_type = other DNA
                         organism = synthetic construct
SEQUENCE: 34
agggaaccat tcatatca                                                         18

SEQ ID NO: 35            moltype = AA   length = 18
FEATURE                  Location/Qualifiers
REGION                   1..18
                         note = misc_feature - H1N1 Neuraminidase conserved region
                         (amino acid)
source                   1..18
                         mol_type = protein
                         organism = synthetic construct
SEQUENCE: 35
TFFLTQGALL NDKHSNGT                                                         18

SEQ ID NO: 36            moltype = DNA   length = 54
FEATURE                  Location/Qualifiers
misc_feature             1..54
                         note = H1N1 Neuraminidase conserved region (nucleic acid)
source                   1..54
                         mol_type = other DNA
                         organism = synthetic construct
SEQUENCE: 36
accttcttct tgactcaagg ggccttgcta aatgacaaac attccaatgg aacc                 54

SEQ ID NO: 37            moltype = AA   length = 7
FEATURE                  Location/Qualifiers
REGION                   1..7
                         note = misc_feature - H1N1 Neuraminidase conserved region
                         (amino acid)
source                   1..7
                         mol_type = protein
                         organism = synthetic construct
SEQUENCE: 37
KDRSPYR                                                                      7

SEQ ID NO: 38            moltype = DNA   length = 21
FEATURE                  Location/Qualifiers
misc_feature             1..21
                         note = H1N1 Neuraminidase conserved region (nucleic acid)
```

```
source                  1..21
                        mol_type = other DNA
                        organism = synthetic construct
SEQUENCE: 38
aaagacagga gcccataccg a                                                21

SEQ ID NO: 39           moltype = AA  length = 14
FEATURE                 Location/Qualifiers
REGION                  1..14
                        note = misc_feature - H1N1 Neuraminidase conserved region
                          (amino acid)
source                  1..14
                        mol_type = protein
                        organism = synthetic construct
SEQUENCE: 39
FESVAWSASA CHDG                                                        14

SEQ ID NO: 40           moltype = DNA  length = 42
FEATURE                 Location/Qualifiers
misc_feature            1..42
                        note = H1N1 Neuraminidase conserved region (nucleic acid)
source                  1..42
                        mol_type = other DNA
                        organism = synthetic construct
SEQUENCE: 40
tttgagtcag tcgcttggtc agcaagtgct tgtcatgatg gc                          42

SEQ ID NO: 41           moltype = AA  length = 10
FEATURE                 Location/Qualifiers
REGION                  1..10
                        note = misc_feature - H1N1 Neuraminidase conserved region
                          (amino acid)
source                  1..10
                        mol_type = protein
                        organism = synthetic construct
SEQUENCE: 41
WLTIGISGPD                                                             10

SEQ ID NO: 42           moltype = DNA  length = 30
FEATURE                 Location/Qualifiers
misc_feature            1..30
                        note = H1N1 Neuraminidase conserved region (nucleic acid)
source                  1..30
                        mol_type = other DNA
                        organism = synthetic construct
SEQUENCE: 42
tggctaacaa ttggaatttc tggcccagac                                       30

SEQ ID NO: 43           moltype = AA  length = 9
FEATURE                 Location/Qualifiers
REGION                  1..9
                        note = misc_feature - H1N1 Neuraminidase conserved region
                          (amino acid)
source                  1..9
                        mol_type = protein
                        organism = synthetic construct
SEQUENCE: 43
ILRTQESEC                                                               9

SEQ ID NO: 44           moltype = DNA  length = 27
FEATURE                 Location/Qualifiers
misc_feature            1..27
                        note = H1N1 Neuraminidase conserved region (nucleic acid)
source                  1..27
                        mol_type = other DNA
                        organism = synthetic construct
SEQUENCE: 44
atattgagaa cacaagagtc tgaatgt                                          27

SEQ ID NO: 45           moltype = AA  length = 9
FEATURE                 Location/Qualifiers
REGION                  1..9
                        note = misc_feature - H1N1 Neuraminidase conserved region
                          (amino acid)
source                  1..9
                        mol_type = protein
                        organism = synthetic construct
SEQUENCE: 45
YEECSCYPD                                                               9
```

```
SEQ ID NO: 46          moltype = DNA  length = 27
FEATURE                Location/Qualifiers
misc_feature           1..27
                       note = H1N1 Neuraminidase conserved region (nucleic acid)
source                 1..27
                       mol_type = other DNA
                       organism = synthetic construct
SEQUENCE: 46
tatgaggaat gctcctgtta ccctgat                                         27

SEQ ID NO: 47          moltype = AA  length = 21
FEATURE                Location/Qualifiers
REGION                 1..21
                       note = misc_feature - H1N1 Neuraminidase conserved region
                         (amino acid)
source                 1..21
                       mol_type = protein
                       organism = synthetic construct
SEQUENCE: 47
CVCRDNWHGS NRPWVSFNQN L                                               21

SEQ ID NO: 48          moltype = DNA  length = 63
FEATURE                Location/Qualifiers
misc_feature           1..63
                       note = H1N1 Neuraminidase conserved region (nucleic acid)
source                 1..63
                       mol_type = other DNA
                       organism = synthetic construct
SEQUENCE: 48
tgtgtgtgca gggataactg gcatggctcg aatcgaccgt gggtgtcttt caaccagaat     60
ctg                                                                   63

SEQ ID NO: 49          moltype = AA  length = 10
FEATURE                Location/Qualifiers
REGION                 1..10
                       note = misc_feature - H1N1 Neuraminidase conserved region
                         (amino acid)
source                 1..10
                       mol_type = protein
                       organism = synthetic construct
SEQUENCE: 49
NGVWIGRTKS                                                            10

SEQ ID NO: 50          moltype = DNA  length = 30
FEATURE                Location/Qualifiers
misc_feature           1..30
                       note = H1N1 Neuraminidase conserved region (nucleic acid)
source                 1..30
                       mol_type = other DNA
                       organism = synthetic construct
SEQUENCE: 50
aatggtgttt ggatagggag aactaaaagc                                      30

SEQ ID NO: 51          moltype = AA  length = 12
FEATURE                Location/Qualifiers
REGION                 1..12
                       note = misc_feature - H1N1 Neuraminidase conserved region
                         (amino acid)
source                 1..12
                       mol_type = protein
                       organism = synthetic construct
SEQUENCE: 51
GFEMIWDPNG WT                                                         12

SEQ ID NO: 52          moltype = DNA  length = 36
FEATURE                Location/Qualifiers
misc_feature           1..36
                       note = H1N1 Neuraminidase conserved region (nucleic acid)
source                 1..36
                       mol_type = other DNA
                       organism = synthetic construct
SEQUENCE: 52
ggttttgaga tgatttggga tccgaatgga tggact                               36

SEQ ID NO: 53          moltype = AA  length = 17
FEATURE                Location/Qualifiers
```

```
REGION                      1..17
                            note = misc_feature - H1N1 Neuraminidase conserved region
                              (amino acid)
source                      1..17
                            mol_type = protein
                            organism = synthetic construct
SEQUENCE: 53
WSGYSGSFVQ HPELTGL                                                             17

SEQ ID NO: 54               moltype = DNA   length = 51
FEATURE                     Location/Qualifiers
misc_feature                1..51
                            note = H1N1 Neuraminidase conserved region (nucleic acid)
source                      1..51
                            mol_type = other DNA
                            organism = synthetic construct
SEQUENCE: 54
tggtcagggt atagcgggag ttttgttcag catccagaac taacagggct g                       51

SEQ ID NO: 55               moltype = AA   length = 8
FEATURE                     Location/Qualifiers
REGION                      1..8
                            note = misc_feature - H1N1 Neuraminidase conserved region
                              (amino acid)
source                      1..8
                            mol_type = protein
                            organism = synthetic construct
SEQUENCE: 55
RPCFWVEL                                                                        8

SEQ ID NO: 56               moltype = DNA   length = 24
FEATURE                     Location/Qualifiers
misc_feature                1..24
                            note = H1N1 Neuraminidase conserved region (nucleic acid)
source                      1..24
                            mol_type = other DNA
                            organism = synthetic construct
SEQUENCE: 56
agaccttgct tctgggttga acta                                                     24

SEQ ID NO: 57               moltype = AA   length = 12
FEATURE                     Location/Qualifiers
REGION                      1..12
                            note = misc_feature - H1N1 Neuraminidase conserved region
                              (amino acid)
source                      1..12
                            mol_type = protein
                            organism = synthetic construct
SEQUENCE: 57
WTSGSSISFC GV                                                                  12

SEQ ID NO: 58               moltype = DNA   length = 36
FEATURE                     Location/Qualifiers
misc_feature                1..36
                            note = H1N1 Neuraminidase conserved region (nucleic acid)
source                      1..36
                            mol_type = other DNA
                            organism = synthetic construct
SEQUENCE: 58
tggactagcg ggagcagcat atccttttgt ggtgta                                        36

SEQ ID NO: 59               moltype = AA   length = 11
FEATURE                     Location/Qualifiers
REGION                      1..11
                            note = misc_feature - H1N1 Neuraminidase conserved region
                              (amino acid)
source                      1..11
                            mol_type = protein
                            organism = synthetic construct
SEQUENCE: 59
WSWPDGAELP F                                                                   11

SEQ ID NO: 60               moltype = DNA   length = 33
FEATURE                     Location/Qualifiers
misc_feature                1..33
                            note = H1N1 Neuraminidase conserved region (nucleic acid)
source                      1..33
                            mol_type = other DNA
                            organism = synthetic construct
```

```
SEQUENCE: 60
tggtcttggc cagacggtgc tgagttgcca ttt                                    33

SEQ ID NO: 61           moltype = AA   length = 7
FEATURE                 Location/Qualifiers
REGION                  1..7
                        note = misc_feature - H3N2 Hemagglutinin conserved region
                          (amino acid)
source                  1..7
                        mol_type = protein
                        organism = synthetic construct
SEQUENCE: 61
LCLGHHA                                                                 7

SEQ ID NO: 62           moltype = DNA   length = 24
FEATURE                 Location/Qualifiers
misc_feature            1..24
                        note = H3N2 Hemagglutinin conserved region (nucleic acid)
source                  1..24
                        mol_type = other DNA
                        organism = synthetic construct
SEQUENCE: 62
ctgtgccttg ggcaccatgc atta                                              24

SEQ ID NO: 63           moltype = AA   length = 10
FEATURE                 Location/Qualifiers
REGION                  1..10
                        note = misc_feature - H3N2 Hemagglutinin conserved region
                          (amino acid)
source                  1..10
                        mol_type = protein
                        organism = synthetic construct
SEQUENCE: 63
GNLIAPRGYF                                                              10

SEQ ID NO: 64           moltype = DNA   length = 30
FEATURE                 Location/Qualifiers
misc_feature            1..30
                        note = H3N2 Hemagglutinin conserved region (nucleic acid)
source                  1..30
                        mol_type = other DNA
                        organism = synthetic construct
SEQUENCE: 64
gggaatctaa ttgctcctag gggttacttc                                        30

SEQ ID NO: 65           moltype = AA   length = 9
FEATURE                 Location/Qualifiers
REGION                  1..9
                        note = misc_feature - H3N2 Hemagglutinin conserved region
                          (amino acid)
source                  1..9
                        mol_type = protein
                        organism = synthetic construct
SEQUENCE: 65
LKLATGMRN                                                               9

SEQ ID NO: 66           moltype = DNA   length = 27
FEATURE                 Location/Qualifiers
misc_feature            1..27
                        note = H3N2 Hemagglutinin conserved region (nucleic acid)
source                  1..27
                        mol_type = other DNA
                        organism = synthetic construct
SEQUENCE: 66
ctgaaattgg caacaggaat gcgaaat                                           27

SEQ ID NO: 67           moltype = AA   length = 14
FEATURE                 Location/Qualifiers
REGION                  1..14
                        note = misc_feature - H3N2 Hemagglutinin conserved region
                          (amino acid)
source                  1..14
                        mol_type = protein
                        organism = synthetic construct
SEQUENCE: 67
FGAIAGFIEN GWEG                                                         14

SEQ ID NO: 68           moltype = DNA   length = 42
FEATURE                 Location/Qualifiers
```

```
misc_feature            1..42
                        note = H3N2 Hemagglutinin conserved region (nucleic acid)
source                  1..42
                        mol_type = other DNA
                        organism = synthetic construct
SEQUENCE: 68
tttggcgcaa tagcaggttt catagaaaat ggttgggagg gg                              42

SEQ ID NO: 69           moltype = AA  length = 9
FEATURE                 Location/Qualifiers
REGION                  1..9
                        note = misc_feature - H3N2 Hemagglutinin conserved region
                        (amino acid)
source                  1..9
                        mol_type = protein
                        organism = synthetic construct
SEQUENCE: 69
KFHQIEKEF                                                                    9

SEQ ID NO: 70           moltype = DNA  length = 27
FEATURE                 Location/Qualifiers
misc_feature            1..27
                        note = H3N2 Hemagglutinin conserved region (nucleic acid)
source                  1..27
                        mol_type = other DNA
                        organism = synthetic construct
SEQUENCE: 70
aaattccatc agattgaaaa agaattc                                                27

SEQ ID NO: 71           moltype = AA  length = 7
FEATURE                 Location/Qualifiers
REGION                  1..7
                        note = misc_feature - H3N2 Hemagglutinin conserved region
                        (amino acid)
source                  1..7
                        mol_type = protein
                        organism = synthetic construct
SEQUENCE: 71
DLTDSEM                                                                      7

SEQ ID NO: 72           moltype = DNA  length = 21
FEATURE                 Location/Qualifiers
misc_feature            1..21
                        note = H3N2 Hemagglutinin conserved region (nucleic acid)
source                  1..21
                        mol_type = other DNA
                        organism = synthetic construct
SEQUENCE: 72
gatctaactg actcagaaat g                                                      21

SEQ ID NO: 73           moltype = AA  length = 7
FEATURE                 Location/Qualifiers
REGION                  1..7
                        note = misc_feature - H3N2 Hemagglutinin conserved region
                        (amino acid)
source                  1..7
                        mol_type = protein
                        organism = synthetic construct
SEQUENCE: 73
LRENAED                                                                      7

SEQ ID NO: 74           moltype = DNA  length = 21
FEATURE                 Location/Qualifiers
misc_feature            1..21
                        note = H3N2 Hemagglutinin conserved region (nucleic acid)
source                  1..21
                        mol_type = other DNA
                        organism = synthetic construct
SEQUENCE: 74
ctgagggaaa atgctgagga t                                                      21

SEQ ID NO: 75           moltype = AA  length = 9
FEATURE                 Location/Qualifiers
REGION                  1..9
                        note = misc_feature - H3N2 Neuraminidase conserved region
                        (amino acid)
source                  1..9
                        mol_type = protein
                        organism = synthetic construct
```

```
SEQUENCE: 75
QFALGQGTT                                                                       9

SEQ ID NO: 76              moltype = DNA  length = 27
FEATURE                    Location/Qualifiers
misc_feature               1..27
                           note = H3N2 Neuraminidase conserved region (nucleic acid)
source                     1..27
                           mol_type = other DNA
                           organism = synthetic construct
SEQUENCE: 76
caatttgccc ttggacaggg aacaaca                                                  27

SEQ ID NO: 77              moltype = AA  length = 7
FEATURE                    Location/Qualifiers
REGION                     1..7
                           note = misc_feature - H3N2 Neuraminidase conserved region
                             (amino acid)
source                     1..7
                           mol_type = protein
                           organism = synthetic construct
SEQUENCE: 77
AWSSSSC                                                                         7

SEQ ID NO: 78              moltype = DNA  length = 21
FEATURE                    Location/Qualifiers
misc_feature               1..21
                           note = H3N2 Neuraminidase conserved region (nucleic acid)
source                     1..21
                           mol_type = other DNA
                           organism = synthetic construct
SEQUENCE: 78
gcatggtcca gctcaagttg t                                                        21

SEQ ID NO: 79              moltype = AA  length = 8
FEATURE                    Location/Qualifiers
REGION                     1..8
                           note = misc_feature - H3N2 Neuraminidase conserved region
                             (amino acid)
source                     1..8
                           mol_type = protein
                           organism = synthetic construct
SEQUENCE: 79
LRTQESEC                                                                        8

SEQ ID NO: 80              moltype = DNA  length = 24
FEATURE                    Location/Qualifiers
misc_feature               1..24
                           note = H3N2 Neuraminidase conserved region (nucleic acid)
source                     1..24
                           mol_type = other DNA
                           organism = synthetic construct
SEQUENCE: 80
ctcaggaccc aggagtcaga atgc                                                     24

SEQ ID NO: 81              moltype = AA  length = 7
FEATURE                    Location/Qualifiers
REGION                     1..7
                           note = misc_feature - H3N2 Neuraminidase conserved region
                             (amino acid)
source                     1..7
                           mol_type = protein
                           organism = synthetic construct
SEQUENCE: 81
EECSCYP                                                                         7

SEQ ID NO: 82              moltype = DNA  length = 21
FEATURE                    Location/Qualifiers
misc_feature               1..21
                           note = H3N2 Neuraminidase conserved region (nucleic acid)
source                     1..21
                           mol_type = other DNA
                           organism = synthetic construct
SEQUENCE: 82
gaggagtgct cctgctatcc t                                                        21

SEQ ID NO: 83              moltype = AA  length = 10
FEATURE                    Location/Qualifiers
```

```
REGION                   1..10
                         note = misc_feature - H3N2 Neuraminidase conserved region
                           (amino acid)
source                   1..10
                         mol_type = protein
                         organism = synthetic construct
SEQUENCE: 83
CSGLVGDTPR                                                                        10

SEQ ID NO: 84            moltype = DNA  length = 30
FEATURE                  Location/Qualifiers
misc_feature             1..30
                         note = H3N2 Neuraminidase conserved region (nucleic acid)
source                   1..30
                         mol_type = other DNA
                         organism = synthetic construct
SEQUENCE: 84
tgctcaggac ttgttggaga cacacccaga                                                  30

SEQ ID NO: 85            moltype = AA  length = 8
FEATURE                  Location/Qualifiers
REGION                   1..8
                         note = misc_feature - H3N2 Neuraminidase conserved region
                           (amino acid)
source                   1..8
                         mol_type = protein
                         organism = synthetic construct
SEQUENCE: 85
GVKGWAFD                                                                           8

SEQ ID NO: 86            moltype = DNA  length = 24
FEATURE                  Location/Qualifiers
misc_feature             1..24
                         note = H3N2 Neuraminidase conserved region (nucleic acid)
source                   1..24
                         mol_type = other DNA
                         organism = synthetic construct
SEQUENCE: 86
ggagtgaaag gctgggcctt tgat                                                        24

SEQ ID NO: 87            moltype = AA  length = 11
FEATURE                  Location/Qualifiers
REGION                   1..11
                         note = misc_feature - H3N2 Neuraminidase conserved region
                           (amino acid)
source                   1..11
                         mol_type = protein
                         organism = synthetic construct
SEQUENCE: 87
NRCFYVELIR G                                                                      11

SEQ ID NO: 88            moltype = DNA  length = 33
FEATURE                  Location/Qualifiers
misc_feature             1..33
                         note = H3N2 Neuraminidase conserved region (nucleic acid)
source                   1..33
                         mol_type = other DNA
                         organism = synthetic construct
SEQUENCE: 88
aatcggtgct tttatgtgga gttgataagg gga                                              33

SEQ ID NO: 89            moltype = AA  length = 10
FEATURE                  Location/Qualifiers
REGION                   1..10
                         note = misc_feature - H3N2 Neuraminidase conserved region
                           (amino acid)
source                   1..10
                         mol_type = protein
                         organism = synthetic construct
SEQUENCE: 89
VFCGTSGTYG                                                                        10

SEQ ID NO: 90            moltype = DNA  length = 30
FEATURE                  Location/Qualifiers
misc_feature             1..30
                         note = H3N2 Neuraminidase conserved region (nucleic acid)
source                   1..30
                         mol_type = other DNA
                         organism = synthetic construct
```

```
SEQUENCE: 90
gtgttttgtg gcacctcagg tacatatgga                                    30

SEQ ID NO: 91           moltype = AA  length = 7
FEATURE                 Location/Qualifiers
REGION                  1..7
                        note = misc_feature - H3N2 Neuraminidase conserved region
                          (amino acid)
source                  1..7
                        mol_type = protein
                        organism = synthetic construct
SEQUENCE: 91
GSWPDGA                                                              7

SEQ ID NO: 92           moltype = DNA  length = 21
FEATURE                 Location/Qualifiers
misc_feature            1..21
                        note = H3N2 Neuraminidase conserved region (nucleic acid)
source                  1..21
                        mol_type = other DNA
                        organism = synthetic construct
SEQUENCE: 92
ggctcatggc ctgatggggc g                                              21

SEQ ID NO: 93           moltype = AA  length = 13
FEATURE                 Location/Qualifiers
REGION                  1..12
                        note = misc_feature - Influenza B Hemagglutinin conserved
                          region (amino acid)
source                  1..13
                        mol_type = protein
                        organism = synthetic construct
SEQUENCE: 93
VKTATQGEVN VTG                                                       13

SEQ ID NO: 94           moltype = DNA  length = 39
FEATURE                 Location/Qualifiers
misc_feature            1..39
                        note = Influenza B Hemagglutinin conserved region (nucleic
                          acid)
source                  1..39
                        mol_type = other DNA
                        organism = synthetic construct
SEQUENCE: 94
gtcaaaactg ctactcaagg ggaggtcaat gtgactggt                           39

SEQ ID NO: 95           moltype = AA  length = 9
FEATURE                 Location/Qualifiers
REGION                  1..9
                        note = misc_feature - Influenza B Hemagglutinin conserved
                          region (amino acid)
source                  1..9
                        mol_type = protein
                        organism = synthetic construct
SEQUENCE: 95
NCTDLDVAL                                                            9

SEQ ID NO: 96           moltype = DNA  length = 27
FEATURE                 Location/Qualifiers
misc_feature            1..27
                        note = Influenza B Hemagglutinin conserved region (nucleic
                          acid)
source                  1..27
                        mol_type = other DNA
                        organism = synthetic construct
SEQUENCE: 96
aactgcacag atctggacgt agccttg                                        27

SEQ ID NO: 97           moltype = AA  length = 17
FEATURE                 Location/Qualifiers
REGION                  1..17
                        note = misc_feature - Influenza B Hemagglutinin conserved
                          region (amino acid)_
source                  1..17
                        mol_type = protein
                        organism = synthetic construct
SEQUENCE: 97
TSGCFPIMHD RTKIRQL                                                   17
```

| | |
|---|---|
| SEQ ID NO: 98 | moltype = DNA  length = 51 |
| FEATURE | Location/Qualifiers |
| misc_feature | 1..51 |
| | note = Influenza B Hemagglutinin conserved region (nucleic acid) |
| source | 1..51 |
| | mol_type = other DNA |
| | organism = synthetic construct |

SEQUENCE: 98
acatctgggt gctttcctat aatgcacgac agaacaaaaa ttagacagct g         51

| | |
|---|---|
| SEQ ID NO: 99 | moltype = AA  length = 7 |
| FEATURE | Location/Qualifiers |
| REGION | 1..7 |
| | note = misc_feature - Influenza B Hemagglutinin conserved region (amino acid) |
| source | 1..7 |
| | mol_type = protein |
| | organism = synthetic construct |

SEQUENCE: 99
NLLRGYE                                                          7

| | |
|---|---|
| SEQ ID NO: 100 | moltype = DNA  length = 21 |
| FEATURE | Location/Qualifiers |
| misc_feature | 1..21 |
| | note = Influenza B Hemagglutinin conserved region (nucleic acid) |
| source | 1..21 |
| | mol_type = other DNA |
| | organism = synthetic construct |

SEQUENCE: 100
aaccttctcc gaggatacga a                                          21

| | |
|---|---|
| SEQ ID NO: 101 | moltype = AA  length = 7 |
| FEATURE | Location/Qualifiers |
| REGION | 1..7 |
| | note = misc_feature - Influenza B Hemagglutinin conserved region (amino acid) |
| source | 1..7 |
| | mol_type = protein |
| | organism = synthetic construct |

SEQUENCE: 101
TMAWAVP                                                          7

| | |
|---|---|
| SEQ ID NO: 102 | moltype = DNA  length = 21 |
| FEATURE | Location/Qualifiers |
| misc_feature | 1..21 |
| | note = Influenza B Hemagglutinin conserved region (nucleic acid) |
| source | 1..21 |
| | mol_type = other DNA |
| | organism = synthetic construct |

SEQUENCE: 102
acaatggctt gggccgtccc a                                          21

| | |
|---|---|
| SEQ ID NO: 103 | moltype = AA  length = 16 |
| FEATURE | Location/Qualifiers |
| REGION | 1..16 |
| | note = misc_feature - Influenza B Hemagglutinin conserved region (amino acid) |
| source | 1..16 |
| | mol_type = protein |
| | organism = synthetic construct |

SEQUENCE: 103
EDGGLPQSGR IVVDYM                                                16

| | |
|---|---|
| SEQ ID NO: 104 | moltype = DNA  length = 48 |
| FEATURE | Location/Qualifiers |
| misc_feature | 1..48 |
| | note = Influenza B Hemagglutinin conserved region (nucleic acid) |
| source | 1..48 |
| | mol_type = other DNA |
| | organism = synthetic construct |

SEQUENCE: 104
gaagacggag gactaccaca aagtggtaga attgttgttg attacatg              48

| | |
|---|---|
| SEQ ID NO: 105 | moltype = AA  length = 12 |
| FEATURE | Location/Qualifiers |

```
REGION                    1..12
                          note = misc_feature - Influenza B Hemagglutinin conserved
                             region (amino acid)
source                    1..12
                          mol_type = protein
                          organism = synthetic construct
SEQUENCE: 105
LPLIGEADCL HE                                                              12

SEQ ID NO: 106            moltype = DNA   length = 36
FEATURE                   Location/Qualifiers
misc_feature              1..36
                          note = Influenza B Hemagglutinin conserved region (nucleic
                             acid)
source                    1..36
                          mol_type = other DNA
                          organism = synthetic construct
SEQUENCE: 106
ttgcctttaa ttggagaagc agattgcctc cacgaa                                    36

SEQ ID NO: 107            moltype = AA   length = 13
FEATURE                   Location/Qualifiers
REGION                    1..13
                          note = misc_feature - Influenza B Hemagglutinin conserved
                             region (amino acid)
source                    1..13
                          mol_type = protein
                          organism = synthetic construct
SEQUENCE: 107
YGGLNKSKPY YTG                                                             13

SEQ ID NO: 108            moltype = DNA   length = 39
FEATURE                   Location/Qualifiers
misc_feature              1..39
                          note = Influenza B Hemagglutinin conserved region (nucleic
                             acid)
source                    1..39
                          mol_type = other DNA
                          organism = synthetic construct
SEQUENCE: 108
tacggtggat taaacaaaag caagccttac tacacaggg                                 39

SEQ ID NO: 109            moltype = AA   length = 9
FEATURE                   Location/Qualifiers
REGION                    1..9
                          note = misc_feature - Influenza B Hemagglutinin conserved
                             region (amino acid)
source                    1..9
                          mol_type = protein
                          organism = synthetic construct
SEQUENCE: 109
CPIWVKTPL                                                                   9

SEQ ID NO: 110            moltype = DNA   length = 27
FEATURE                   Location/Qualifiers
misc_feature              1..27
                          note = Influenza B Hemagglutinin conserved region (nucleic
                             acid)
source                    1..27
                          mol_type = other DNA
                          organism = synthetic construct
SEQUENCE: 110
tgcccaatat gggtgaaaac acccttg                                              27

SEQ ID NO: 111            moltype = AA   length = 17
FEATURE                   Location/Qualifiers
REGION                    1..17
                          note = misc_feature - Influenza B Hemagglutinin conserved
                             region (amino acid)
source                    1..17
                          mol_type = protein
                          organism = synthetic construct
SEQUENCE: 111
GFFGAIAGFL EGGWEGM                                                         17

SEQ ID NO: 112            moltype = DNA   length = 51
FEATURE                   Location/Qualifiers
```

```
misc_feature            1..51
                        note = Influenza B Hemagglutinin conserved region (nucleic
                         acid)
source                  1..51
                        mol_type = other DNA
                        organism = synthetic construct
SEQUENCE: 112
ggtttcttcg gagctattgc tggtttctta gaaggaggat gggaaggaat g           51

SEQ ID NO: 113          moltype = AA  length = 13
FEATURE                 Location/Qualifiers
REGION                  1..13
                        note = misc_feature - Influenza B Hemagglutinin conserved
                         region (amino acid)
source                  1..13
                        mol_type = protein
                        organism = synthetic construct
SEQUENCE: 113
AGWHGYTSHG AHG                                                     13

SEQ ID NO: 114          moltype = DNA  length = 39
FEATURE                 Location/Qualifiers
misc_feature            1..39
                        note = Influenza B Hemagglutinin conserved region (nucleic
                         acid)
source                  1..39
                        mol_type = other DNA
                        organism = synthetic construct
SEQUENCE: 114
gcaggttggc acggatacac atcccatggg gcacatgga                         39

SEQ ID NO: 115          moltype = AA  length = 12
FEATURE                 Location/Qualifiers
REGION                  1..12
                        note = misc_feature - Influenza B Hemagglutinin conserved
                         region (amino acid)
source                  1..12
                        mol_type = protein
                        organism = synthetic construct
SEQUENCE: 115
AVAADLKSTQ EA                                                      12

SEQ ID NO: 116          moltype = DNA  length = 36
FEATURE                 Location/Qualifiers
misc_feature            1..36
                        note = Influenza B Hemagglutinin conserved region (nucleic
                         acid)
source                  1..36
                        mol_type = other DNA
                        organism = synthetic construct
SEQUENCE: 116
gcggtggcag cagaccttaa gagcactcaa gaggcc                            36

SEQ ID NO: 117          moltype = AA  length = 13
FEATURE                 Location/Qualifiers
REGION                  1..13
                        note = misc_feature - Influenza B Hemagglutinin conserved
                         region (amino acid)
source                  1..13
                        mol_type = protein
                        organism = synthetic construct
SEQUENCE: 117
KITKNLNSLS ELE                                                     13

SEQ ID NO: 118          moltype = DNA  length = 39
FEATURE                 Location/Qualifiers
misc_feature            1..39
                        note = Influenza B Hemagglutinin conserved region (nucleic
                         acid)
source                  1..39
                        mol_type = other DNA
                        organism = synthetic construct
SEQUENCE: 118
aagataacaa aaaatctcaa ctctttgagt gagctggaa                         39

SEQ ID NO: 119          moltype = AA  length = 7
FEATURE                 Location/Qualifiers
```

```
REGION                          1..7
                                note = misc_feature - Influenza B Hemagglutinin conserved
                                   region (amino acid)_
source                          1..7
                                mol_type = protein
                                organism = synthetic construct
SEQUENCE: 119
KNLQRLS                                                                           7

SEQ ID NO: 120                  moltype = DNA   length = 21
FEATURE                         Location/Qualifiers
misc_feature                    1..21
                                note = Influenza B Hemagglutinin conserved region (nucleic
                                   acid)
source                          1..21
                                mol_type = other DNA
                                organism = synthetic construct
SEQUENCE: 120
aagaatcttc aaagactaag c                                                          21

SEQ ID NO: 121                  moltype = AA    length = 55
FEATURE                         Location/Qualifiers
REGION                          1..55
                                note = misc_feature - Influenza B Hemagglutinin conserved
                                   region (amino acid)_
source                          1..55
                                mol_type = protein
                                organism = synthetic construct
SEQUENCE: 121
EILELDEKVD DLRADTISSQ IELAVLLSNE GIINSEDEHL LALERKLKKM LGPSA                      55

SEQ ID NO: 122                  moltype = DNA   length = 165
FEATURE                         Location/Qualifiers
misc_feature                    1..165
                                note = Influenza B Hemagglutinin conserved region (nucleic
                                   acid)
source                          1..165
                                mol_type = other DNA
                                organism = synthetic construct
SEQUENCE: 122
gaaatactag aactagatga gaaagtggat gatctcagag ctgatacaat aagctcacaa                 60
atagaactcg cagtcctgct ttccaatgaa ggaataataa acagtgaaga tgaacatctc                120
ttggcgcttg aaagaaagct gaagaaaatg ctgggcccct ctgct                                165

SEQ ID NO: 123                  moltype = AA    length = 18
FEATURE                         Location/Qualifiers
REGION                          1..18
                                note = misc_feature - Influenza B Hemagglutinin conserved
                                   region (amino acid)_
source                          1..18
                                mol_type = protein
                                organism = synthetic construct
SEQUENCE: 123
IGNGCFETKH KCNQTCLD                                                              18

SEQ ID NO: 124                  moltype = DNA   length = 54
FEATURE                         Location/Qualifiers
misc_feature                    1..54
                                note = Influenza B Hemagglutinin conserved region (nucleic
                                   acid)
source                          1..54
                                mol_type = other DNA
                                organism = synthetic construct
SEQUENCE: 124
atagggaatg gatgctttga aaccaaacac aagtgcaacc agacctgtct cgac                      54

SEQ ID NO: 125                  moltype = AA    length = 19
FEATURE                         Location/Qualifiers
REGION                          1..19
                                note = misc_feature - Influenza B Hemagglutinin conserved
                                   region (amino acid)
source                          1..19
                                mol_type = protein
                                organism = synthetic construct
SEQUENCE: 125
AGEFSLPTFD SLNITAASL                                                             19

SEQ ID NO: 126                  moltype = DNA   length = 57
FEATURE                         Location/Qualifiers
```

| | |
|---|---|
| misc_feature | 1..57<br>note = Influenza B Hemagglutinin conserved region (nucleic acid) |
| source | 1..57<br>mol_type = other DNA<br>organism = synthetic construct |

SEQUENCE: 126
gcaggagaat tttctctccc cacctttgat tcactgaata ttactgctgc atcttta    57

| | |
|---|---|
| SEQ ID NO: 127 | moltype = AA length = 19 |
| FEATURE | Location/Qualifiers |
| REGION | 1..19<br>note = misc_feature - Influenza B Hemagglutinin conserved region (amino acid) |
| source | 1..19<br>mol_type = protein<br>organism = synthetic construct |

SEQUENCE: 127
HTILLYYSTA ASSLAVTLM                                              19

| | |
|---|---|
| SEQ ID NO: 128 | moltype = DNA length = 57 |
| FEATURE | Location/Qualifiers |
| misc_feature | 1..57<br>note = Influenza B Hemagglutinin conserved region (nucleic acid) |
| source | 1..57<br>mol_type = other DNA<br>organism = synthetic construct |

SEQUENCE: 128
catactatac tgctttacta ctcaactgct gcctccagtt tggctgtaac actgatg    57

| | |
|---|---|
| SEQ ID NO: 129 | moltype = AA length = 11 |
| FEATURE | Location/Qualifiers |
| REGION | 1..11<br>note = misc_feature - Influenza B Neuraminidase conserved region (amino acid) |
| source | 1..11<br>mol_type = protein<br>organism = synthetic construct |

SEQUENCE: 129
ALLISPHRFG E                                                      11

| | |
|---|---|
| SEQ ID NO: 130 | moltype = DNA length = 33 |
| FEATURE | Location/Qualifiers |
| misc_feature | 1..33<br>note = Influenza B Neuraminidase conserved region (nucleic acid) |
| source | 1..33<br>mol_type = other DNA<br>organism = synthetic construct |

SEQUENCE: 130
gcactcctaa ttagccctca tagattcgga gaa                              33

| | |
|---|---|
| SEQ ID NO: 131 | moltype = AA length = 12 |
| FEATURE | Location/Qualifiers |
| REGION | 1..12<br>note = misc_feature - Influenza B Neuraminidase conserved region (amino acid) |
| source | 1..12<br>mol_type = protein<br>organism = synthetic construct |

SEQUENCE: 131
HFALTHYAAQ PG                                                     12

| | |
|---|---|
| SEQ ID NO: 132 | moltype = DNA length = 36 |
| FEATURE | Location/Qualifiers |
| misc_feature | 1..36<br>note = Influenza B Neuraminidase conserved region (nucleic acid) |
| source | 1..36<br>mol_type = other DNA<br>organism = synthetic construct |

SEQUENCE: 132
cactttgctt taacccatta tgcagcccaa ccaggg                           36

| | |
|---|---|
| SEQ ID NO: 133 | moltype = AA length = 8 |
| FEATURE | Location/Qualifiers |

```
REGION                        1..8
                              note = misc_feature - Influenza B Neuraminidase conserved
                                region (amino acid)
source                        1..8
                              mol_type = protein
                              organism = synthetic construct
SEQUENCE: 133
DRNKLRHL                                                                              8

SEQ ID NO: 134                moltype = DNA  length = 24
FEATURE                       Location/Qualifiers
misc_feature                  1..24
                              note = Influenza B Neuraminidase conserved region (nucleic
                                acid)
source                        1..24
                              mol_type = other DNA
                              organism = synthetic construct
SEQUENCE: 134
gacagaaaca agctgaggca tcta                                                           24

SEQ ID NO: 135                moltype = AA  length = 10
FEATURE                       Location/Qualifiers
REGION                        1..10
                              note = misc_feature - Influenza B Neuraminidase conserved
                                region (amino acid)
source                        1..10
                              mol_type = protein
                              organism = synthetic construct
SEQUENCE: 135
AWSGSACHDG                                                                           10

SEQ ID NO: 136                moltype = DNA  length = 30
FEATURE                       Location/Qualifiers
misc_feature                  1..30
                              note = Influenza B Neuraminidase conserved region (nucleic
                                acid)
source                        1..30
                              mol_type = other DNA
                              organism = synthetic construct
SEQUENCE: 136
gcatggagcg ggtccgcgtg ccatgatggt                                                     30

SEQ ID NO: 137                moltype = AA  length = 13
FEATURE                       Location/Qualifiers
REGION                        1..13
                              note = misc_feature - Influenza B Neuraminidase conserved
                                region (amino acid)
source                        1..13
                              mol_type = protein
                              organism = synthetic construct
SEQUENCE: 137
KYGEAYTDTY HSY                                                                       13

SEQ ID NO: 138                moltype = DNA  length = 39
FEATURE                       Location/Qualifiers
misc_feature                  1..39
                              note = Influenza B Neuraminidase conserved region (nucleic
                                acid)
source                        1..39
                              mol_type = other DNA
                              organism = synthetic construct
SEQUENCE: 138
aaatatggag aagcatatac tgacacatac cattcctat                                           39

SEQ ID NO: 139                moltype = AA  length = 11
FEATURE                       Location/Qualifiers
REGION                        1..11
                              note = misc_feature - Influenza B Neuraminidase conserved
                                region (amino acid)
source                        1..11
                              mol_type = protein
                              organism = synthetic construct
SEQUENCE: 139
LRTQESACNC I                                                                         11

SEQ ID NO: 140                moltype = DNA  length = 33
FEATURE                       Location/Qualifiers
```

```
misc_feature          1..33
                      note = Influenza B Neuraminidase conserved region (nucleic
                         acid)
source                1..33
                      mol_type = other DNA
                      organism = synthetic construct
SEQUENCE: 140
ctaagaacac aagaaagtgc ctgcaattgc atc                                         33

SEQ ID NO: 141        moltype = AA  length = 10
FEATURE               Location/Qualifiers
REGION                1..10
                      note = misc_feature - Influenza B Neuraminidase conserved
                         region (amino acid)
source                1..10
                      mol_type = protein
                      organism = synthetic construct
SEQUENCE: 141
CRFLKIREGR                                                                   10

SEQ ID NO: 142        moltype = DNA  length = 30
FEATURE               Location/Qualifiers
misc_feature          1..30
                      note = Influenza B Neuraminidase conserved region (nucleic
                         acid)
source                1..30
                      mol_type = other DNA
                      organism = synthetic construct
SEQUENCE: 142
tgcagatttc ttaagattcg agagggccga                                             30

SEQ ID NO: 143        moltype = AA  length = 10
FEATURE               Location/Qualifiers
REGION                1..10
                      note = misc_feature - Influenza B Neuraminidase conserved
                         region (amino acid)
source                1..10
                      mol_type = protein
                      organism = synthetic construct
SEQUENCE: 143
HTEECTCGFA                                                                   10

SEQ ID NO: 144        moltype = DNA  length = 30
FEATURE               Location/Qualifiers
misc_feature          1..30
                      note = Influenza B Neuraminidase conserved region (nucleic
                         acid)
source                1..30
                      mol_type = other DNA
                      organism = synthetic construct
SEQUENCE: 144
cacactgagg aatgcacatg cggatttgcc                                             30

SEQ ID NO: 145        moltype = AA  length = 10
FEATURE               Location/Qualifiers
REGION                1..10
                      note = misc_feature - Influenza B Neuraminidase conserved
                         region (amino acid)
source                1..10
                      mol_type = protein
                      organism = synthetic construct
SEQUENCE: 145
YTAKRPFVKL                                                                   10

SEQ ID NO: 146        moltype = DNA  length = 30
FEATURE               Location/Qualifiers
misc_feature          1..30
                      note = Influenza B Neuraminidase conserved region (nucleic
                         acid)
source                1..30
                      mol_type = other DNA
                      organism = synthetic construct
SEQUENCE: 146
tacacagcaa aaagaccttt tgtcaaatta                                             30

SEQ ID NO: 147        moltype = AA  length = 8
FEATURE               Location/Qualifiers
```

```
REGION                      1..8
                            note = misc_feature - Influenza B Neuraminidase conserved
                              region (amino acid)
source                      1..8
                            mol_type = protein
                            organism = synthetic construct
SEQUENCE: 147
KGGFVHQR                                                                            8

SEQ ID NO: 148              moltype = DNA  length = 24
FEATURE                     Location/Qualifiers
misc_feature                1..24
                            note = Influenza B Neuraminidase conserved region (nucleic
                              acid)
source                      1..24
                            mol_type = other DNA
                            organism = synthetic construct
SEQUENCE: 148
aagggaggat tgttcatca aaga                                                          24

SEQ ID NO: 149              moltype = AA  length = 7
FEATURE                     Location/Qualifiers
REGION                      1..7
                            note = misc_feature - Influenza B Neuraminidase conserved
                              region (amino acid)
source                      1..7
                            mol_type = protein
                            organism = synthetic construct
SEQUENCE: 149
GRWYSRT                                                                             7

SEQ ID NO: 150              moltype = DNA  length = 21
FEATURE                     Location/Qualifiers
misc_feature                1..21
                            note = Influenza B Neuraminidase conserved region (nucleic
                              acid)
source                      1..21
                            mol_type = other DNA
                            organism = synthetic construct
SEQUENCE: 150
ggaaggtggt actctcgaac g                                                            21

SEQ ID NO: 151              moltype = AA  length = 10
FEATURE                     Location/Qualifiers
REGION                      1..10
                            note = misc_feature - Influenza B Neuraminidase conserved
                              region (amino acid)
source                      1..10
                            mol_type = protein
                            organism = synthetic construct
SEQUENCE: 151
EPGWYSFGFE                                                                         10

SEQ ID NO: 152              moltype = DNA  length = 30
FEATURE                     Location/Qualifiers
misc_feature                1..30
                            note = Influenza B Neuraminidase conserved region (nucleic
                              acid)
source                      1..30
                            mol_type = other DNA
                            organism = synthetic construct
SEQUENCE: 152
gaacctggtt ggtattcctt tggcttcgaa                                                   30

SEQ ID NO: 153              moltype = AA  length = 7
FEATURE                     Location/Qualifiers
REGION                      1..7
                            note = misc_feature - Influenza B Neuraminidase conserved
                              region (amino acid)
source                      1..7
                            mol_type = protein
                            organism = synthetic construct
SEQUENCE: 153
EMVHDGG                                                                             7

SEQ ID NO: 154              moltype = DNA  length = 21
FEATURE                     Location/Qualifiers
```

```
misc_feature           1..21
                       note = Influenza B Neuraminidase conserved region (nucleic
                        acid)
source                 1..21
                       mol_type = other DNA
                       organism = synthetic construct
SEQUENCE: 154
gagatggtac atgatggtgg a                                              21

SEQ ID NO: 155         moltype = AA  length = 8
FEATURE                Location/Qualifiers
REGION                 1..8
                       note = misc_feature - H1N1 Neuraminidase conserved region
                        (amino acid)
source                 1..8
                       mol_type = protein
                       organism = synthetic construct
SEQUENCE: 155
GAVAVLKY                                                             8

SEQ ID NO: 156         moltype = DNA  length = 24
FEATURE                Location/Qualifiers
misc_feature           1..24
                       note = H1N1 Neuraminidase conserved region (nucleic acid)
source                 1..24
                       mol_type = other DNA
                       organism = synthetic construct
SEQUENCE: 156
ggggcagtgg ctgtgttaaa gtac                                           24

SEQ ID NO: 157         moltype = AA  length = 566
FEATURE                Location/Qualifiers
REGION                 1..566
                       note = misc_feature - Variant of H1N1 Hemagglutinin
                        A/Michigan/45/2015 strain (amino acid) GenBank: MK622940.1
                        Hypervariable residues substituted with Ala
source                 1..566
                       mol_type = protein
                       organism = synthetic construct
SEQUENCE: 157
MKAILVVLLY TFAAANADTL CIGYHANNST DTVDTVLEKN VTVTHSVNLL EAAHNGKLCK    60
LRGVAPLHLG KCNIAGWALG NPECEALATA SSWSYIVETS ASDNGTCYPG DFIAYEELRE    120
QLSSVSSFER FEIFPKASSW PNHDANAGVT AACPAAGAAA FYANLIWLVK KGNSYPKAAA    180
SYINAKAKEV LVLWAIHHPA TAADQQSLYQ NADAYVFVGA SAYSAKFAPE IAARPKVRAQ    240
AGRMNYYWTL AEPGDAITFE ATGNLVVPRY AFAAARAAGS GIIISDAAVH DCATTCQTPA    300
GAINTSLPFQ NIHPATIGAC PKYVKSTKLR AATGLRNAPS IQSRGLFGAI AGFIEGGWTG    360
MADGWYGYHH QNEQGSGYAA DAKSTQNAID AITNKVNSVI EKMNTQFTAV GKEFAHLEAR    420
IENLNKKVDD GFLDIWTYNA ELLVLLENER TLDYHDSNVK NLYEKVRAQL KNNAKEIGNG    480
CFEFYHKCDA ACMESVKNGT YDYPKYSEEA KLNREAIDGV KLESTRIYQI LAIYSTVASS    540
LVLAVSLGAI SFWMCSNGSL QCRICI                                         566

SEQ ID NO: 158         moltype = AA  length = 85
FEATURE                Location/Qualifiers
REGION                 1..85
                       note = misc_feature - Influenza A H1N1 Hemagglutinin 2009
                        residues 145-229
source                 1..85
                       mol_type = protein
                       organism = synthetic construct
SEQUENCE: 158
SNKGVTAACP HAGAKSFYKN LIWLVKKGNS YPKLSKSYIN DKGKEVLVLW GIHHPSTSAD    60
QQSLYQNADA YVFVGSSRYS KKFKP                                          85

SEQ ID NO: 159         moltype = AA  length = 85
FEATURE                Location/Qualifiers
REGION                 1..85
                       note = misc_feature - Influenza A H1N1 Hemagglutinin 2010
                        residues 145-229
source                 1..85
                       mol_type = protein
                       organism = synthetic construct
SEQUENCE: 159
SNKGVTAACP HAGAKSFYKN LIWLVKKGNS YPKLSKSYIN DKGKEVLVLW GIHHPPTSAD    60
QQSLYQNADA YVFVGTSRYS KKFKP                                          85

SEQ ID NO: 160         moltype = AA  length = 85
FEATURE                Location/Qualifiers
```

```
REGION                    1..85
                          note = misc_feature - Influenza A H1N1 Hemagglutinin 2011
                            residues 145-229
source                    1..85
                          mol_type = protein
                          organism = synthetic construct
SEQUENCE: 160
TTRGTTVACS HSGANSFYRN LLWIVKKGNS YPKLSKSYTN NKGKEVLVIW GVHHPPTDSD    60
QQTLYQNNHT YVSVGSSKYY KRLTP                                          85

SEQ ID NO: 161            moltype = AA   length = 85
FEATURE                   Location/Qualifiers
REGION                    1..85
                          note = misc_feature - Influenza A H1N1 Hemagglutinin 2012
                            residues 145-229
source                    1..85
                          mol_type = protein
                          organism = synthetic construct
SEQUENCE: 161
SNKGVTAACP HAGAKGFYKN LIWLVKKGNS YPKLSKSYIN DKGKEVLVLW GIHHPSTTAD    60
QQSLYQNADT YVFVGTSRYS KKFKP                                          85

SEQ ID NO: 162            moltype = AA   length = 85
FEATURE                   Location/Qualifiers
REGION                    1..85
                          note = misc_feature - Influenza A H1N1 Hemagglutinin 2013
                            residues 145-229
source                    1..85
                          mol_type = protein
                          organism = synthetic construct
SEQUENCE: 162
SNKGVTAACP HAGAKSFYKN LIWLVKKGNS YPKLSKSYIN DKGKEVLVLW GIHHPSTTAD    60
QQSLYQNANA YVFVGTSKYS KKFKP                                          85

SEQ ID NO: 163            moltype = AA   length = 85
FEATURE                   Location/Qualifiers
REGION                    1..85
                          note = misc_feature - Influenza A H1N1 Hemagglutinin 2014
                            residues 145-229
source                    1..85
                          mol_type = protein
                          organism = synthetic construct
SEQUENCE: 163
SNKGVTAACP HAGAKSFYKN LIWLVKKGNS YPKLSKSYIN DKGKEVLVLW GIHHPSTSAD    60
QQSLYQNADA YVFVGTSRYS KKFKP                                          85

SEQ ID NO: 164            moltype = AA   length = 85
FEATURE                   Location/Qualifiers
REGION                    1..85
                          note = misc_feature - Influenza A H1N1 Hemagglutinin 2015
                            residues 145-229
source                    1..85
                          mol_type = protein
                          organism = synthetic construct
SEQUENCE: 164
SNKGVTAACP HAGAKSFYKN LIWLVKKGNS YPKLSKSYIN DKGKEVLVLW GIHHPSTSAD    60
QQSLYQNADA YVFVGTSRYS KKFKP                                          85

SEQ ID NO: 165            moltype = AA   length = 85
FEATURE                   Location/Qualifiers
REGION                    1..85
                          note = misc_feature - Influenza A H1N1 Hemagglutinin 2016
                            residues 145-229
source                    1..85
                          mol_type = protein
                          organism = synthetic construct
SEQUENCE: 165
SNKGVTAACP HAGAKSFYKN LIWLVKKGNS YPKLNQSYIN DKGKEVLVLW GIHHPSTTAD    60
QQSLYQNADA YVFVGTSRYS KKFKP                                          85

SEQ ID NO: 166            moltype = AA   length = 85
FEATURE                   Location/Qualifiers
REGION                    1..85
                          note = misc_feature - Influenza A H1N1 Hemagglutinin 2017
                            residues 145-229
source                    1..85
                          mol_type = protein
                          organism = synthetic construct
```

```
SEQUENCE: 166
SNKGVTAACP HAGAKSFYKN LIWLVKKGNS YPKLNQTYIN DKGKEVLVLW GIHHPPTTAD   60
QQSLYQNADA YVFVGTSRYS KKFKP                                        85

SEQ ID NO: 167          moltype = AA  length = 85
FEATURE                 Location/Qualifiers
REGION                  1..85
                        note = misc_feature - Influenza A H1N1 Hemagglutinin 2018
                          residues 145-229
source                  1..85
                        mol_type = protein
                        organism = synthetic construct
SEQUENCE: 167
SDKGVTAACP HAGAKSFYKN LIWLVKKGNS YPKLNQTYIN DKGKEVLVLW GIHHPPTIAD   60
QQSLYQNADA YVFVGTSRYS KKFKP                                        85

SEQ ID NO: 168          moltype = AA  length = 85
FEATURE                 Location/Qualifiers
REGION                  1..85
                        note = misc_feature - Influenza A H1N1 Hemagglutinin 2019
                          residues 145-229
source                  1..85
                        mol_type = protein
                        organism = synthetic construct
SEQUENCE: 168
SNKGVTAACP HAGAKSFYKN LIWLVKKGNS YPKINQTYIN DKGKEVLVLW GIHHPPTTAD   60
QQSLYQNADA YVFVGTSRYS KKFKP                                        85

SEQ ID NO: 169          moltype = DNA  length = 1701
FEATURE                 Location/Qualifiers
misc_feature            1..1701
                        note = H1N1 Hemagglutinin A/Michigan/45/2015 strain
                          (nucleotide) GenBank: MK622940.1
source                  1..1701
                        mol_type = other DNA
                        organism = synthetic construct
SEQUENCE: 169
atgaaggcaa tactagtagt tctgctatat acatttacaa ccgcaaatgc agacacatta   60
tgtataggtt atcatgcgaa caattcaaca gacactgtag acacagtact agaaaagaat  120
gtaacagtaa cacactctgt taaccttctg gaagacaagc ataacggaaa actatgcaaa  180
ctaagagggg tagccccatt gcatttgggt aaatgtaaca ttgctggctg gatcctggga  240
aatccagagt gtgaatcrct ctccacagca agttcatggt cctacattgt ggaaacatct  300
aattcagaca atggaacgtg ttacccagga gatttcatca attatgagga gctaagagag  360
caattgagct cagtgtcatc atttgaaagg tttgagatat ccccaagac aagttcatgg  420
cccaatcatg actcgaacaa aggtgtaacg gcagcatgtc ctcacgctgg agcaaaaagc  480
ttctacaaaa acttgatatg gctagttaaa aaggaaatt catacccaaa gcttaaccaa  540
tcctacatta tgataaagg gaaagaagtc ctcgtgctgt ggggcattca ccatccatct  600
actactgctg accaacaaag tctctatcag aatgcagatg catatgtttt tgtggggaca  660
tcaagataca gcaagaagtt caagccggaa atagcaacaa gacccaaagt gagggatcaa  720
gaagggagaa tgaactatta ctggacacta gtagagccgg gagacaaaat aacattcgaa  780
gcaactggaa atctagtggt accgagatat gcattccaaa tggaaagaaa tgctggatcc  840
ggtattatca tttcagatac accagtccac gattgcaata caacttgtca gacacccgag  900
ggtgctataa acaccagcct cccatttcag aatatacatc cgatcacaat tggaaaatgt  960
ccaaagtatg taaaaagcac aaaattgaga ctggccacag gattgaggaa tgttccgtct 1020
attcaatcta gaggcctatt cggggccatt gccggcttca ttgaagggggg gtggacaggg 1080
atggtagatg gatggtacgg ttatcaccat caaaatgagc aggggtcagg atatgcagcc 1140
gacctgaaga gcacacaaaa tgccattgac aagattacta acaaagtaaa ttctgttatt 1200
gaaaagatga atacacagtt cacagcagtg gtaaagagt caaccacctg gaaaaagaga 1260
atagagaatc taaataaaaa agttcctgg acatttggag ttacaatgcc 1320
gaactgttgg ttctattgga aaatgaaaga actttggact atcacgattc aaatgtgaag 1380
aacttgtatg aaaaagtaag aaaccagtta aaaacaatg ccaaggaaat ggaaacggc 1440
tgctttgaat tttaccacaa atgcgataac acgtgcatgg aaagtgtcaa aaatgggact 1500
tatgactacc caaaatactc agaggaagca aaattaaca gagaaaaaat agtgggta 1560
aagctggaac caacaaggat ttaccagatt ttggcgatct attcaactgt cgccagttca 1620
ttggtactgg tagtctccct gggggcaatc agcttctgga tgtgctctaa tgggtctcta 1680
cagtgtagaa tatgtattta a                                          1701

SEQ ID NO: 170          moltype = DNA  length = 1701
FEATURE                 Location/Qualifiers
misc_feature            1..1701
                        note = Variant of H1N1 Hemagglutinin A/Michigan/45/2015
                          strain (nucleotide) GenBank: MK622940.1 Hypervariable
                          residues substituted with Ala
source                  1..1701
                        mol_type = other DNA
                        organism = synthetic construct
SEQUENCE: 170
atgaaggcaa tactagtagt tctgctatat acatttgcag ccgcaaatgc agacacatta   60
tgtataggtt atcatgcgaa caattcaaca gacactgtag acacagtact agaaaagaat  120
```

-continued

```
gtaacagtaa cacactctgt taaccttctg gaagccgcgc ataacggaaa actatgcaaa  180
ctaagagggg tagccccatt gcatttgggt aaatgtaaca ttgctggctg ggccctggga  240
aatccagagt gtgaagcrct cgccacagca agttcatggt cctacattgt ggaaacatct  300
gcttcagaca atggaacgtg ttacccagga gatttcatcg cttatgagga gctaagagag  360
caattgagct cagtgtcatc atttgaaagg tttgagatat tccccaaggc aagttcatgg  420
cccaatcatg acgcgaacgc aggtgtaacg gcagcatgtc ctgccgctgg agcagcagcc  480
ttctacgcaa acttgatatg gctagttaaa aaaggaaatt catacccaaa ggctgccgca  540
tcctacatta atgctaaagc gaaagaagtc ctcgtgctgt gggccattca ccatccagct  600
actgctgctg accaacaaag tctctatcag aatgcagatg catatgtttt tgtggggaca  660
tcagcataca gcgcgaagtt cgcgccggaa atagcagcaa gacccaaagt gagggctcaa  720
gcagggagaa tgaactatta ctggacacta gcagagccgg gagacgcaat aacattcgaa  780
gcaactggaa atctagtggt accgagatat gcattcgcag cggcaagagc tgctggatct  840
ggtattatca tttcagatgc agcagtccac gattgcgcta caacttgtca gacacccgcg  900
ggtgctataa acaccagcct cccatttcag aatatacatc cggccacaat tggagcatgt  960
ccaaagtatg taaaaagcac aaaattgaga gcggccacag gattgaggaa tgctccgtct  1020
attcaatcta gaggcctatt cggggccatt gccggcttca ttgaaggggg gtggacaggg  1080
atggcagatg gatggtacgg ttatcaccat caaaatgagc aggggtcagg atatgcagcc  1140
gacgcgaaga gcacacaaaa tgccattgac gcgattacta acaaagtaaa ttctgttatt  1200
gaaaagatga atacacagtt cacagcagtg ggtaaagagt tcgcccacct ggaagcaaga  1260
atagagaatc taaataaaaa agttgatgat ggtttcctgg acatttggac ttacaatgcc  1320
gaactgttgg ttctattgga aaatgaaaga actttggact atcacgattc aaatgtgaag  1380
aacttgtatg aaaaagtaag agcccagtta aaaaacaatg ccaaggaaat tggaaacggc  1440
tgctttgaat tttaccacaa atgcgatgcc gcgtgcatgg aaagtgtcaa aaatgggact  1500
tatgactacc caaaatactc agaggaagca aaattaaaca gagaagcaat agatggggta  1560
aagctggaat caacaaggat ttaccagatt ttggcgatct attcaactgt cgccagttca  1620
ttggtactgg cagtctccct gggggcaatc agcttctgga tgtgctctaa tgggtctcta  1680
cagtgtagaa tatgtattta a                                            1701

SEQ ID NO: 171          moltype = AA  length = 252
FEATURE                 Location/Qualifiers
REGION                  1..252
                        note = misc_feature - H3N2 M1 Protein
source                  1..252
                        mol_type = protein
                        organism = synthetic construct
SEQUENCE: 171
MSLLTEVETY VLSIVPSGPL KAEIAQRLED VFAGKNTDLE ALMEWLKTRP ILSPLTKGIL  60
GFVFTLTVPS ERGLQRRRFV QNALNGNGDP NNMDKAVKLY RKLKREITFH GAKEIALSYS  120
AGALASCMGL IYNRMGAVTT EVAFGLVCAT CEQIADSQHR SHRQMVATTN PLIKHENRMV  180
LASTTAKAME QMAGSSEQAA EAMEIASQAR QMVQAMRAIG THPSSSTGLR DDLLENLQTY  240
QKRMGVQMQR FK                                                      252

SEQ ID NO: 172          moltype = AA  length = 121
FEATURE                 Location/Qualifiers
REGION                  1..121
                        note = misc_feature - H3N2 NEP Protein
source                  1..121
                        mol_type = protein
                        organism = synthetic construct
SEQUENCE: 172
MDSNTVSSFQ DILLRMSKMQ LGSSSEDLNG MITQFESLKI YRDSLGEAVM RMGDLHLLQN  60
RNGKWREQLG QKFEEIRWLI EEVRHRLRTT ENSFEQITFM QALQLLFEVE QEIRTFSFQL  120
I                                                                  121

SEQ ID NO: 173          moltype = AA  length = 498
FEATURE                 Location/Qualifiers
REGION                  1..498
                        note = misc_feature - H3N2 NP Protein
source                  1..498
                        mol_type = protein
                        organism = synthetic construct
SEQUENCE: 173
MASQGTKRSY EQMETDGDRQ NATEIRASVG KMIDGIGRFY IQMCTELKLS DHEGRLIQNS  60
LTIEKMVLSA FDERRNKYLE EHPSAGKDPK KTGGPIYRRV DGKWMRELVL YDKEEIRRIW  120
RQANNGEDAT SGLTHIMIWH SNLNDATYQR TRALVRTGMD PRMCSLMQGS TLPRRSGAAG  180
AAVKGIGTMV MELIRMVKRG INDRNFWRGE NGRKTRSAYE RMCNILKGKF QTAAQRAMVD  240
QVRESRNPGN AEIEDLIFLA RSALILRGSV AHKSCLPACA YGPAVSSGYD FEKEGYSLVG  300
IDPFKLLQNS QIYSLIRPNE NPAHKSQLVW MACHSAAFED LRLLSFIRGT KVSPRGKLST  360
RGVQIASNEN MDNMGSSTLE LRSGYWAIRT RSGGNTNQQR ASAGQTSVQP TFSVQRNLPF  420
EKSTIMAAFT GNTEGRTSDM RAEIIRMMEG AKPEEVSFRG RGVFELSDEK ATNPIVPSFD  480
MSNEGSYFFG DNAEEYDN                                                498

SEQ ID NO: 174          moltype = AA  length = 217
FEATURE                 Location/Qualifiers
REGION                  1..217
                        note = misc_feature - H3N2 NS1 Protein
source                  1..217
                        mol_type = protein
                        organism = synthetic construct
```

```
SEQUENCE: 174
MDSNTVSSFQ VDCFLWHIRK QVVDQKLSDA PFLDRLRRDQ RSLRGRGNTL GLDIKAATHV    60
GKQIVEKILK EESDEALKMT MVSTPASRYI TDMTIEELSR NWFMLMPKQK VEGPLCIRMD   120
QAIMEKNIML KANFNVIFGR LETIVLLRAF TEEGAIVGEI SPLPSFPGHT IEDVKNAIGV   180
LIGGLEWNDN TVRVSKNLQR FAWRSSNENG GPPLTPK                            217

SEQ ID NO: 175          moltype = AA  length = 121
FEATURE                 Location/Qualifiers
REGION                  1..121
                        note = misc_feature - H3N2 NS2 Protein
source                  1..121
                        mol_type = protein
                        organism = synthetic construct
SEQUENCE: 175
MDSNTVSSFQ DILLRMSKMQ LGSSSEDLNG MITQFESLKI YRDSLGEAVM RMGDLHLLQN    60
RNGKWREQLG QKFEEIRWLI EEVRHRLKTT ENSFEQITFM QALQLLFEVE QEIRTFSFQL   120
I                                                                   121

SEQ ID NO: 176          moltype = AA  length = 716
FEATURE                 Location/Qualifiers
REGION                  1..716
                        note = misc_feature - H3N2 PA Protein
source                  1..716
                        mol_type = protein
                        organism = synthetic construct
SEQUENCE: 176
MEDFVRQCFN PMIVELAEKA MKEYGEDLKI ETNKFAAICT HLEVCFMYSD FHFINEQGES    60
IVVELDDPNA LLKHRFEIIE GRDRTMAWTV VNSICNTTGA GKPKFLPDLY DYKENRFIEI   120
GVTRREVHIY YLEKANKIKS ENTHIHIFSF TGEEMATKAD YTLDEESRAR IKTRLFTIRQ   180
EMANRGLWDS FRQSERGEET IEEKFEITGT MRRLADQSLP PNFSCLENFR AYVDGFEPNG   240
CIEGKLSQMS KEVNAQIEPF LKTTPRPIKL PSGPPCYQRS KFLLMDALKL SIEDPSHEGE   300
GIPLYDAIKC IKTFFGWKEP YIVKPHEKGI NSNYLLSWKQ VLSELQDIEN EEKIPRTKNM   360
KKTSQLKWAL GENMAPEKVD FENCRDISDL KQYDSEEPEL RSLSSWIQSE FNKACELTDS   420
VWIELDEIGE DVAPIEHIAS MRRNYFTAEV SHCRATEYIM KGVYINTALL NASCAAMDDF   480
QLIPMISKCR TKEGRRKTNL YGFIIKGRSH LRNDTDVVNF VSMEFSLTDP RLEPHKWEKY   540
CVLEIGDMLL RSAIGQISRP MFLYVRTNGT SKVKMKWGME MRRCLLQSLQ QIESMIEAES   600
SVKEKDMTKE FFENKSEAWP IGESPKGVEE GSIGKVCRTL LAKSVFNSLY ASPQLEGFSA   660
ESRKLLLIVQ ALRDKLEPGT FDLGGLYEAI EECLINDPWV LLNASWFNSF LTHALK       716

SEQ ID NO: 177          moltype = AA  length = 252
FEATURE                 Location/Qualifiers
REGION                  1..252
                        note = misc_feature - H3N2 PA-X Protein
source                  1..252
                        mol_type = protein
                        organism = synthetic construct
SEQUENCE: 177
MEDFVRQCFN PMIVELAEKA MKEYGEDLKI ETNKFAAICT HLEVCFMYSD FHFINEQGES    60
IVVELDDPNA LLKHRFEIIE GRDRTMAWTV VNSICNTTGA GKPKFLPDLY DYKENRFIEI   120
GVTRREVHIY YLEKANKIKS ENTHIHIFSF TGEEMATKAD YTLDEESRAR IKTRLFTIRQ   180
EMANRGLWDS FVSPKEAKKQ LKKNLKSQEL CAGLPTKVSH RTSPALRILE PMWMDSNRTA   240
ALRASFLKCP KK                                                       252

SEQ ID NO: 178          moltype = AA  length = 757
FEATURE                 Location/Qualifiers
REGION                  1..757
                        note = misc_feature - H3N2 PB1 Protein
source                  1..757
                        mol_type = protein
                        organism = synthetic construct
SEQUENCE: 178
MDVNPTLLFL KVPAQNAIST TFPYTGDPPY SHGTGTGYTM DTVNRTHQYS ERGKWTTNTE    60
TGAPQLNPID GPLPEDNEPS GYAQTDCVLE AMAFLEESHP GIFENSCLET MEAVQQTRVD   120
KLTQGRQTYD WTLNRNQPAA TALANTIEVF RSNGLTANES GRLIDFLKDV MESMSQKEEME  180
ITTHFQRKRR VRDNMTKKMV TQRTIGKKKQ RVNKRGYLIR ALTLNTMTKD AERGKLKRRA   240
IATPGMQIRG FVYFVETLAR SICEKLEQSG LPVGGNEKKA KLANVVRKMM TNSQDTELSF   300
TITGDNTKWN ENQNPRMFLA MITYITKNQP EWFRNILSIA PIMFSNKMAR LGKGYMFESK   360
RMKLRTQIPA EMLASIDLKY FNESTRKKIE KIRPLLIDGT ASLSPGMMMG MFNMLSTVLG   420
VSILNLGQKK YTKTTYWWDG LQSSDDFALI VNAPNHEGIQ AGVDRFYRTC KLVGINMSKK   480
KSYINKTGTF EFTSFFYRYG FVANFSMELP SFGVSGINES ADMSIGVTVI KNNMINNDLG   540
PATAQMALQL FIKDYRYTYR CHRGDTQIQT RRSFEIKKLW DQTQSRTGLL VSDGGPNLYN   600
IRNLHIPEVC LKWELMDENY RGRLCNPLNP FVSHKEIESV NNAVVMPAHG PAKSMEYDAV   660
ATTHSWIPKR NRSILNTSQR GILEDEQMYQ KCCNLFEKFF PSSSYRRPIG ISSMVEAMVS   720
RARIDARIDF ESGRIKKEEF SEIMKICSTI EELRRQK                            757

SEQ ID NO: 179          moltype = AA  length = 759
FEATURE                 Location/Qualifiers
REGION                  1..759
                        note = misc_feature - H3N2 PB2 Protein
```

```
source                 1..759
                       mol_type = protein
                       organism = synthetic construct
SEQUENCE: 179
MERIKELRNL MSQSRTREIL TKTTVDHMAI IKKYTSGRQE KNPSLRMKWM MAMKYPITAD  60
KRITEMVPER NEQGQTLWSK MSDAGSDRVM VSPLAVTWWN RNGPVTSTVH YPKVYKTYFD  120
KVERLKHGTF GPVHFRNQVK IRRRVDINPG HADLSAKEAQ DVIMEVVFPN EVGARILTSE  180
SQLTITKEKK EELRDCKISP LMVAYMLERE LVRKTRFLPV AGGTSSIYIE VLHLTQGTCW  240
EQMYTPGGGV RNDDVDQSLI IAARNIVRRA AVSADPLASL LEMCHSTQIG GTRMVDILRQ  300
NPTEEQAVDI CKAAMGLRIS SSFSFGGFTF KRTSGSSVKK EEEVLTGNLQ TLRIRVHEGY  360
EEFTMVGKRA TAILRKATRR LVQLIVSGRD EQSIAEAIIV AMVFSQEDCM IKAVRGDLNF  420
VNRANQRLNP MHQLLRHFQK DAKVLFQNWG VEHIDSVMGM VGVLPDMTPS TEMSMRGIRV  480
SKMGVDEYSS TERVVVSIDR FLRVRDQRGN VLLSPEEVSE TQGTERLTIT YSSSMMWEIN  540
GPESVLVNTY QWIIRNWEAV KIQWSQNPAM LYNKMEFEPF QSLVPKATRS QYSGFVRTLF  600
QQMRDVLGTF DTAQIIKLLP FAAAPPKQSR MQFSSLTVNV RGSGMRILVR GNSPVFNYNK  660
TTKRLTILGK DAGTLIEDPD ESTSGVESAV LRGFLIIGKE DRRYGPALSI NELSNLAKGE  720
KANVLIGQGD VVLVMKRKRD SSILTDSQTA TKRIRMAIN                        759

SEQ ID NO: 180         moltype = AA  length = 109
FEATURE                Location/Qualifiers
REGION                 1..109
                       note = misc_feature - Influenza B bm2 Protein
source                 1..109
                       mol_type = protein
                       organism = synthetic construct
SEQUENCE: 180
MLEPFQILSI CSFILSALHF MAWTIGHLNQ IKRGVNMKIR IKGPNKETIN REVSILRHSY  60
QKEIQAKEAM KEVLSDNMEV LSDHIVIEGL SAEEIIKMGE TVLEVEELH             109

SEQ ID NO: 181         moltype = AA  length = 248
FEATURE                Location/Qualifiers
REGION                 1..248
                       note = misc_feature - Influenza B bm1 Protein
source                 1..248
                       mol_type = protein
                       organism = synthetic construct
SEQUENCE: 181
MSLFGDTIAY LLSLTEDGEG KAELAEKLHC WFGGKEFDLD SALEWIKNKR CLTDIQKALI  60
GASICFLKPK DQERKRRFIT EPLSGMGTTA TKKKGLILAE RKMRKCVSFH EAFEIAEGHE  120
SSALLYCLMV MYLNPGNYSM QVKLGTLCAL CEKQASHSHR AHSRAARSSV PGVRREMQMV  180
SAMNTAKTMN GMGKGEDVQK LAEELQSNIG VLRSLGASQK NGEGIAKDVM EVLKQSSMGN  240
SALVKKYL                                                          248

SEQ ID NO: 182         moltype = AA  length = 122
FEATURE                Location/Qualifiers
REGION                 1..122
                       note = misc_feature - Influenza B nep Protein
source                 1..122
                       mol_type = protein
                       organism = synthetic construct
SEQUENCE: 182
MADNMTTTQI EWRMKKMAIG SSIHSSSVLM KDIQSQFEQL KLRWESYPNL VKSTDYHQKR  60
ETIRLVTEEL YLLSKRIDDN ILFHKTVIAN SSIIADMVVS LSLLETLYEM KDVVEVYSRQ  120
CL                                                                122

SEQ ID NO: 183         moltype = AA  length = 281
FEATURE                Location/Qualifiers
REGION                 1..281
                       note = misc_feature - Influenza B ns1 Protein
source                 1..281
                       mol_type = protein
                       organism = synthetic construct
SEQUENCE: 183
MADNMTTTQI EVGPGATNAT INFEAGILEC YERLSWQRAL DYPGQDRLNR LKRKLESRIK  60
THNKSEPESK RMSLEERKAI GVKMMKVLLF MNPSAGIEGF EPYCMKSSSN SNCPKYNWTD  120
YPSTPGRCLD DIEEEPDDVD GPTEIVLRDM NNKDARQKIK EEVNTQKEGK FRLTIKRDMR  180
NVLSLRVLVN GTFLKHPNGY KSLSTLHRLN AYDQSGRLVA KLVATDDLTV EDEEDGHRIL  240
NSLFERLNEG HSKPIRAAET AVGVLSQFGQ EHRLSPEEGD N                     281

SEQ ID NO: 184         moltype = AA  length = 122
FEATURE                Location/Qualifiers
REGION                 1..122
                       note = misc_feature - Influenza B ns2 Protein
source                 1..122
                       mol_type = protein
                       organism = synthetic construct
```

```
SEQUENCE: 184
MADNMTTTQI EWRMKKMAIG SSTHSSSVLM KDIQSQFEQL KLRWESYPNL VKSTDYHQKR    60
ETIRLVTEEL YLLSKRIDDN ILFHKTVIAN SSIIADMVVS LSLLETLYEM KDVVEVYSRQ   120
CL                                                                 122

SEQ ID NO: 185          moltype = AA   length = 726
FEATURE                 Location/Qualifiers
REGION                  1..726
                        note = misc_feature - Influenza B pa Protein
source                  1..726
                        mol_type = protein
                        organism = synthetic construct
SEQUENCE: 185
MDTFITRNFQ TTIIQKAKNT MAEFSEDPEL QPAMLFNICV HLEVCYVISD MNFLDEEGKA    60
YTALEGQGKE QNLRPQYEVI EGMPRTIAWM VQRSLAQEHG IETPKYLADL FDYKTKRFIE   120
VGITKGLADD YFWKKKEKLG NSMELMIFSY NQDYSLSNES SLDEEGKGRV LSRLTELQAE   180
LSLKNLWQVL IGEEDVEKGI DFKLGQTISR LRDISVPAGF SNFEGMRSYI DNIDPKGAIE   240
RNLARMSPLV SVTPKKLKWE DLRPIGPHIY NHELPEVPYN AFLLMSDELG LANMTEGKSK   300
KPKTLAKECL EKYSTLRDQT DPILIMKSEK ANENFLWKLW RDCVNTISNE EMSNELQKTN   360
YAKWATGDGL TYQKIMKEVA IDDETMCQEE PKIPNKCRVA AWVQTEMNLL STLTSKRALD   420
LPEIGPDVAP VEHVGSERRK YFVNEINYCK ASTVMMKYVL FHTSLLNESN ASMGKYKVIP   480
ITNRVVNEKG ESFDMLYGLA VKGQSHLRGD TDVVTVVTFE FSSTDPRVDS GKWPKYTVFR   540
IGSLFVSGRE KSVYLYCRVN GTNKIQMKWG MEARRCLLQS MQQMEAIVEQ ESSIQGYDMT   600
KACFKGDRVN SPKTFSIGTQ EGKLVKGSFG KALRVIFTKC LMHYVFGNAQ LEGFSAESRR   660
LLLLIQALKD RKGPWVFDLE GMYSGIEECI SNNPWVIQSA YWFNEWLGFE KEGSKVLESV   720
DEIMDE                                                             726

SEQ ID NO: 186          moltype = AA   length = 752
FEATURE                 Location/Qualifiers
REGION                  1..752
                        note = misc_feature - Influenza B pb1 Protein
source                  1..752
                        mol_type = protein
                        organism = synthetic construct
SEQUENCE: 186
MNINPYFLFI DVPIQAAIST TFPYTGVPPY SHGTGTGYTI DTVIRTHEYS NKGKQYVSDI    60
TGCTMVDPTN GPLPEDNEPS AYAQLDCVLE ALDRMDEEHP GLFQAASQNA MEALMVTTVD   120
KLTQGRQTFD WTVCRNQPAA TALNTTITSF RLNDLNGADK GGLVPFCQDI IDSLDKPEMT   180
FFSVKNIKKK LPAKNRKGFL IKRIPMKVKD RISRVEYIKR ALSLNTMTKD AERGKLKRRA   240
IATAGIQIRG FVLVVENLAK NICENLEQSG LPVGGNEKKA KLSNAVAKML SNCPPGGISM   300
TVTGDNTKWN ECLNPRIFLA MTERITRDSP IWFRDFCSIA PVLFSNKIAR LGKGFMITSK   360
TKRLKAQIPC PDLFSIPLER YNEETRAKLK KLKPFFNEEG TASLSPGMMM GMFNMLSTVL   420
GVAALGIKNI GNKEYLWDGL QSSDDFALFV NAKDEETCME GINDFYRTCK LLGINMSKKK   480
SYCNETGMFE FTSMFYRDGF VSNFAMEIPS FGVAGVNESA DMAIGMTIIK NNMINNGMGP   540
ATAQTAIQLF IADYRYTYKC HRGDSKVEGK RMKIIKELWE NTKGRDGLLV ADGGPNIYNL   600
RNLHIPEIVL KYNLMDPEYK GRLLHPQNPF VGHLSIEGIK EADITPAHGP VKKMDYDAVS   660
GTHSWRTKRN RSILNTDQRN MILEEQCYAK CCNLFEACFN SASYRKPVGQ HSMLEAMAHR   720
LRMDARLDYE SGRMSKDDFE KAMAHLGEIG YT                                752

SEQ ID NO: 187          moltype = AA   length = 770
FEATURE                 Location/Qualifiers
REGION                  1..770
                        note = misc_feature - Influenza B pb2 Protein
source                  1..770
                        mol_type = protein
                        organism = synthetic construct
SEQUENCE: 187
MTLAKIELLK QLLRDNEAKT VLKQTTVDQY NIIRKFNTSR IEKNPSLRMK WAMCSNFPLA    60
LTKGDMANRI PLEYKGIQLK TNAEDIGTKG QMCSIAAVTW WNTYGPIGDT EGFEKVYESF   120
FLRKMRLDNA TWGRITFGPV ERVRKRVLLN PLTKEMPPDE ASNVIMEILF PKEAGIPRES   180
TWIHRELIKE KREKLKGTMI TPIVLAYMLE RELVARRRFL PVAGATSAEF IEMLHCLQGE   240
NWRQIYHPGG NKLTESRSQS MIVACRKIIR RSIVASNPLE LAVEIANKTV IDTEPLKSCL   300
TAIDGGDVAC DIIRAALGLK IRQRQRFGRL ELKRISGRGF KNDEEILIGN GTIQKIGIWD   360
GEEEFHVRCG ECRGILKKSK MRMEKLLINS AKKEDMKDLI ILCMVFSQDT RMFQGVRGEI   420
NFLNRAGQLL SPMYQLQRYF LSRSNDLFDQ WGYEESPKAS ELHGINELMN ASDYTLKGVV   480
VTKNVIDDFS STETEKVSIT KNLSLIKRTG EVIMGANDVS ELESQAQLMI TYDTPKMWEM   540
GTTKELVQNT YQWVLKNLVT LKAQPLLGKE DMFQWDAFEA FESIIPQKMA GQYSGFARAV   600
LKQMRDQEVM KTDQFIKLLP FCFSPPKLRS NGEPYQFLRL VLKGGGENFI EVRKGSPLFS   660
YNPQTEVLTI CGRMMSLKGK IEDEERNRSM GNAVLAGFLV SGKYDPDLGD FKTIEELEKL   720
KPGEKANILL YQGKPVKVVK RKRYSALSND ISQGIKRQRM TVESMGWALS             770

SEQ ID NO: 188          moltype = AA   length = 252
FEATURE                 Location/Qualifiers
REGION                  1..252
                        note = misc_feature - H1N1 M Protein
source                  1..252
                        mol_type = protein
                        organism = synthetic construct
```

```
SEQUENCE: 188
MSLLTEVETY VLSIIPSGPL KAEIAQRLES VFAGKNTDLE ALMEWLKTRP ILSPLTKGIL  60
GFVFTLTVPS ERGLQRRRFI QNALNGNGDP NNMDRAVKLY KKLKREITFH GAKEVSLSYS  120
TGALASCMGL IYNRMGTVTT EAAFGLVCAT CEQIADSQHR SHRQMATTTN PLIRHENRMV  180
LASTTAKAME QVAGSSEQAA EAMEVANQTR QMVHAMRTIG THPSSSAGLR DDLLENLQAY  240
QKRMGVQMQR FK                                                      252

SEQ ID NO: 189          moltype = AA  length = 219
FEATURE                 Location/Qualifiers
REGION                  1..219
                        note = misc_feature - H1N1 ns1 Protein
source                  1..219
                        mol_type = protein
                        organism = synthetic construct
SEQUENCE: 189
MDSNTMSSFQ VDCFLWHIRK RFADNGLGDA PFLDRLRRDQ KSLKGRGNTL GLDIETATLV  60
GKQIVEWILK EESSETLRMT IASVPTSRYL SDMTLEEMSR DWFMLMPRQK IIGPLCVRLD  120
QAIMEKNIVL KANFSVIFNR LETLILLRAF TEEGAIVGEI SPLPSLPGHT YEDVKNAVGV  180
LIGGLEWNGN TVRVSENIQR FAWRNCDENG RPSLPPEQK                         219

SEQ ID NO: 190          moltype = AA  length = 716
FEATURE                 Location/Qualifiers
REGION                  1..716
                        note = misc_feature - H1N1 pa Protein
source                  1..716
                        mol_type = protein
                        organism = synthetic construct
SEQUENCE: 190
MEGFVRQCFN PMIVELAEKA MKEYGEDPKI ETNKFAAICT HLEVCFMYSD FHFIDERGES  60
IIVESGDPNA LLKHRFEIIE GRDRIMAWTV VNSICNTTGV EKPKFLPDLY DYKENRFIEI  120
GVTRREVHIY YLEKANKIKS EKTHIHIFSF TGEEMATKAD YTLDEESRAR IKTRLFTIRQ  180
EMASRSLWDS FRQSERGEET IEEKFEITGT MRKLADQSLP PNFSSLENFR AYVDGFEPNG  240
CIEGKLSQMS KEVNAKIEPF LRTTPRPLRL PDGPLCHQRS KFLLMDALKL SIEDPSHEGE  300
GIPLYDAIKC MKTFFGWKEP NIVKPHEKGI NPNYLMTWKQ VLAELQDIEN EEKIPRTKNM  360
KRTSQLKWAL GENMAPEKVD FDDCKDVGDL KQYDSDEPEP RSLASWVQNE FNKACELTDS  420
SWIELDEIGE DVAPIEHIAS MRRNYFTAEV SHCRATEYIM KGVYINTALL NASCAAMDDF  480
QLIPMISKCR TKEGRRKTNL YGFIIKGRSH LRNDTDVVNF VSMEFSLTDP RLEPHKWEKY  540
CVLEIGDMLL RTAIGQVSRP MFLYVRTNGT SKIKMKWGME MRRCLLQSLQ QIESMIEAES  600
SVKEKDMTKE FFENKSETWP IGESPRGVEE GSIGKVCRTL LAKSVFNSLY ASPQLEGFSA  660
ESRKLLLIVQ ALRDNLEPGT FDLGGLYEAI EECLINDPWV LLNASWFNSF LTHALK      716

SEQ ID NO: 191          moltype = AA  length = 757
FEATURE                 Location/Qualifiers
REGION                  1..757
                        note = misc_feature - H1N1 pb1 Protein
source                  1..757
                        mol_type = protein
                        organism = synthetic construct
SEQUENCE: 191
MDVNPTLLFL KIPAQNAIST TFPYTGDPPY SHGTGTGYTM DTVNRTHQYS EKGKWTTNTE  60
TGAPQLNPID GPLPEDNEPS GYAQTDCVLE AMAFLEESHP GIFENSCLET MEVVQQTRVD  120
KLTQGRQTYD WTLNRNQPAA TALANTIEVF RSNGLTANES GRLIDFLKDV MESMNKEEIE  180
ITTHFQRKRR VRDNMTKKMV TQRTIGKKKQ RLNKRGYLIR ALTLNTMTKD AERGKLKRRA  240
IATPGMQIRG FVYFVETLAR SICEKLEQSG LPVGGNEKKA KLANVVRKMM TNSQDTEISF  300
TITGDNTKWN ENQNPRMFLA MITYITRNQP EWFRNILSMA PIMFSNKMAR LGRGYMFESK  360
RMKIRTQIPA EMLASIDLKY FNESTKKKIE KIRPLLIDGT ASLSPGMMMG MFNMLSTVLG  420
VSILNLGQKK YTKTIYWWDG LQSSDDFALI VNAPNHEGIQ AGVDRFYRTC KLVGINMSKK  480
KSYINKTGTF EFTSFFYRYG FVANFSMELP SFGVSGVNES ADMSIGVTVI KNNMINNDLG  540
PATAQMALQL FIKDYRYTYR CHRGDTQIQT RRSFELKKLW DQTQSKVGLL VSDGGPNLYN  600
IRNLHIPEVC LKWELMDDDY RGRLCNPLNP FVSHKEIDSV NNAVVMPAHG PAKSMEYDAV  660
ATTHSWIPKR NRSILNTSQR GILEDEQMYQ KCCNLFEKFF PSSSYRRPVG ISSMVEAMVS  720
RARIDARVDF ESGRIKKEEF SEIMKICSTI EELRRQK                           757

SEQ ID NO: 192          moltype = AA  length = 446
FEATURE                 Location/Qualifiers
REGION                  1..446
                        note = misc_feature - H1N1 pb2 Protein
source                  1..446
                        mol_type = protein
                        organism = synthetic construct
SEQUENCE: 192
AMGLRISSSF SFGGFTFKRT SGSSVKREEE VLTGNLQTLK LTVHEGYEEF TMVGKRATAI  60
LRKATRRLIQ LIVSGRDEQS IVEAIVVAMV FSQEDCMVKA VRGDLNFVNR ANQRLNPMHQ  120
LLRHFQKDAK VLFLNWGVEP IDNVMGMIGI LPDMTPSTEM SMRGVRVSKM GVDEYSNAER  180
VVVSIDRFLR VRDQRGNVLL SPEEVSETQG TEKLTITYSS SMMWEINGPE SVLINTYQWI  240
IRNWETVKIQ WSQNPTMLYN KMEFEPFQSL VPKAIRGQYS GFVRTLFQQM RDVLGTFDTT  300
QIIKLLPFAA APPKQSRMQF SSLTVNVRGS GMKILVRGNS PVFNYNKTTK RLTVLGKDAG  360
TLTEDPDEGT AGVESAVLRG FLILGKEDRR YGPALSINEL SNLAKGEKAN VLIGQGDVVL  420
VMKRKRDSSI LTDSQTATKR IRMAIN                                       446
```

```
SEQ ID NO: 193        moltype = AA  length = 121
FEATURE               Location/Qualifiers
REGION                1..121
                      note = misc_feature - H1N1 NS2 Protein
source                1..121
                      mol_type = protein
                      organism = synthetic construct
SEQUENCE: 193
MDSNTMSSFQ DILMRMSKMQ LGSSSEDLNG MVTRFESLKI YRDSLGETVM RMGDLHYLQS   60
RNEKWREQLG QKFEEIRWLI EEMRHRLKAT ENSFEQITFM QALQLLLEVE QEIRAFSFQL  120
I                                                                 121
```

The invention claimed is:

1. An immunogenic composition comprising one or more polypeptides comprising an amino acid sequence at least 80% identical to the amino acid sequence of SEQ ID NO:3, wherein the one or more polypeptides each comprise mutations to alanine or glycine at each of residues 238, 239, 241, 242, and 243 relative to the amino acid sequence of SEQ ID NO:3.

2. The immunogenic composition of claim 1, wherein the one or more polypeptides comprise an amino acid sequence at least 90% identical to the amino acid sequence of SEQ ID NO:3.

3. The immunogenic composition of claim 1, wherein the one or more polypeptides comprise an amino acid sequence at least 95% identical to the amino acid sequence of SEQ ID NO:3.

4. The immunogenic composition of claim 1, wherein the one or more polypeptides further comprise a mutation to alanine or glycine at each residue selected from the group consisting of 172, 174, 175, and 176 relative to SEQ ID NO:3.

5. The immunogenic composition of claim 1, wherein the one or more polypeptides further comprise a mutation to alanine or glycine at each residue selected from the group consisting of 147, 151, 156, 158, 160, and 161 relative to SEQ ID NO:3.

6. The immunogenic composition of claim 1, wherein the one or more polypeptides further comprise a mutation to alanine or glycine at each residue selected from the group consisting of 61, 64, 66, and 69 relative to SEQ ID NO:3.

7. The immunogenic composition of claim 1, further comprising one or more polypeptides comprising an amino acid sequence at least 80% identical to the amino acid sequence SEQ ID NO:1, wherein the one or more polypeptides each comprise mutations to alanine or glycine at each of residues 159, 415, 419, 490, and 491 relative to the amino acid sequence of SEQ ID NO:1.

8. The immunogenic composition of claim 1, further comprising one or more polypeptides comprising an amino acid sequence at least 80% identical to the amino acid sequence SEQ ID NO:5, wherein the one or more polypeptides each comprise mutations to alanine or glycine at each of residues 71, 86, 88, 90, 95 relative to the amino acid sequence of SEQ ID NO:5.

9. A method for immunizing a subject against infection with an influenza virus, inducing an immune response against influenza virus, or reducing an influenza virus infection in a subject in need thereof, comprising administering the immunogenic composition of claim 1.

* * * * *